(12) United States Patent
Isaac et al.

(10) Patent No.: US 6,372,211 B1
(45) Date of Patent: *Apr. 16, 2002

(54) METHODS AND COMPOSITIONS FOR CONTROLLING INSECTS

(75) Inventors: Barbara G. Isaac, St. Charles; John T. Greenplate, Manchester; John P. Purcell; Charles P. Romano, both of Ballwin, all of MO (US)

(73) Assignee: Monsanto Technolgy LLC

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/063,733

(22) Filed: Apr. 21, 1998

Related U.S. Application Data

(60) Provisional application No. 60/044,504, filed on Apr. 21, 1997.

(51) Int. Cl.[7] .............................................. A61K 38/44
(52) U.S. Cl. ..................... 424/94.4; 424/94.2; 424/94.5
(58) Field of Search ................................. 435/189, 183; 424/94.2, 94.4, 94.5

(56) References Cited

U.S. PATENT DOCUMENTS

| 4,224,407 A | 9/1980 | Kusakabe et al. | ............. 435/25 |
| 4,234,691 A | 11/1980 | Kusakabe et al. | .......... 435/191 |

OTHER PUBLICATIONS

"Occurrence of a Novel Enzyme, L–Lysine Oxidase with Antitumor Activity in Culture Extract of *Trichoderma viride*," Hitoshi Kusakabe et al., *Agric. Biol. Chem.*, 43 (2), 1979, pp. 337–343.

"A New Antitumor Enzyme, L–Lysine α–Oxidase from *Trichoderma viride*," by Hitoshi Kusakabe et al., *J. Biol. Chem.*, 256, 1980, pp. 976–981.

*Primary Examiner*—Jean C. Witz
(74) *Attorney, Agent, or Firm*—T. K. Ball; Howrey Simon Arnold & White, LLP

(57) ABSTRACT

Compositions and methods for controlling insects by co-expressing an amino acid oxidase and a second enzyme that provides insecticidal activity when present in a mixture with the amino acid oxidase are disclosed. Also disclosed are DNA and protein sequences, and transformed microorganisms and plants useful for achieving such insect control.

16 Claims, 29 Drawing Sheets

SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
        (A) LENGTH: 22 amino acids
        (B) TYPE: amino acid
        (C) STRANDEDNESS: Not Relevant
        (D) TOPOLOGY: linear (xi) SEQUENCE DESCRIPTION: SEQ ID NO:1:

Asp Ala Pro Pro Gln Pro Pro Lys Glu Asp Glu Leu Val Glu Leu Ile
1               5                   10                  15

Leu Gln Asn Leu Ala Arg
            20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (xi) SEQUENCE DESCRIPTION: SEQ ID NO:2:

TCRTCYTCYT TNGGNGGYTG                                         20

(2) INFORMATION FOR SEQ ID NO:3:

(i) SEQUENCE CHARACTERISTICS:
        (A) LENGTH: 13 amino acids
        (B) TYPE: amino acid (C) STRANDEDNESS: Not Relevant
        (D) TOPOLOGY: linear (xi) SEQUENCE DESCRIPTION: SEQ ID NO:3:

Gly Leu Asn Leu His Pro Thr Gln Ala Asp Ala Ile Arg
1               5                   10

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 18
        (D) OTHER INFORMATION: /mod_base= i (xi) SEQUENCE DESCRIPTION: SEQ ID NO:4:

ATNGCRTCNG CYTGNGTNGG RTG                                             23

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 21
        (D) OTHER INFORMATION: /mod_base= i (xi) SEQUENCE DESCRIPTION: SEQ ID NO:5:

CAYCCNACNC ARGCNGAYGC NAT                                             23

(2) INFORMATION FOR SEQ ID NO:6:

(i) SEQUENCE CHARACTERISTICS:
        (A) LENGTH: 20 base pairs (B) TYPE: nucleic acid
        (C) STRANDEDNESS: single
        (D) TOPOLOGY: linear (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (xi) SEQUENCE DESCRIPTION: SEQ ID NO:6:

AAYCTNCAYC CNACNCARGC                                        20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (xi) SEQUENCE DESCRIPTION: SEQ ID NO:7:

AAYTTRCAYC CNACNCARGC                                        20

(2) INFORMATION FOR SEQ ID NO:8:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (xi) SEQUENCE DESCRIPTION: SEQ ID NO:8:

Lys Gln Gln Ala Phe Gly Tyr Tyr Lys
1               5

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 18
        (D) OTHER INFORMATION: /mod_base= i (xi) SEQUENCE DESCRIPTION: SEQ ID NO:9:

AARCARCARG CNTTYGGNTA                                                  20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 12
        (D) OTHER INFORMATION: /mod_base= i (xi) SEQUENCE DESCRIPTION: SEQ ID NO:10:

CARGCNTTYG GNTAYTAYAA                                                  20

(2) INFORMATION FOR SEQ ID NO:11:

(i) SEQUENCE CHARACTERISTICS:
        (A) LENGTH: 12 amino acids
        (B) TYPE: amino acid
        (C) STRANDEDNESS: Not Relevant
        (D) TOPOLOGY: linear (xi) SEQUENCE DESCRIPTION: SEQ ID NO:11:

Tyr Pro Ser Tyr Asn Xaa Asp Asp Thr Gly Glu Ala
1               5                   10

(2) INFORMATION FOR SEQ ID NO:12:

(i) SEQUENCE CHARACTERISTICS:
        (A) LENGTH: 763 base pairs
        (B) TYPE: nucleic acid
        (C) STRANDEDNESS: single
        (D) TOPOLOGY: linear (xi) SEQUENCE DESCRIPTION: SEQ ID NO:12:

AAGCAGCAGG CGTGGGTATT ACAAAGAGAA GCTTGCTGAG GACTTCGACA AAGGGTTCGA       60

TGAGCTCATG CTCGTCGACG ACATGACCAC TCGAGAGTAC TTGAAGCGAG GCGGGCCGAA      120

GGGAGAGGCG CCCAAGTATG ACTTTTTCGC CATCCAGTGG ATGGAGACAC AAAACACTGG      180

GACAAACCTG TTTGATCAGG CCTTTTCTGA AAGCGTCATC GACTCGTTTG ACTTTGACAA      240

CCCGACAAAG CCCGAATGGT ACTGCATCGA GGGAGGAACA TCGCTTTTGG TGGACGCCAT      300

GAAAGAAACC CTTGTCCACA AGGTACAGAA CAACAAGAGA GTTGATGCCA TTTCCATTGA      360

CTTGGACGCT CCGGATGATG GGAACATGTC GGTCAGGATA GGCGGAAAGG ATCACTCCGG      420

ATATAGCACC GTCTTCAACA CCACCGCTCT GGGCTGCCTT GACCGCATGG ATCTGCGTGT      480

CTCAACTTGC ACCCTACTCA GGCAGATGCC ATTCGATGTT TGCACTATGA CAACTCGACC      540

AAGGTGGCTC TCAAGTTTAC TACCCGTGGT GGATCAAGGA CTGTGGCATC ACTTGCGGTG      600

GCGCGGCCTC GACTGATCTA CCTCTACGAA CTTGCGTTTA CCCATCATAC AACTTGGACG      660

ATACTGGTGA GGCTGTTCTG CTTGCCTCAT ACACTTGGTC TCAAGATGCA ACTCGCATTG      720

GATCGTTGGT GAAGGACGCT CCACCACACC CCCCAAAGAA GAC                       763

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:13:

```
ACCTCTACGA ACTTGCGTTT ACC                                                 23
```

(2) INFORMATION FOR SEQ ID NO:14:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:14:

```
CAACTCGCAT TGGATCGTTG GTG                                                 23
```

(2) INFORMATION FOR SEQ ID NO:15:

(i) SEQUENCE CHARACTERISTICS:
        (A) LENGTH: 2700 base pairs
        (B) TYPE: nucleic acid
        (C) STRANDEDNESS: single
        (D) TOPOLOGY: linear (xi) SEQUENCE DESCRIPTION: SEQ ID NO:15:

```
GATCTAACCA CGGCTTTTGC GCTCCAGGCC GCTCCCACCG CATGCAGGCA TTCCATCCCA         60
ACCCTCAAAT GAGTCTAGCC TTCAGCCTTC ACCTGCAAGT GGCTGGCGGG ATGTGTTCGG        120
GACTTCATGC AGCTCAAGAC TCTGAGCCTC GCTGATGATG AGGGGATTCA AGACATGCAT        180
TTCAGCTTTG GTGATAAGAG CCAATAGTGT TTGCTGCTCA TGTTGTCTGT GCTTTCTGTG        240
CCGCTTCTGT GCCGTTATCG CCTGTTTTAT AGCGTCAGCC AAGCCAATCA GTCTCCTCCC        300
GCTGGAATCC CTCCCGTGTC ATTTTTCTCC CCGTTACGCA ATTCTTCCTT AATCGATACT        360
ACTATACAGT ATGATGGAGA GCTTTTACTG GTGCCCACTT TGTGGCAATG CTATTGATGT        420
CTTTCAAGTC AGAGCTGAGC ACGGAAATCG ATAGCCTGAC CTCTAACGGC TGTCGGTAGC        480
TGAAAGGGGA TGAGAGCGGA GGCGGTTAAT TCAGCTAGGT ATTGATTAAG GGAACTGGCA        540
GCTTGTGTTC ACGTAGGCTC TGAATAAGAT ATAAATAAGG AGAGGAAAGG CTACGCAATC        600
GAAGTAAACG GCTACCATCG CCATCTTCTC ATCATAGCTA TCCCGTTACT ATATTTGCAA        660
ACATGGACAA TGTTGACTTT GCTGAATCTG TCCGAACCCG CTGGGCGAGG CGACTCATTC        720
GTGAGAAGGT CGCCAAGGAA CTCAACATTC TAACCGAAAG ACTTGGTGAG GTGCCCGGCA        780
TCCCTCCTCC AAATGAAGGC AGGTTCCTGG GCGGCGGCTA CTCTCACGAC AATCTACCGT        840
CTGATCCCCT CTATTCCAGC ATTAAGCCGG CTCTTCTAAA GGAGGCTCCT CGAGCAGAAG        900
AGGAACTGCC GCCTCGAAAG GTGTGCATCG TAGGCGCTGG TGTTTCCGGC CTCTACATAG        960
CCATGATTTT GGATGATTTG AAAATCCCAA ATCTCACTTA CGACATCTTC GAATCCAGTT       1020
CCAGAACTGG TGGCCGTTTG TATACGCACC ATTTCACCGA CGCCAAGCAT GACTATTACG       1080
ACATTGGTGC TATGCGATAT CCTGACATCC CCAGCATGAA ACGTACCTTT AACCTGTTTA       1140
AACGTACTGG GATGCCTCTC ATCAAATATT ACCTTGATGG CGAGAATACC CCTCAGCTGT       1200
ACAATAATCA CTTCTTCGCC AAGGGCGTGT CGGACCCCTA TATGGTGAGC GTGGCCAATG       1260
GCGGCACCGT GCCAGATGAT GTTGTCGATA GTGTTGGAGA GAAGTTACAA CAGGCTTTCG       1320
```

```
GTTATTACAA AGAGAAGCTT GCTGAGGACT TCGACAAAGG GTTCGATGAG CTCATGCTCG      1380

TCGACGACAT GACCACTCGA GAGTACTTGA AGCGAGGCGG GCCGAAGGGA GAGGCGCCCA      1440

AGTATGACTT TTTCGCCATC CAGTGGATGG AGACACAAAA CACTGGGACA AACCTGTTTG      1500

ATCAGGCCTT TTCTGAAAGC GTCATCGACT CGTTTGACTT TGACAACCCG ACAAAGCCCG      1560

AATGGTACTG CATCGAGGGA GGAACATCGC TTTTGGTGGA CGCCATGAAA GAAACCCTTG      1620

TCCACAAGGT ACAGAACAAC AAGAGAGTTG ATGCCATTTC CATTGACTTG GACGCTCCGG      1680

ATGATGGGAA CATGTCGGTC AGGATAGGCG GAAAGGATCA CTCCGGATAT AGCACCGTCT      1740

TCAACACCAC CGCTCTGGGC TGCCTTGACC GCATGGATCT GCGTGGTCTC AACTTGCACC      1800

CTACTCAGGC AGATGCCATT CGATGTTTGC ACTATGACAA CTCGACCAAG GTGGCTCTCA      1860

AGTTTAGCTA CCCGTGGTGG ATCAAGGACT GTGGCATCAC TTGCGGTGGC GCGGCCTCGA      1920

CTGATCTACC TCTACGAACT TGCGTTTACC CATCATACAA CTTGGACGAT ACTGGTGAGG      1980

CTGTTCTGCT TGCCTCATAC ACTTGGTCTC AAGATGCAAC TCGCATTGGA TCGTTGGTGA      2040

AGGACGCTCC ACCACAGCCG CCCAAGGAGG ATGAGCTTGT CGAGCTGATC CTGCAGAACC      2100

TAGCCCGCCT GCACGCTGAG CATATGACCT ACGAGAAGAT TAAGGAGGCT TACACGGGCG      2160

TATATCACGC CTATTGCTGG GCTAATGATC CCAATGTCGG TGGTGCTTTC GCCCTCTTCG      2220

GTCCCGGCCA GTTCAGCAAT CTGTATCCAT ACCTGATGCG GCCAGCGGCG GGCGGCAAGT      2280

TCCATATCGT CGGAGAGGCA TCTAGTGTGC ATCACGCCTG GATCATAGGG TCTTTGGAGA      2340

GCGCTTACAC CGCTGTGTAC CAGTTCTTGT ACAAGTACAA GATGTGGGAT TACTTGAGGT      2400

TGTTGTTGGA GCGCTGGCAG TATGGTCTCC AGGAGTTAGA GACGGGGAAG CACGGTACGG      2460

CTCATTTGCA GTTTATTCTA GGTTCACTTC CCAAGGAGTA CCAGGTGAAG ATTTAAAGCG      2520

AAAGAGGTAC TACGGCATGG AGACAATTTT GGGTAGAGAT TCTAGTATTC CAGCAGTTTC      2580

ATAGAAAGTG TGATGTTTGT TAGTCCCACT TTGAGTCTCT GTTCGTCTGA AAGTGCCTAC      2640

TATGACCCGG TGATTAGTAT AACAGAATTT GTCATTCTCA TCAGCCATAA ACCGAGGTCA      2700

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:16:

CATGTCGTCG ACGAGCATGA GC                                                22

(2) INFORMATION FOR SEQ ID NO:17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:17:

CATCGAACCC TTTGTCGAAG TCC                                               23

(2) INFORMATION FOR SEQ ID NO:18:

(i) SEQUENCE CHARACTERISTICS:
        (A) LENGTH: 25 base pairs
        (B) TYPE: nucleic acid
```

```
            (C) STRANDEDNESS: single
            (D) TOPOLOGY: linear (xi) SEQUENCE DESCRIPTION: SEQ ID NO:18:

CAGCAAGCTT CTCTTTGTAA TACCC                                           25

(2) INFORMATION FOR SEQ ID NO:19:

(i) SEQUENCE CHARACTERISTICS:
            (A) LENGTH: 274 base pairs
            (B) TYPE: nucleic acid
            (C) STRANDEDNESS: single
            (D) TOPOLOGY: linear (xi) SEQUENCE DESCRIPTION: SEQ ID NO:19:

ACTATACGAC ATTGGTGCTA TGCGATATCC TGACATCCCC AGCATGAAAC GTACCTTTAA      60

CCTGTTTAAA CGTACTGGGA TGCCTCTCAT CAAATATTAC CTTGATGGCG AGAATACCCC     120

TCAGCTGTAC AATAATCACT TCTTCGCCAA GGGCGTGTCG GACCCCTATA TGGTGAGCGT     180

GGCCAATGGC GGCACCGTSC CAGATGATGT TNGTCGATAG TGTTGGAGAG AAGTTACAAC     240

AGGCTTTCGG GTATTACAAA GAGAAGCTTG CTGA                                 274

(2) INFORMATION FOR SEQ ID NO:20:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:20:

GTCGAAGTCC TCAGCCAGCT TCTCTTTGTA A                                    31

(2) INFORMATION FOR SEQ ID NO:21:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO:21:

CATGCTGGGG ATGTCAGG                                                   18

(2) INFORMATION FOR SEQ ID NO:22:

(i) SEQUENCE CHARACTERISTICS:
            (A) LENGTH: 262 base pairs
            (B) TYPE: nucleic acid
            (C) STRANDEDNESS: single
            (D) TOPOLOGY: linear (xi) SEQUENCE DESCRIPTION: SEQ ID NO:22:

ACCATCGCCA TCTTCTCATC ATAGCTATCC CGTTACTATA TCTGCAAACA TGGACAATGT      60

TGACTTTGCT GAATCTGTCC GAACCCGCTG GGCGAGGCGA CTCATTCGTG AGAAGGTCGC     120

CAAGGAACTC AACATTCTAA CCGAAAGACT TGGTGAGGTG CCCGGCATCC CTCCTCCAAA     180

TGAAGGCAGG TTCCTGGGCG GCGGCTACTC TCTCGACAAT CTACCGCCTG ATCCCCTCTA     240

TTCCAGCATT AAGCCGGCTC TT                                              262

(2) INFORMATION FOR SEQ ID NO:23:

(i) SEQUENCE CHARACTERISTICS:
```

(A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:23:

GARCARAAYA AYTTYTTYAA YCAYGC                                            26

(2) INFORMATION FOR SEQ ID NO:24:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (xi) SEQUENCE DESCRIPTION: SEQ ID NO:24:

Val Val Val Leu Glu Gln Asn Asn Phe Phe Asn His Ala Gly Ser Ser
1               5                   10                  15

Asn Asp Leu Ala
            20

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 9
        (D) OTHER INFORMATION: /mod_base= i (xi) SEQUENCE DESCRIPTION: SEQ ID NO:25:

ATGTAYACNG ARCAYTAYAT G                                                 21

(2) INFORMATION FOR SEQ ID NO:26:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: linear (xi) SEQUENCE DESCRIPTION: SEQ ID NO:26:

Thr Met Tyr Thr Glu Asp Tyr Met Ala Asp Leu Ala Lys
1               5                   10

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 3
        (D) OTHER INFORMATION: /mod_base= i (xi) SEQUENCE DESCRIPTION: SEQ ID NO:27:

GGNGCRAAYT GRAACCACAT                                                   20

(2) INFORMATION FOR SEQ ID NO:28:

(i) SEQUENCE CHARACTERISTICS:
      (A) LENGTH: 15 amino acids
      (B) TYPE: amino acid
      (C) STRANDEDNESS: Not Relevant
      (D) TOPOLOGY: linear (xi) SEQUENCE DESCRIPTION: SEQ ID NO:28:

Gly Thr Ile Phe Pro Ser Met Trp Phe Gln Phe Ala Pro Asp Lys
1               5                   10                  15

(2) INFORMATION FOR SEQ ID NO:29:

(i) SEQUENCE CHARACTERISTICS:
      (A) LENGTH: 623 base pairs
      (B) TYPE: nucleic acid
      (C) STRANDEDNESS: single
      (D) TOPOLOGY: linear (xi) SEQUENCE DESCRIPTION: SEQ ID NO:29:

```
ATGTATACGG AGGACTACAT GGCCGATCTT GCCAAGGAAG CCTTGGCCCT CTGGGATGAT      60

CTTGAGAGAG ATTCCGGTAC GCCACTGCGA TGGATGAGCG GCCTCCTCAA CTTTGGCGAT     120

AAGGACTATG GCGGCGATAC ACCCGAAGGA ACCTTGTTGG GGCCAATTGC GAACCTGGAC     180

CGCCTGGGAA TGACTTATCA AGAGTTATCT GCTAAGGAGA TTGAGGCACG CTACCCGTTC     240

AAGAACCTCG ACCCTAAGTA CATTGGTCTC TTCGCGCCAG ACAATGGCGT CATCAATGTC     300

CAGCTTCTGT TGAGGACGCT GTATAAATTA TCACTGGACT ATGGTGCCAC TGCGAAACAG     360

CATACCAAAG TCCAGGCTAT TAAGCCTTCT AATCATTCTC ATTACGCCTG GGATGTTCAC     420

GCTATTCGTC ATGAGACCGA AGCCGCTGTC TTCAAGGCAA AGAAGATCAT TATCGCCTCT     480

GGTGCTTACG TGAACCATGT TCTCAAGCCG AGCTTCGACA TTTCTCTCGA TCTCGACATC     540

TGAGAAATGG TGTTTTCTTA CTTTAACTGC AATGCAGGAC CCAAAGGAAC AATATTCCCC     600

AGCATGTGGT TCCAATTCGC CCC                                            623
```

(2) INFORMATION FOR SEQ ID NO:30:

(i) SEQUENCE CHARACTERISTICS:
      (A) LENGTH: 11 amino acids
      (B) TYPE: amino acid
      (C) STRANDEDNESS: Not Relevant
      (D) TOPOLOGY: linear (xi) SEQUENCE DESCRIPTION: SEQ ID NO:30:

Leu Gly Met Thr Tyr Gln Glu Met Ser Ala Lys
1               5                   10

(2) INFORMATION FOR SEQ ID NO:31:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (xi) SEQUENCE DESCRIPTION: SEQ ID NO:31:

CCGGAATTCC TTGGCAAGAT CGGCCAT                                         27

(2) INFORMATION FOR SEQ ID NO:32:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (xi) SEQUENCE DESCRIPTION: SEQ ID NO:32:

| | |
|---|---|
| CCTCCGTATA CATTGTTCG | 19 |

(2) INFORMATION FOR SEQ ID NO:33:

(i) SEQUENCE CHARACTERISTICS:
        (A) LENGTH: 381 base pairs
        (B) TYPE: nucleic acid
        (C) STRANDEDNESS: single
        (D) TOPOLOGY: linear (xi) SEQUENCE DESCRIPTION: SEQ ID NO:33:

| | |
|---|---|
| GAATTCGGCT TCTACTACTA CTAGGCCACG CGTCGACTAG TACGGGGGGG GGGGGGGTGG | 60 |
| GGGTGACATC ACGTTGTTTC AGTGCTGGAT ATAGGTTCCT CCTAGAGTTT ACCTATTGAG | 120 |
| ACAGATACTT CAATCACATT CTCTAGGATA TCGAATCAAA CCGAAAACAC TTGCTTCAGA | 180 |
| ATCCCCTAAA CATGGCAGAC GAAATCTACG ATGTTGTCGT CATCGGCGGC GGCCCAATTG | 240 |
| GATTGGCAGC TGCCTATGAA GCAGCCAAGG AGGGTGCCAA AGTCGTTGTT CTCGAGCAAA | 300 |
| ACAATTTCTT CAACCATGCT GGGAGCTCTA ACGATTTGGC TCGGATGTTT CGAACAATGT | 360 |
| ATACGGAGGA AGCCGAATTC C | 381 |

(2) INFORMATION FOR SEQ ID NO:34:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:34:

| | |
|---|---|
| CCGGAATTCA TGGCCGATCT TGCCAAGGAA G | 31 |

(2) INFORMATION FOR SEQ ID NO:35:

(i) SEQUENCE CHARACTERISTICS:
        (A) LENGTH: 1426 base pairs
        (B) TYPE: nucleic acid
        (C) STRANDEDNESS: single
        (D) TOPOLOGY: linear (xi) SEQUENCE DESCRIPTION: SEQ ID NO:35:

| | |
|---|---|
| GAATTCGGCT TCCGGAATTC ATGGCCGATC TTGCCAAGGA AGCCTTGGCC CTCTGGGATG | 60 |
| ATCTTGAGAG AGATTCCGGT ACGCCACTGC GATGGATGAG CGGCCTCCTC AACTTTGGCG | 120 |
| ATAAGGACTA TGGCGGCGAT ACACCCGAAG GAACCTTGTT GGGGCCAATT GCGAACCTGG | 180 |
| ACCGCCTGGG AATGACTTAT CAAGAGTTAT CTGCTAAGGA GATTGAGGCA CGCTACCCGT | 240 |
| TCAAGAACCT CGACCCTAAG TACATCGGTC TCTTCGCGCC AGACAATGGG CTCATCAATG | 300 |
| TCCAGCTTCT GTTGAGGACG CTGTATAAAT TATCACTGGA CTATGGTGCC ACTGCGAAAC | 360 |
| AGCATACCAA AGTCCAGGCT ATTAAGCCTT CTAATCATTC TCATTACGCC TGGGATGTTC | 420 |
| ACGCTATTCG TCATGAGACC GAAGCCGCTG TCTTCAAGGC AAAGAAGATC ATTATCGCCT | 480 |
| CTGGTGCTTA CGTGAACCAT GTTCTCAAGC CGAGCTTCGA CATTTCTCTC GATCTCGACA | 540 |
| TCTGGGAAAT GGTGTTTTCT TACTTTAACT GCAATGCAGG ACCCAAAGGA ACAATATTCC | 600 |
| CCAGCATGTG GTTCCAGTTT GCGCCTGATA AGAACGGCAG ATCACAGCTC TTCTATGGCT | 660 |
| TTCCAGCACT TCCATGGGGC CCTCCAAATC TTGCTCGTAT TGCTATGGAT GCGGCCACCA | 720 |
| GGCGGATCAA GGATCCCAAC GAGAGACTTA CAAGCACTAT TAACCCGGAG GATATTGCTG | 780 |

```
ATACGCAAGA GTTTATCCGC AATCATTGTG TCAACGTTGA TCCTACCATT CCTGCGTTGA      840

CATCGAGTTG CCTGCAGACC AATGTGTTTG ACAACATGTT TGTTCTGGAC TTTGTCCCTG      900

AAAAATATCT GAACGGCGGA GCCAAAGACA GTGTAGTCGT CTTCACAGCC GGATGGGCCA      960

TGAAGTTCGT GCCAATGATA GGAAAGGCAC TCGCTGACAT GGCACTCAAG GGAAGCTCTC     1020

CATATGCGCG CAAAGAATTT GCCATCACCC GCACAGATTC AGCGACCGGG AAGGGCATCA     1080

TTGTGGAAGG TGGATCAGAG AACCGATCGG TTAAGAGCAG CGCTTTTGTC TTCTACTCAC     1140

CAGGCATCCG GTTCTTCGTT TGCCGGCTTC CATAACACTG CACGGCAATA GAAGAAAGTG     1200

AATAGGGGTA AGCGGGCGGG ATAGGATATC TGTGGAACAC ACAATGAGAA GTGACCAAGA     1260

TCGCTGTTGA GAATACGCCA AAGCATACTA TAGCTTGTAG GTGTTGCTAT CTGGTCTACA     1320

GTGTTGCAAA GATGCATAAA TAGGTGAAAA AGAATTGATG AGGTATATGA ATCCTCAGTA     1380

AAAAAAAAAA AAAAAAATCG ATGTCGACTC GAGTCAAGCC GAATTC                    1426
```

(2) INFORMATION FOR SEQ ID NO:36:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:36:

```
GGGAGATCTC CATGGCAGAC GAAATCT                                           27
```

(2) INFORMATION FOR SEQ ID NO:37:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:37:

```
GGCTTTCCAG CACTTCCTTG GGGCCCTCCA A                                      31
```

(2) INFORMATION FOR SEQ ID NO:38:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:38:

```
TTGGAGGGCC CCAAGGAAGT GCTGGAAAGC C                                      31
```

(2) INFORMATION FOR SEQ ID NO:39:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:39:

```
CCCAAGCTTG AATTCACTTT CTTCTATTGC C                                      31
```

(2) INFORMATION FOR SEQ ID NO:40:

(i) SEQUENCE CHARACTERISTICS:

(A) LENGTH: 1385 base pairs
(B) TYPE: nucleic acid
(C) STRANDEDNESS: single
(D) TOPOLOGY: linear (xi) SEQUENCE DESCRIPTION: SEQ ID NO:40:

| | |
|---|---|
| GGGAGATCTC CATGGCAGAC GAAATCTACG ATGTTGTCGT CATCGGCGGC GGCCCAATTG | 60 |
| GATTGGCAGC TGCCTATGAA GCAGCCAAGG AGGGTGCCAA AGTCGTTGTT CTCGAGCAAA | 120 |
| ACAATTTCTT CAACCATGCT GGGAGCTCTA ACGATTTGGC TCGGATGTTT CGAACAATGT | 180 |
| ATACGGAGGA TTATATGGCC GATCTTGCCA AGGAAGCCTT GGCCCTCTGG GATGATCTTG | 240 |
| AGAGAGATTC CGGTACGCCA CTGCGATGGA TGAGCGGCCT CCTCAACTTT GGCGATAAGG | 300 |
| ACTATGGCGG CGATACACCC GAAGGAACCT TGTTGGGGCC AATTGCGAAC CTGGACCGCC | 360 |
| TGGGAATGAC TTATCAAGAG TTATCTGCTA AGGAGATTGA GGCACGCTAC CCGTTCAAGA | 420 |
| ACCTCGACCC TAAGTACATT GGTCTCTTCG CGCCAGACAA TGGGCTCATC AATGTCCAGC | 480 |
| TTCTGTTGAG GACGCTGTAT AAATTATCAC TGGACTATGG TGCCACTGCG AAACAGCATA | 540 |
| CCAAAGTCCA GGCTATTAAG CCTTCTAATC ATTCTCATTA CGCCTGGGAT GTTCACGCTA | 600 |
| TTCGTCATGA GACCGAAGCC GCTGTCTTCA AGGCAAAGAA GATCATTATC GCCTCTGGTG | 660 |
| CTTACGTGAA CCATGTTCTC AAGCCGAGCT TCGACATTTC TCTCGATCTC GACATCTGGG | 720 |
| AAATGGTGTT TTCTTACTTT AACTGCAATG CAGGACCCAA AGGAACAATA TTCCCCAGCA | 780 |
| TGTGGTTCCA GTTTGCGCCT GATAAGAACG GCAGATCACA GCTCTTCTAT GGCTTTCCAG | 840 |
| CACTTCCTTG GGGCCCTCCA AATCTTGCTC GTATTGCTGT GGATGCGGCC ACCAGGCGGA | 900 |
| TCAAGGATCC CAACGAGAGA CTTACAAGCA CTATTAACCC GGAGGATATT GCTGATACGC | 960 |
| AAGAGTTTAT CCGCAATCAT TGTGTCAACG TTGATCCTAC CATTCCTGCG TTGACATCGA | 1020 |
| GTTGCCTGCA GACCAATGTG TTTGACAACA TGTTTGTTCT GGACTTTGTC CCTGAAAAAT | 1080 |
| ATCTGAACGG CGGAGCCAAA GACAGTGTAG TCGTCTTCAC AGCCGGATGG GCCATGAAGT | 1140 |
| TCGTGCCAAT GATAGGAAAG GCACTCGCTG ACATGGCACT CAAGGGAAGC TCTCCATATG | 1200 |
| CGCGCAAAGA ATTTGCCATC ACCCGCACAG ATTCAGCGAC CGGGAAGGGC ATCATTGTGG | 1260 |
| AAGGTGGATC AGAGAACCGA TCGGTTAAGA GCAGCGCTTT TGTCTTCTAC TCACCAGGCA | 1320 |
| TCCGGTTCTT CGTTTGCCGG CTTCCATAAC ACTGCACGGC AATAGAAGAA AGTGAATTCA | 1380 |
| AGCTT | 1385 |

(2) INFORMATION FOR SEQ ID NO:41:

(i) SEQUENCE CHARACTERISTICS:
(A) LENGTH: 445 amino acids
(B) TYPE: amino acid
(C) STRANDEDNESS: Not Relevant
(D) TOPOLOGY: linear (xi) SEQUENCE DESCRIPTION: SEQ ID NO:41:

```
Met Ala Asp Glu Ile Tyr Asp Val Val Ile Gly Gly Gly Pro Ile
1               5                  10                  15

Gly Leu Ala Ala Ala Tyr Glu Ala Ala Lys Glu Gly Ala Lys Val Val
            20                  25                  30

Val Leu Glu Gln Asn Asn Phe Phe Asn His Ala Gly Ser Ser Asn Asp
        35                  40                  45

Leu Ala Arg Met Phe Arg Thr Met Tyr Thr Glu Asp Tyr Met Ala Asp
    50                  55                  60

Leu Ala Lys Glu Ala Leu Ala Leu Trp Asp Asp Leu Glu Arg Asp Ser
```

```
                 65                  70                  75                  80
Gly Thr Pro Leu Arg Trp Met Ser Gly Leu Leu Asn Phe Gly Asp Lys
                    85                  90                  95

Asp Tyr Gly Gly Asp Thr Pro Glu Gly Thr Leu Leu Gly Pro Ile Ala
                100                 105                 110

Asn Leu Asp Arg Leu Gly Met Thr Tyr Gln Glu Leu Ser Ala Lys Glu
                115                 120                 125

Ile Glu Ala Arg Tyr Pro Phe Lys Asn Leu Asp Pro Lys Tyr Ile Gly
            130                 135                 140

Leu Phe Ala Pro Asp Asn Gly Leu Ile Asn Val Gln Leu Leu Leu Arg
145                 150                 155                 160

Thr Leu Tyr Lys Leu Ser Leu Asp Tyr Gly Ala Thr Ala Lys Gln His
                165                 170                 175

Thr Lys Val Gln Ala Ile Lys Pro Ser Asn His Ser His Tyr Ala Trp
                180                 185                 190

Asp Val His Ala Ile Arg His Glu Thr Glu Ala Ala Val Phe Lys Ala
            195                 200                 205

Lys Lys Ile Ile Ile Ala Ser Gly Ala Tyr Val Asn His Val Leu Lys
            210                 215                 220

Pro Ser Phe Asp Ile Ser Leu Asp Leu Asp Ile Trp Glu Met Val Phe
225                 230                 235                 240

Ser Tyr Phe Asn Cys Asn Ala Gly Pro Lys Gly Thr Ile Phe Pro Ser
                245                 250                 255

Met Trp Phe Gln Phe Ala Pro Asp Lys Asn Gly Arg Ser Gln Leu Phe
                260                 265                 270

Tyr Gly Phe Pro Ala Leu Pro Trp Gly Pro Pro Asn Leu Ala Arg Ile
            275                 280                 285

Ala Val Asp Ala Ala Thr Arg Arg Ile Lys Asp Pro Asn Glu Arg Leu
290                 295                 300

Thr Ser Thr Ile Asn Pro Glu Asp Ile Ala Asp Thr Gln Glu Phe Ile
305                 310                 315                 320

Arg Asn His Cys Val Asn Val Asp Pro Thr Ile Pro Ala Leu Thr Ser
                325                 330                 335

Ser Cys Leu Gln Thr Asn Val Phe Asp Asn Met Phe Val Leu Asp Phe
                340                 345                 350

Val Pro Glu Lys Tyr Leu Asn Gly Gly Ala Lys Asp Ser Val Val Val
                355                 360                 365

Phe Thr Ala Gly Trp Ala Met Lys Phe Val Pro Met Ile Gly Lys Ala
370                 375                 380

Leu Ala Asp Met Ala Leu Lys Gly Ser Ser Pro Tyr Ala Arg Lys Glu
385                 390                 395                 400

Phe Ala Ile Thr Arg Thr Asp Ser Ala Thr Gly Lys Gly Ile Ile Val
                405                 410                 415

Glu Gly Gly Ser Glu Asn Arg Ser Val Lys Ser Ser Ala Phe Val Phe
                420                 425                 430

Tyr Ser Pro Gly Ile Arg Phe Phe Val Cys Arg Leu Pro
                435                 440                 445

(2) INFORMATION FOR SEQ ID NO:42:

(i) SEQUENCE CHARACTERISTICS:
            (A) LENGTH: 2093 base pairs
            (B) TYPE: nucleic acid
            (C) STRANDEDNESS: single
            (D) TOPOLOGY: linear
```

(xi) SEQUENCE DESCRIPTION: SEQ ID NO:42:

```
ATATGTCGCA TTCTGGACAT TCTACGGTAT CATTATTTGT GGCGCAGTGG TTTATACGAC      60
TCAATTGAGT ATTATATTAA GCCGACATTC CGAAGGTCTT CTCTATCGCC ACATCACGTT     120
GTTTCAGTGC TGGATATAGG TTCCTCCTAG AGTTTACCTA TTGAGACAGA TACTTCAATC     180
ACATTCTCTA GGATATCGAA TCAAACCGAA AACACTTGCT TCAGAATCCC CTAAACATGG     240
CAGACGAAAT CTACGATGTT GTCGTCATCG GCGGCGGCCC AATTGGATTG GCAGCTGCCT     300
ATGAAGCAGC CAAGGAGGGT GCCAAAGTCG TTGTTCTCGA GCAAAACAAT TTCTTCAACC     360
ATGCTGGGAG CTCTAACGAT TTGGCTCGGA TGTTTCGAAC AATGTGAGTT ATTTTTTTGT     420
CTTTTTTCTT ACTCTCGTTT TCACAGACAC AGCTAATCAT CCGATCAGGT ATACGGAGGA     480
TTATATGGCC GATCTTGCCA AGGAAGCCTT GGCCCTCTGG GATGATCTTG AGAGAGATTC     540
CGGTACGCCA CTGCGATGGA TGAGCGGCCT CCTCAACTTT GGCGATAAGG ACTATGGCGG     600
CGATACACCC GAAGGTATGA ATCCTCCCA CAATAATATG GGTTTTGGCG CCCTTGTCTC      660
ACGATTTCAA CAGGAACCTT GTTGGGGCCA ATTGCGAACC TGGACCGCCT GGGAATGACT     720
TATCAAGAGT GTAAGTTGTG GCATGTATGC GAACGACGGT ATGCCCTCGA GTGCTAATCC     780
ATCGTCTCAC AGTATCTGCT AAGGAGATTG AGGCACGCTA CCCGTTCAAG AACCTCGACC     840
CTAAGTACAT TGGTCTCTTC GCGCCAGACA ATGGGCTCAT CAATGTCCAG CTTCTGTTGA     900
GGACGCTGTA TAAATTATCA CTGGACTATG GTGCCACTGC GAAACAGCAT ACCAAAGTCC     960
AGGCTATTAA GCCTTCTAAT CATTCTCATT ACGCCTGGGA TGTTCACGCT ATTCGTCATG    1020
AGACCGAAGC CGCTGTCTTC AAGGCAAAGA AGATCATTAT CGCCTCTGGT GCTTACGTGA    1080
ACCATGTTCT CAAGCCGAGC TTCGACATTT CTCTCGATCT CGACATCTGG GAAATGGTGT    1140
TTTCTTACTT TAACTGCAAT GCAGGACCCA AAGGAACAAT ATTCCCCAGT ACGTGGATTG    1200
ATCCATTTCT CTCGTGAGTT GGAGGTGTAT GAGCTAACTC CCATCAACTA GGCATGTGGT    1260
TCCAGTTTGC GCCTGATAAG AACGGCAGAT CACAGCTCTT CTATGGCTTT CCAGCACTTC    1320
CATGGGGCCC TCCAAATCTT GCTCGTATTG CTGTGGATGC GGCCACCAGG CGGATCAAGG    1380
ATCCCAACGA GAGACTTACA AGCACTATTA ACCCGGAGGA TATTGCTGAT ACGCAAGAGT    1440
TTATCCGCAA TCATTGTGTC AACGTTGATC CTACCATTCC TGCGTTGACA TCGAGTTGCC    1500
TGCAGACCAA TGTGTTTGGT GCGTATATTC ATATGGATGG ATTGACAAGG AAACTTACTG    1560
ATTCGGCTTA TAGACAACAT GTTTGTTCTG GACTTTGTCC CTGAAAAATA TCTGAACGGC    1620
GGAGCCAAAG ACAGTGTAGT CGTCTTCACA GCCGGATGGG CCATGAAGTT CGTGCCAATG    1680
ATAGGAAAGG CACTCGCTGA CATGGCACTC AAGGGAAGCT CTCCATATGC GCGCAAAGAA    1740
TTTGCCATCA CCCGCACAGA TTCAGCGACC GGGAAGGGCA TCATTGTGGA AGGTGGATCA    1800
GAGAACCGAT CGGTTAAGAG CAGCGCTTTT GTCTTCTACT CACCAGGCAT CCGGTTCTTC    1860
GTTTGCCGGC TTCCATAACA CTGCACGGCA ATAGAAGAAA GTGAATAGGG GGTAAGCAGG    1920
CGGGATAGGA TATCTGTGGA ACACACAATG AGAAGTGACC AAGATCGCTG TTGAGAATAC    1980
GCAAAGCATA CTATAGCTTG TAGGTGTTGC TATCTGGTCT ACAGTGTTGC AAAGATGCAT    2040
AAATAGGTGA AAAGAATTG ATGAGGTATA TGAATCCTCA GTAATCTTGA GCC            2093
```

(2) INFORMATION FOR SEQ ID NO:43:

(i) SEQUENCE CHARACTERISTICS:
        (A) LENGTH: 35 base pairs
        (B) TYPE: nucleic acid

```
            (C) STRANDEDNESS: single
            (D) TOPOLOGY: linear (xi) SEQUENCE DESCRIPTION: SEQ ID NO:43:

TTGCAAACCA TGGACAATGT TGACTTTGCT GAATC                              35

(2) INFORMATION FOR SEQ ID NO:44:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO:44:

GCCGTAGTAC CGAATTCTTA TTAAATCTTC ACC                                33

(2) INFORMATION FOR SEQ ID NO:45:

(i) SEQUENCE CHARACTERISTICS:
            (A) LENGTH: 1883 base pairs
            (B) TYPE: nucleic acid
            (C) STRANDEDNESS: single
            (D) TOPOLOGY: linear (xi) SEQUENCE DESCRIPTION: SEQ ID NO:45:

TTGCAAACCA TGGACAATGT TGACTTTGCT GAATCTGTCC GAACCCGCTG GGCGAGGCGA     60

CTCATTCGTG AGAAGGTCGC CAAGGAACTC AACATTCTAA CCGAAAGACT TGGTGAGGTG    120

CCCGGCATCC CTCCTCCAAA TGAAGGCAGG TTCCTGGGCG GCGGCTACTC TCACGACAAT    180

CTACCGTCTG ATCCCCTCTA TTCCAGCATT AAGCCGGCTC TTCTAAAGGA GGCTCCTCGA    240

GCAGAAGAGG AACTGCCGCC TCGAAAGGTG TGCATCGTAG GCGCTGGTGT TTCCGGCCTC    300

TACATAGCCA TGATTTTGGA TGATTTGAAA ATCCCAAATC TCACTTACGA CATCTTCGAA    360

TCCAGTTCCA GAACTGGTGG CCGTTTGTAT ACGCACCATT TCACCGACGC CAAGCATGAC    420

TATTACGACA TTGGTGCTAT GCGATATCCT GACATCCCCA GCATGAAACG TACCTTTAAC    480

CTGTTTAAAC GTACTGGGAT GCCTCTCATC AAATATTACC TTGATGGCGA GAATACCCCT    540

CAGCTGTACA ATAATCACTT CTTCGCCAAG GGCGTGTCGG ACCCCTATAT GGTGAGCGTG    600

GCCAATGGCG GCACCGTGCC AGATGATGTT GTCGATAGTG TTGGAGAGAA GTTACAACAG    660

GCTTTCGGTT ATTACAAAGA GAAGCTTGCT GAGGACTTCG ACAAAGGGTT CGATGAGCTC    720

ATGCTCGTCG ACGACATGAC CACTCGAGAG TACTTGAAGC GAGGCGGGCC GAAGGGAGAG    780

GCGCCCAAGT ATGACTTTTT CGCCATCCAG TGGATGGAGA CACAAAACAC TGGGACAAAC    840

CTGTTTGATC AGGCCTTTTC TGAAAGCGTC ATCGACTCGT TGACTTTGA CAACCCGACA    900

AAGCCCGAAT GGTACTGCAT CGAGGGAGGA ACATCGCTTT TGGTGGACGC CATGAAAGAA    960

ACCCTTGTCC ACAAGGTACA GAACAACAAG AGAGTTGATG CCATTTCCAT TGACTTGGAC   1020

GCTCCGGATG ATGGGAACAT GTCGGTCAGG ATAGGCGGAA AGGATCACTC CGGATATAGC   1080

ACCGTCTTCA ACACCACCGC TCTGGGCTGC CTTGACCGCA TGGATCTGCG TGGTCTCAAC   1140

TTGCACCCTA CTCAGGCAGA TGCCATTCGA TGTTTGCACT ATGACAACTC GACCAAGGTG   1200

GCTCTCAAGT TTAGCTACCC GTGGTGGATC AAGGACTGTG GCATCACTTG CGGTGGCGCG   1260

GCCTCGACTG ATCTACCTCT ACGAACTTGC GTTTACCCAT CATACAACTT GGACGATACT   1320

GGTGAGGCTG TTCTGCTTGC CTCATACACT TGGTCTCAAG ATGCAACTCG CATTGGATCG   1380

TTGGTGAAGG ACGCTCCACC ACAGCCGCCC AAGGAGGATG AGCTTGTCGA GCTGATCCTG   1440
```

```
CAGAACCTAG CCCGCCTGCA CGCTGAGCAT ATGACCTACG AGAAGATTAA GGAGGCTTAC    1500

ACGGGCGTAT ATCACGCCTA TTGCTGGGCT AATGATCCCA ATGTCGGTGG TGCTTTCGCC    1560

CTCTTCGGTC CCGGCCAGTT CAGCAATCTG TATCCATACC TGATGCGGCC AGCGGCGGGC    1620

GGCAAGTTCC ATATCGTCGG AGAGGCATCT AGTGTGCATC ACGCCTGGAT CATAGGGTCT    1680

TTGGAGAGCG CTTACACCGC TGTGTACCAG TTCTTGTACA AGTACAAGAT GTGGGATTAC    1740

TTGAGGTTGT TGTTGGAGCG CTGGCAGTAT GGTCTCCAGG AGTTAGAGAC GGGGAAGCAC    1800

GGTACGGCTC ATTTGCAGTT TATTCTAGGT TCACTTCCCA AGGAGTACCA GGTGAAGATT    1860

TAATAAGAAT TCGGTACTAC GGC                                             1883
```

(2) INFORMATION FOR SEQ ID NO:46:

(i) SEQUENCE CHARACTERISTICS:
        (A) LENGTH: 617 amino acids
        (B) TYPE: amino acid
        (C) STRANDEDNESS: Not Relevant
        (D) TOPOLOGY: linear (xi) SEQUENCE DESCRIPTION: SEQ ID NO:46:

```
Met Asp Asn Val Asp Phe Ala Glu Ser Val Arg Thr Arg Trp Ala Arg
1               5                   10                  15

Arg Leu Ile Arg Glu Lys Val Ala Lys Glu Leu Asn Ile Leu Thr Glu
            20                  25                  30

Arg Leu Gly Glu Val Pro Gly Ile Pro Pro Asn Glu Gly Arg Phe
        35                  40                  45

Leu Gly Gly Gly Tyr Ser His Asp Asn Leu Pro Ser Asp Pro Leu Tyr
    50                  55                  60

Ser Ser Ile Lys Pro Ala Leu Leu Lys Glu Ala Pro Arg Ala Glu Glu
65                  70                  75                  80

Glu Leu Pro Pro Arg Lys Val Cys Ile Val Gly Ala Gly Val Ser Gly
                85                  90                  95

Leu Tyr Ile Ala Met Ile Leu Asp Asp Leu Lys Ile Pro Asn Leu Thr
            100                 105                 110

Tyr Asp Ile Phe Glu Ser Ser Arg Thr Gly Gly Arg Leu Tyr Thr
        115                 120                 125

His His Phe Thr Asp Ala Lys His Asp Tyr Tyr Asp Ile Gly Ala Met
    130                 135                 140

Arg Tyr Pro Asp Ile Pro Ser Met Lys Arg Thr Phe Asn Leu Phe Lys
145                 150                 155                 160

Arg Thr Gly Met Pro Leu Ile Lys Tyr Tyr Leu Asp Gly Glu Asn Thr
                165                 170                 175

Pro Gln Leu Tyr Asn Asn His Phe Phe Ala Lys Gly Val Ser Asp Pro
            180                 185                 190

Tyr Met Val Ser Val Ala Asn Gly Gly Thr Val Pro Asp Asp Val Val
        195                 200                 205

Asp Ser Val Gly Glu Lys Leu Gln Gln Ala Phe Gly Tyr Tyr Lys Glu
    210                 215                 220

Lys Leu Ala Glu Asp Phe Asp Lys Gly Phe Asp Glu Leu Met Leu Val
225                 230                 235                 240

Asp Asp Met Thr Thr Arg Glu Tyr Leu Lys Arg Gly Gly Pro Lys Gly
                245                 250                 255

Glu Ala Pro Lys Tyr Asp Phe Phe Ala Ile Gln Trp Met Glu Thr Gln
            260                 265                 270

Asn Thr Gly Thr Asn Leu Phe Asp Gln Ala Phe Ser Glu Ser Val Ile
```

```
            275                 280                 285
Asp Ser Phe Asp Phe Asp Asn Pro Thr Lys Pro Glu Trp Tyr Cys Ile
    290                 295                 300

Glu Gly Gly Thr Ser Leu Leu Val Asp Ala Met Lys Glu Thr Leu Val
305                 310                 315                 320

His Lys Val Gln Asn Asn Lys Arg Val Asp Ala Ile Ser Ile Asp Leu
                325                 330                 335

Asp Ala Pro Asp Asp Gly Asn Met Ser Val Arg Ile Gly Gly Lys Asp
            340                 345                 350

His Ser Gly Tyr Ser Thr Val Phe Asn Thr Thr Ala Leu Gly Cys Leu
        355                 360                 365

Asp Arg Met Asp Leu Arg Gly Leu Asn Leu His Pro Thr Gln Ala Asp
370                 375                 380

Ala Ile Arg Cys Leu His Tyr Asp Asn Ser Thr Lys Val Ala Leu Lys
385                 390                 395                 400

Phe Ser Tyr Pro Trp Trp Ile Lys Asp Cys Gly Ile Thr Cys Gly Gly
                405                 410                 415

Ala Ala Ser Thr Asp Leu Pro Leu Arg Thr Cys Val Tyr Pro Ser Tyr
            420                 425                 430

Asn Leu Asp Asp Thr Gly Glu Ala Val Leu Leu Ala Ser Tyr Thr Trp
        435                 440                 445

Ser Gln Asp Ala Thr Arg Ile Gly Ser Leu Val Lys Asp Ala Pro Pro
    450                 455                 460

Gln Pro Pro Lys Glu Asp Glu Leu Val Glu Leu Ile Leu Gln Asn Leu
465                 470                 475                 480

Ala Arg Leu His Ala Glu His Met Thr Tyr Glu Lys Ile Lys Glu Ala
                485                 490                 495

Tyr Thr Gly Val Tyr His Ala Tyr Cys Trp Ala Asn Asp Pro Asn Val
            500                 505                 510

Gly Gly Ala Phe Ala Leu Phe Gly Pro Gly Gln Phe Ser Asn Leu Tyr
        515                 520                 525

Pro Tyr Leu Met Arg Pro Ala Ala Gly Gly Lys Phe His Ile Val Gly
    530                 535                 540

Glu Ala Ser Ser Val His His Ala Trp Ile Ile Gly Ser Leu Glu Ser
545                 550                 555                 560

Ala Tyr Thr Ala Val Tyr Gln Phe Leu Tyr Lys Tyr Lys Met Trp Asp
                565                 570                 575

Tyr Leu Arg Leu Leu Leu Glu Arg Trp Gln Tyr Gly Leu Gln Glu Leu
            580                 585                 590

Glu Thr Gly Lys His Gly Thr Ala His Leu Gln Phe Ile Leu Gly Ser
        595                 600                 605

Leu Pro Lys Glu Tyr Gln Val Lys Ile
    610                 615
```

(2) INFORMATION FOR SEQ ID NO:47:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:47:

CCCAGATCTA TATTTGCAAA CATGGACAAT G        31

(2) INFORMATION FOR SEQ ID NO:48:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:48:

```
GGGTCTAGAC TAACAAACAT CACACTTTCT ATG                              33
```

(2) INFORMATION FOR SEQ ID NO:49:

(i) SEQUENCE CHARACTERISTICS:
        (A) LENGTH: 415 base pairs
        (B) TYPE: nucleic acid
        (C) STRANDEDNESS: single
        (D) TOPOLOGY: linear (xi) SEQUENCE DESCRIPTION: SEQ ID NO:49:

```
TCTAGAGGAT CAGCATGGCG CCCACCGTGA TGATGGCCTC GTCGGCCACC GCCGTCGCTC   60
CGTTCCTGGG GCTCAAGTCC ACCGCCAGCC TCCCCGTCGC CCGCCGCTCC TCCAGAAGCC  120
TCGGCAACGT CAGCAACGGC GGAAGGATCC GGTGCATGCA GGTAACAAAT GCATCCTAGC  180
TAGTAGTTCT TTGCATTGCA GCAGCTGCAG CTAGCGAGTT AGTAATAGGA AGGGAACTGA  240
TGATCCATGC ATGGACTGAT GTGTGTTGCC CATCCCATCC CATCCCATTT CCCAAACGAA  300
CCGAAAACAC CGTACTACGT GCAGGTGTGG CCCTACGGCA ACAAGAAGTT CGAGACGCTG  360
TCGTACCTGC CGCCGCTGTC GACCGGCGGG CGCATCCGCT GCATGCAGGC CATGG       415
```

(2) INFORMATION FOR SEQ ID NO:50:

(i) SEQUENCE CHARACTERISTICS:
        (A) LENGTH: 1950 base pairs
        (B) TYPE: nucleic acid
        (C) STRANDEDNESS: single
        (D) TOPOLOGY: linear (xi) SEQUENCE DESCRIPTION: SEQ ID NO:50:

```
CCCGTTACTA CCATGGCTGC TATGGACAAT GTTGACTTTG CTGAATCTGT CCGAACCCGC   60
TGGGCGAGGC GACTCATTCG TGAGAAGGTC GCCAAGGAAC TCAACATTCT AACCGAAAGA  120
CTTGGTGAGG TGCCCGGCAT CCCTCCTCCA AATGAAGGCA GGTTCCTGGG CGGCGGCTAC  180
TCTCACGACA ATCTACCGTC TGATCCCCTC TATTCCAGCA TTAAGCCGGC TCTTCTAAAG  240
GAGGCTCCTC GAGCAGAAGA GGAACTGCCG CCTCGAAAGG TGTGCATCGT AGGCGCTGGT  300
GTTTCCGGCC TCTACATAGC CATGATTTTG GATGATTTGA AAATCCCAAA TCTCACTTAC  360
GACATCTTCG AATCCAGTTC CAGAACTGGT GGCCGTTTGT ATACGCACCA TTTCACCGAC  420
GCCAAGCATG ACTATTACGA CATTGGTGCT ATGCGATATC CTGACATCCC CAGCATGAAA  480
CGTACCTTTA ACCTGTTTAA ACGTACTGGG ATGCCTCTCA TCAAATATTA CCTTGATGGC  540
GAGAATACCC CTCAGCTGTA CAATAATCAC TTCTTCGCCA AGGGCGTGTC GGACCCCTAT  600
ATGGTGAGCG TGGCCAATGG CGGCACCGTG CCAGATGATG TTGTCGATAG TGTTGGAGAG  660
AAGTTACAAC AGGCTTTCGG TTATTACAAA GAGAAGCTTG CTGAGGACTT CGACAAAGGG  720
TTCGATGAGC TCATGCTCGT CGACGACATG ACCACTGAG AGTACTTGAA GCGAGGCGGG  780
CCGAAGGGAG AGGCGCCCAA GTATGACTTT TTCGCCATCC AGTGGATGGA GACACAAAAC  840
ACTGGGACAA ACCTGTTTGA TCAGGCCTTT TCTGAAAGCG TCATCGACTC GTTTGACTTT  900
GACAACCCGA CAAAGCCCGA ATGGTACTGC ATCGAGGGAG GAACATCGCT TTTGGTGGAC  960
```

```
GCCATGAAAG AAACCCTTGT CCACAAGGTA CAGAACAACA AGAGAGTTGA TGCCATTTCC    1020

ATTGACTTGG ACGCTCCGGA TGATGGGAAC ATGTCGGTCA GGATAGGCGG AAAGGATCAC    1080

TCCGGATATA GCACCGTCTT CAACACCACC GCTCTGGGCT GCCTTGACCG CATGGATCTG    1140

CGTGGTCTCA ACTTGCACCC TACTCAGGCA GATGCCATTC GATGTTTGCA CTATGACAAC    1200

TCGACCAAGG TGGCTCTCAA GTTTAGCTAC CCGTGGTGGA TCAAGGACTG TGGCATCACT    1260

TGCGGTGGCG CGGCCTCGAC TGATCTACCT CTACGAACTT GCGTTTACCC ATCATACAAC    1320

TTGGACGATA CTGGTGAGGC TGTTCTGCTT GCCTCATACA CTTGGTCTCA AGATGCAACT    1380

CGCATTGGAT CGTTGGTGAA GGACGCTCCA CCACAGCCGC CCAAGGAGGA TGAGCTTGTC    1440

GAGCTGATCC TGCAGAACCT AGCCCGCCTG CACGCTGAGC ATATGACCTA CGAGAAGATT    1500

AAGGAGGCTT ACACGGGCGT ATATCACGCC TATTGCTGGG CTAATGATCC CAATGTCGGT    1560

GGTGCTTTCG CCCTCTTCGG TCCCGGCCAG TTCAGCAATC TGTATCCATA CCTGATGCGG    1620

CCAGCGGCGG GCGGCAAGTT CCATATCGTC GGAGAGGCAT CTAGTGTGCA TCACGCCTGG    1680

ATCATAGGGT CTTTGGAGAG CGCTTACACC GCTGTGTACC AGTTCTTGTA CAAGTACAAG    1740

ATGTGGGATT ACTTGAGGTT GTTGTTGGAG CGCTGGCAGT ATGGTCTCCA GGAGTTAGAG    1800

ACGGGGAAGC ACGGTACGGC TCATTTGCAG TTTATTCTAG GTTCACTTCC CAAGGAGTAC    1860

CAGGTGAAGA TTTAAAGCGA AAGAGGTACT ACGGCATGGA GACAATTTTG GGTAGAGATT    1920

CTAGTATTCC AGCAGTTTCA TAATAATAAG                                    1950

(2) INFORMATION FOR SEQ ID NO:51:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:51:

CCCGTTACTA CCATGGCTGC TATGGACAAT GTTG                                 34

(2) INFORMATION FOR SEQ ID NO:52:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:52:

CTAACAAACA GAATTCTTAT TATTATGAAA CTGC                                 34

(2) INFORMATION FOR SEQ ID NO:53:

(i) SEQUENCE CHARACTERISTICS:
        (A) LENGTH: 193 base pairs
        (B) TYPE: nucleic acid
        (C) STRANDEDNESS: single
        (D) TOPOLOGY: linear (xi) SEQUENCE DESCRIPTION: SEQ ID NO:53:

TCTAGACCGG GCATGGCGTC CGCCGGGTC TTCTCGTCCA TCCTTCGCTC TGCCTCTCGC      60

ATTCGCTCCG CCTCACCGTC CCCATGCCCG CGTGCGCCGC TCCACCACCG CCCGTCCCCC    120

GCGGGCTTCA TACTCAACCG TGTAGCCGCC TACGCCTCCT CCGCCACGGC CCAGGCGGCA    180

CCTGCCATGG CGC                                                       193
```

(2) INFORMATION FOR SEQ ID NO:54:

(i) SEQUENCE CHARACTERISTICS:
        (A) LENGTH: 34 amino acids
        (B) TYPE: amino acid
        (C) STRANDEDNESS: Not Relevant
        (D) TOPOLOGY: linear (xi) SEQUENCE DESCRIPTION: SEQ ID NO:54:

```
Met Glu Asp Ala Ala Ala Arg Arg Met Arg Leu Ala Ser His Leu Arg
 1               5                  10                  15

Pro Pro Ala Ser Gln Met Glu Glu Ser Pro Leu Leu Arg Gly Ser Asn
            20                  25                  30

Cys Arg
```

(2) INFORMATION FOR SEQ ID NO:55:

(i) SEQUENCE CHARACTERISTICS:
        (A) LENGTH: 107 base pairs
        (B) TYPE: nucleic acid
        (C) STRANDEDNESS: single
        (D) TOPOLOGY: linear (xi) SEQUENCE DESCRIPTION: SEQ ID NO:55:

```
CCATGGAGGA CGCAGCAGCA AGGCGGATGG AGAGGCTCGC CTCCCACCTC CGCCCGCCCG      60

CTTCTCAGAT GGAGGAATCA CCCCTCCTGA GGGGCTCCAA TTGCCGG                  107
```

(2) INFORMATION FOR SEQ ID NO:56:

(i) SEQUENCE CHARACTERISTICS:
        (A) LENGTH: 617 amino acids
        (B) TYPE: amino acid
        (C) STRANDEDNESS: Not Relevant
        (D) TOPOLOGY: linear (xi) SEQUENCE DESCRIPTION: SEQ ID NO:56:

```
Met Asp Asn Val Asp Phe Ala Glu Ser Val Arg Thr Arg Trp Ala Arg
 1               5                  10                  15

Arg Leu Ile Arg Glu Lys Val Ala Lys Glu Leu Asn Ile Leu Thr Glu
            20                  25                  30

Arg Leu Gly Glu Val Pro Gly Ile Pro Pro Asn Glu Gly Arg Phe
        35                  40                  45

Leu Gly Gly Gly Tyr Ser His Asp Asn Leu Pro Ser Asp Pro Leu Tyr
    50                  55                  60

Ser Ser Ile Lys Pro Ala Leu Leu Gly Gly Gly Xaa Xaa Xaa Xaa
65                  70                  75                  80

Xaa Xaa Gly Gly Gly Gly Val Cys Ile Val Gly Ala Gly Val Ser Gly
            85                  90                  95

Leu Tyr Ile Ala Met Ile Leu Asp Asp Leu Lys Ile Pro Asn Leu Thr
                100                 105                 110

Tyr Asp Ile Phe Glu Ser Ser Ser Arg Thr Gly Arg Leu Tyr Thr
            115                 120                 125

His His Phe Thr Asp Ala Lys His Asp Tyr Tyr Asp Ile Gly Ala Met
        130                 135                 140

Arg Tyr Pro Asp Ile Pro Ser Met Lys Arg Thr Phe Asn Leu Phe Lys
145                 150                 155                 160

Arg Thr Gly Met Pro Leu Ile Lys Tyr Tyr Leu Asp Gly Glu Asn Thr
                165                 170                 175
```

-continued

```
Pro Gln Leu Tyr Asn Asn His Phe Phe Ala Lys Gly Val Ser Asp Pro
            180                 185                 190

Tyr Met Val Ser Val Ala Asn Gly Gly Thr Val Pro Asp Asp Val Val
            195                 200                 205

Asp Ser Val Gly Glu Lys Leu Gln Gln Ala Phe Gly Tyr Tyr Lys Glu
            210                 215                 220

Lys Leu Ala Glu Asp Phe Asp Lys Gly Phe Asp Glu Leu Met Leu Val
225                 230                 235                 240

Asp Asp Met Thr Thr Arg Glu Tyr Leu Lys Arg Gly Pro Lys Gly
                245                 250                 255

Glu Ala Pro Lys Tyr Asp Phe Phe Ala Ile Gln Trp Met Glu Thr Gln
            260                 265                 270

Asn Thr Gly Thr Asn Leu Phe Asp Gln Ala Phe Ser Glu Ser Val Ile
            275                 280                 285

Asp Ser Phe Asp Phe Asp Asn Pro Thr Lys Pro Glu Trp Tyr Cys Ile
            290                 295                 300

Glu Gly Gly Thr Ser Leu Leu Val Asp Ala Met Lys Glu Thr Leu Val
305                 310                 315                 320

His Lys Val Gln Asn Asn Lys Arg Val Asp Ala Ile Ser Ile Asp Leu
                325                 330                 335

Asp Ala Pro Asp Asp Gly Asn Met Ser Val Arg Ile Gly Gly Lys Asp
            340                 345                 350

His Ser Gly Tyr Ser Thr Val Phe Asn Thr Thr Ala Leu Gly Cys Leu
            355                 360                 365

Asp Arg Met Asp Leu Arg Gly Leu Asn Leu His Pro Thr Gln Ala Asp
            370                 375                 380

Ala Ile Arg Cys Leu His Tyr Asp Asn Ser Thr Lys Val Ala Leu Lys
385                 390                 395                 400

Phe Ser Tyr Pro Trp Trp Ile Lys Asp Cys Gly Ile Thr Cys Gly Gly
            405                 410                 415

Ala Ala Ser Thr Asp Leu Pro Leu Arg Thr Cys Val Tyr Pro Ser Tyr
            420                 425                 430

Asn Leu Asp Asp Thr Gly Glu Ala Val Leu Leu Ala Ser Tyr Thr Trp
            435                 440                 445

Ser Gln Asp Ala Thr Arg Ile Gly Ser Leu Val Lys Asp Ala Pro Pro
            450                 455                 460

Gln Pro Pro Lys Glu Asp Glu Leu Val Glu Leu Ile Leu Gln Asn Leu
465                 470                 475                 480

Ala Arg Leu His Ala Glu His Met Thr Tyr Glu Lys Ile Lys Glu Ala
                485                 490                 495

Tyr Thr Gly Val Tyr His Ala Tyr Cys Trp Ala Asn Asp Pro Asn Val
            500                 505                 510

Gly Gly Ala Phe Ala Leu Phe Gly Pro Gly Gln Phe Ser Asn Leu Tyr
            515                 520                 525

Pro Tyr Leu Met Arg Pro Ala Ala Gly Gly Lys Phe His Ile Val Gly
            530                 535                 540

Glu Ala Ser Ser Val His His Ala Trp Ile Ile Gly Ser Leu Glu Ser
545                 550                 555                 560

Ala Tyr Thr Ala Val Tyr Gln Phe Leu Tyr Lys Tyr Lys Met Trp Asp
                565                 570                 575

Tyr Leu Arg Leu Leu Leu Glu Arg Trp Gln Tyr Gly Leu Gln Glu Leu
            580                 585                 590

Glu Thr Gly Lys His Gly Thr Ala His Leu Gln Phe Ile Leu Gly Ser
```

```
                    595                 600                 605
Leu Pro Lys Glu Tyr Gln Val Lys Ile
    610                 615

(2) INFORMATION FOR SEQ ID NO:57:

(i) SEQUENCE CHARACTERISTICS:
        (A) LENGTH: 617 amino acids
        (B) TYPE: amino acid
        (C) STRANDEDNESS: Not Relevant
        (D) TOPOLOGY: linear (xi) SEQUENCE DESCRIPTION: SEQ ID NO:57:

Met Asp Asn Val Asp Phe Ala Glu Ser Val Arg Thr Arg Trp Ala Arg
1               5                   10                  15

Arg Leu Ile Arg Glu Lys Val Ala Lys Glu Leu Asn Ile Leu Thr Glu
            20                  25                  30

Arg Leu Gly Glu Val Pro Gly Ile Pro Pro Asn Glu Gly Arg Phe
        35                  40                  45

Leu Gly Gly Gly Tyr Ser His Asp Asn Leu Pro Ser Asp Pro Leu Tyr
    50                  55                  60

Ser Ser Ile Gly Gly Gly Ser Gly Gly Xaa Xaa Xaa Xaa Xaa Gly
65              70                  75                  80

Gly Gly Pro Pro Arg Lys Val Cys Ile Val Gly Ala Gly Val Ser Gly
                85                  90                  95

Leu Tyr Ile Ala Met Ile Leu Asp Asp Leu Lys Ile Pro Asn Leu Thr
            100                 105                 110

Tyr Asp Ile Phe Glu Ser Ser Arg Thr Gly Gly Arg Leu Tyr Thr
        115                 120                 125

His His Phe Thr Asp Ala Lys His Asp Tyr Tyr Asp Ile Gly Ala Met
    130                 135                 140

Arg Tyr Pro Asp Ile Pro Ser Met Lys Arg Thr Phe Asn Leu Phe Lys
145                 150                 155                 160

Arg Thr Gly Met Pro Leu Ile Lys Tyr Tyr Leu Asp Gly Glu Asn Thr
                165                 170                 175

Pro Gln Leu Tyr Asn Asn His Phe Phe Ala Lys Gly Val Ser Asp Pro
            180                 185                 190

Tyr Met Val Ser Val Ala Asn Gly Gly Thr Val Pro Asp Asp Val Val
        195                 200                 205

Asp Ser Val Gly Glu Lys Leu Gln Gln Ala Phe Gly Tyr Tyr Lys Glu
    210                 215                 220

Lys Leu Ala Glu Asp Phe Asp Lys Gly Phe Asp Glu Leu Met Leu Val
225                 230                 235                 240

Asp Asp Met Thr Thr Arg Glu Tyr Leu Lys Arg Gly Gly Pro Lys Gly
                245                 250                 255

Glu Ala Pro Lys Tyr Asp Phe Phe Ala Ile Gln Trp Met Glu Thr Gln
            260                 265                 270

Asn Thr Gly Thr Asn Leu Phe Asp Gln Ala Phe Ser Glu Ser Val Ile
        275                 280                 285

Asp Ser Phe Asp Phe Asp Asn Pro Thr Lys Pro Glu Trp Tyr Cys Ile
    290                 295                 300

Glu Gly Gly Thr Ser Leu Leu Val Asp Ala Met Lys Glu Thr Leu Val
305                 310                 315                 320

His Lys Val Gln Asn Asn Lys Arg Val Asp Ala Ile Ser Ile Asp Leu
                325                 330                 335
```

```
Asp Ala Pro Asp Asp Gly Asn Met Ser Val Arg Ile Gly Gly Lys Asp
            340                 345                 350

His Ser Gly Tyr Ser Thr Val Phe Asn Thr Thr Ala Leu Gly Cys Leu
            355                 360                 365

Asp Arg Met Asp Leu Arg Gly Leu Asn Leu His Pro Thr Gln Ala Asp
            370                 375             380

Ala Ile Arg Cys Leu His Tyr Asp Asn Ser Thr Lys Val Ala Leu Lys
385                 390                 395                 400

Phe Ser Tyr Pro Trp Trp Ile Lys Asp Cys Gly Ile Thr Cys Gly Gly
                405                 410                 415

Ala Ala Ser Thr Asp Leu Pro Leu Arg Thr Cys Val Tyr Pro Ser Tyr
            420                 425                 430

Asn Leu Asp Asp Thr Gly Glu Ala Val Leu Leu Ala Ser Tyr Thr Trp
            435                 440                 445

Ser Gln Asp Ala Thr Arg Ile Gly Ser Leu Val Lys Asp Ala Pro Pro
            450                 455                 460

Gln Pro Pro Lys Glu Asp Glu Leu Val Glu Leu Ile Leu Gln Asn Leu
465                 470                 475                 480

Ala Arg Leu His Ala Glu His Met Thr Tyr Glu Lys Ile Lys Glu Ala
                485                 490                 495

Tyr Thr Gly Val Tyr His Ala Tyr Cys Trp Ala Asn Asp Pro Asn Val
                500                 505                 510

Gly Gly Ala Phe Ala Leu Phe Gly Pro Gly Gln Phe Ser Asn Leu Tyr
            515                 520                 525

Pro Tyr Leu Met Arg Pro Ala Ala Gly Gly Lys Phe His Ile Val Gly
            530                 535                 540

Glu Ala Ser Ser Val His His Ala Trp Ile Ile Gly Ser Leu Glu Ser
545                 550                 555                 560

Ala Tyr Thr Ala Val Tyr Gln Phe Leu Tyr Lys Tyr Lys Met Trp Asp
                565                 570                 575

Tyr Leu Arg Leu Leu Leu Glu Arg Trp Gln Tyr Gly Leu Gln Glu Leu
            580                 585                 590

Glu Thr Gly Lys His Gly Thr Ala His Leu Gln Phe Ile Leu Gly Ser
            595                 600                 605

Leu Pro Lys Glu Tyr Gln Val Lys Ile
            610                 615

(2) INFORMATION FOR SEQ ID NO:58:

(i) SEQUENCE CHARACTERISTICS:
        (A) LENGTH: 617 amino acids
        (B) TYPE: amino acid
        (C) STRANDEDNESS: Not Relevant
        (D) TOPOLOGY: linear (xi) SEQUENCE DESCRIPTION: SEQ ID NO:58:

Met Asp Asn Val Asp Phe Ala Glu Ser Val Arg Thr Arg Trp Ala Arg
1               5                   10                  15

Arg Leu Ile Arg Glu Lys Val Ala Lys Glu Leu Asn Ile Leu Thr Glu
            20                  25                  30

Arg Leu Gly Glu Val Pro Gly Ile Pro Pro Asn Glu Gly Arg Phe
            35                  40                  45

Leu Gly Gly Gly Tyr Ser His Asp Asn Leu Pro Ser Asp Pro Leu Tyr
            50                  55                  60

Ser Ser Ile Lys Pro Gly Gly Gly Xaa Xaa Xaa Xaa Xaa Gly
65                  70                  75                  80
```

```
Gly Gly Pro Pro Arg Lys Val Cys Ile Val Gly Ala Gly Val Ser Gly
             85                  90                  95
Leu Tyr Ile Ala Met Ile Leu Asp Asp Leu Lys Ile Pro Asn Leu Thr
            100                 105                 110
Tyr Asp Ile Phe Glu Ser Ser Arg Thr Gly Gly Arg Leu Tyr Thr
        115                 120                 125
His His Phe Thr Asp Ala Lys His Asp Tyr Tyr Asp Ile Gly Ala Met
        130                 135                 140
Arg Tyr Pro Asp Ile Pro Ser Met Lys Arg Thr Phe Asn Leu Phe Lys
145                 150                 155                 160
Arg Thr Gly Met Pro Leu Ile Lys Tyr Tyr Leu Asp Gly Glu Asn Thr
                165                 170                 175
Pro Gln Leu Tyr Asn Asn His Phe Phe Ala Lys Gly Val Ser Asp Pro
            180                 185                 190
Tyr Met Val Ser Val Ala Asn Gly Gly Thr Val Pro Asp Asp Val Val
            195                 200                 205
Asp Ser Val Gly Glu Lys Leu Gln Gln Ala Phe Gly Tyr Tyr Lys Glu
            210                 215                 220
Lys Leu Ala Glu Asp Phe Asp Lys Gly Phe Asp Glu Leu Met Leu Val
225                 230                 235                 240
Asp Asp Met Thr Thr Arg Glu Tyr Leu Lys Arg Gly Gly Pro Lys Gly
                245                 250                 255
Glu Ala Pro Lys Tyr Asp Phe Phe Ala Ile Gln Trp Met Glu Thr Gln
                260                 265                 270
Asn Thr Gly Thr Asn Leu Phe Asp Gln Ala Phe Ser Glu Ser Val Ile
            275                 280                 285
Asp Ser Phe Asp Phe Asp Asn Pro Thr Lys Pro Glu Trp Tyr Cys Ile
        290                 295                 300
Glu Gly Gly Thr Ser Leu Leu Val Asp Ala Met Lys Glu Thr Leu Val
305                 310                 315                 320
His Lys Val Gln Asn Asn Lys Arg Val Asp Ala Ile Ser Ile Asp Leu
                325                 330                 335
Asp Ala Pro Asp Asp Gly Asn Met Ser Val Arg Ile Gly Gly Lys Asp
            340                 345                 350
His Ser Gly Tyr Ser Thr Val Phe Asn Thr Thr Ala Leu Gly Cys Leu
            355                 360                 365
Asp Arg Met Asp Leu Arg Gly Leu Asn Leu His Pro Thr Gln Ala Asp
        370                 375                 380
Ala Ile Arg Cys Leu His Tyr Asp Asn Ser Thr Lys Val Ala Leu Lys
385                 390                 395                 400
Phe Ser Tyr Pro Trp Trp Ile Lys Asp Cys Gly Ile Thr Cys Gly Gly
                405                 410                 415
Ala Ala Ser Thr Asp Leu Pro Leu Arg Thr Cys Val Tyr Pro Ser Tyr
            420                 425                 430
Asn Leu Asp Asp Thr Gly Glu Ala Val Leu Leu Ala Ser Tyr Thr Trp
        435                 440                 445
Ser Gln Asp Ala Thr Arg Ile Gly Ser Leu Val Lys Asp Ala Pro Pro
        450                 455                 460
Gln Pro Pro Lys Glu Asp Glu Leu Val Glu Leu Ile Leu Gln Asn Leu
465                 470                 475                 480
Ala Arg Leu His Ala Glu His Met Thr Tyr Glu Lys Ile Lys Glu Ala
                485                 490                 495
```

-continued

```
Tyr Thr Gly Val Tyr His Ala Tyr Cys Trp Ala Asn Asp Pro Asn Val
            500             505             510

Gly Gly Ala Phe Ala Leu Phe Gly Pro Gly Gln Phe Ser Asn Leu Tyr
            515             520             525

Pro Tyr Leu Met Arg Pro Ala Ala Gly Gly Lys Phe His Ile Val Gly
        530             535             540

Glu Ala Ser Ser Val His His Ala Trp Ile Ile Gly Ser Leu Glu Ser
545             550             555             560

Ala Tyr Thr Ala Val Tyr Gln Phe Leu Tyr Lys Tyr Lys Met Trp Asp
                565             570             575

Tyr Leu Arg Leu Leu Leu Glu Arg Trp Gln Tyr Gly Leu Gln Glu Leu
            580             585             590

Glu Thr Gly Lys His Gly Thr Ala His Leu Gln Phe Ile Leu Gly Ser
        595             600             605

Leu Pro Lys Glu Tyr Gln Val Lys Ile
    610             615
```

METHODS AND COMPOSITIONS FOR CONTROLLING INSECTS

CROSS-REFERENCE TO RELATED APPLICATIONS

This application claims the benefit of U.S. Provisional Application Ser. No. 60/044,504, filed Apr. 21, 1997.

FIELD OF THE INVENTION

This invention relates to compositions and methods for controlling coleopteran insects by use of two proteins in combination which may be applied directly to the plant or produced thereon by microorganisms or by genetically modifying the plant to produce the proteins, to genes encoding these proteins, to methods for identifying such genes and proteins, and to recombinant microorganisms and plants capable of expressing these genes for use in controlling plant infestation by the target coleopteran insects.

BACKGROUND OF THE INVENTION

The control of insect pests by naturally occurring proteins is a well established practice. The most commonly used insect control proteins are the endotoxins derived from *Bacillus thuringiensis* (B.t.) that are used to control both lepidopteran and coleopteran insect pests. Expression of these proteins in transgenic plants also confers protection against certain insect pests (Barton et al., 1987; Fischhoff et al., 1987 Perlak et al., 1990; Vaeck et al., 1987).

A variety of insect pests that cause significant economic losses were not previously known to be controlled by B.t. endotoxins. Boll weevil (BWV), *Anthonomus grandis*, corn rootworm (CRW), Diabrotica spp., and wireworm (WW), Melanotus spp. are examples of coleopteran insect pests that inflict significant crop damage yet, until recently were not known to be controlled by known B.t. endotoxins. Thus, it would be useful to identify new insecticidal proteins which, alone or in combination, are able to control these coleopteran insects. Furthermore, it would be useful to identify new insecticidal proteins with different modes of action to delay the development of B.t. endotoxin resistance in coleopteran pests such as the Colorado potato beetle (CPB), *Leptinotarsa decemlineata* (Say), that are currently controlled by certain B.t. endotoxins (Krieg et al., 1983).

Preparations of enzymes from several different sources are available from Sigma Chemical Company (St. Louis, Mo.) and other suppliers. Amino acid oxidases can also be obtained from sources including, but not limited to snake venom, mammalian, and avian sources (Bright and Porter, 1975). Lysine and other amino acid oxidases (E.C. 1.4.3.2) are naturally produced by micro-organisms such as Trichoderma sp., Neurospora sp., Penicillium sp., and Proteus sp. (Kusakabe et al., 1979; 1980; Niederman and Lerch, 1990; Knight, 1948; Stumpf and Green, 1944). Although lysine oxidase has been shown to have antitumor activity (Kusakabe et al., 1979; Id., 1980), there have been no reports of insecticidal activity associated with this enzyme. Also, there have been no reports of insecticidal activity being associated with an amino acid oxidase enzyme when combined with any other compound. However, we have unexpectedly found that a composition comprising a lysine oxidase and a previously unidentified $M_r$ 50,000 protein yield potent insecticidal activity when combined in a mixture and ingested by an insect. The $M_r$ 50,000 protein is described herein as a tedanalactam synthase shown herein to have at least one enzyme activity in which Δ1-piperideine- 2-carboxylate is converted to tedanalactam. Described herein are methods for using a combination of lysine oxidase and tedanalactam synthase to control infestation of plants by insect pests.

SUMMARY OF THE INVENTION

This invention relates generally to novel compositions and methods for the control of undesired insects. It is therefore a particular object of the present invention to present materials and methods used in the preparation of compositions and plants capable of controlling insect infestation when ingested by the insect. It is also an object of the present invention to provide protein compositions capable of controlling BWV, CRW, WW, CPB or other insect pests, and genes useful in producing such proteins. It is a further object of the present invention to provide genetic constructs for and methods of inserting such genetic material into microorganisms and plant cells. It is another object of the present invention to provide transformed microorganisms and plants containing such genetic material. Still another object of this invention relates to methods and reagents such as polynucleotides and antibodies, and the use of such methods and reagents in kit form, for detecting the individual molecules which comprise the active compositions as noted herein. In addition, variants of the molecules which comprise the active compositions are also contemplated by this invention.

Among the several advantages found to be achieved by the present invention, therefore, may be noted the provision of a composition containing at least two proteins, lysine oxidase enzyme and tedanalactam synthase enzyme, which is capable of controlling insects, particularly coleopteran insects. These two proteins cause mortality and stunting of larvae of coleopteran insects when co-ingested. The proteins may be applied directly to plants or introduced in other ways such as through the application of plant-colonizing microorganisms or by transformed plants generated using recombinant DNA methods wherein the recombinant plants express genes encoding these enzymes.

In accomplishing the foregoing, there is provided, in accordance with one aspect of the present invention, a method of controlling insect infestation of plants comprising providing a composition containing at least a lysine or amino acid oxidase along with a second enzyme, which is preferably a tedanalactam synthase, for ingestion by the insect. It is apparent that neither protein alone is able to confer any insecticidal activity. However, it is the combination of the amino acid oxidase along with the second enzyme which is effective in confering insecticidal activity upon ingestion of such a composition by an insect. The composition, upon ingestion by the insect, contains a sufficient insecticidal amount of the proteins, such that the insect is unable to survive or is rendered incapable of causing further damage to a plant to which the composition has been applied. The composition contains a first enzyme which is a lysine oxidase enzyme, and a second enzyme which is capable of converting Δ1-piperideine-2-carboxylate to tedanalactam. The proteins in the composition are preferably isolated from extracts of fungal species fermentations in which the extracts have been shown to exhibit insecticidal activity. The fungal species herein which produces an insecticidally effective extract composition was determined to be a Trichoderma species of fungi, and in particular a *Trichoderma viride.* Another Monsanto Company fungal isolate was designated as Trichoderma sp. F22844 also produces an insecticidally effective extract composition. The genes encoding the proteins in the illustrative composition are therefore preferably isolated from a Trichoderma species of fungi, however, other uncharacterized fungal species are believed to contain at least a lysine oxidase gene and a second protein which, in combination provide efficacious insecticidal activity.

The composition can contain as the second enzyme a protein which is approximately 50,000 Da, which is also recognized by one skilled in the art as a protein or enzyme which is approximately $M_r$ 50,000. It is believed that the second enzyme can be isolated from any number of species, however it is preferably isolated from a species which produces compounds which exhibit coleopteran insecticidal activity, and more preferably isolated from a fungal species. It is also believed that any fungal species which exhibits coleopteran insecticidal activity and also produces a lysine oxidase may also produce a second enzyme which in combination with the lysine oxidase confers effective insecticidal activity when ingested by target insect. Furthermore, any species which produces a lysine oxidase and which also contains a gene which hybridizes under stringent conditions to a Trichoderma species gene encoding an approximately $M_r$ 50,000 Da protein which converts Δ1-piperideine-2-carboxylate to tedanalactam may confer effective insecticidal activity when a composition containing both enzymes is ingested by a target insect. The property of converting Δ1-piperideine-2-carboxylate to tedanalactam may be independent of the property which, in combination with an amino acid oxidase confers insecticidal activity upon the composition when ingested by the insect. It is intended that the composition not be limited to a combination of an amino acid oxidase and a tedanalactam synthase, but conceivably could also include the combination of a gene encoding an amino acid oxidase and a gene encoding a tedanalactam synthase, together with all necessary genetic regulatory elements required for expression, including repression and activation, transcription and translation, and post-transcriptional and post-translational modification signals incorporated therein. The genes as described could also be present either alone or in combination with each other on a single replicon.

The composition which confers coleopteran insecticidal activity is directed preferably to coleopteran species selected from the group consisting of Diabrotica species, Melanotus species, Leptinotarsa species, and Anthonomus species. Moreover, the composition is directed to controlling insects selected from the group consisting of boll weevil (BWV), corn rootworm (CRW), corn wireworm (WW), and the Colorado potato beetle (CPB).

The compositions in particular can contain the indicated enzymes in a mixture in which the molar ratios of the two enzymes are generally such that effective insect control is manifested. Insect control can be effected when the amino acid oxidase and the tedanalactam synthase are present within the composition in molar ratios of about 100:1 to about 1:1 respectively, or when the ratios are about 10:1 to about 1:1, respectively, or when the ratios of the two proteins are present from about 1:10 to about 1:1, or when the ratios of the two proteins are present from about 1:100 to about 1:1, respectively. In addition, effective concentrations of these proteins in a composition in which the proteins are each present from about one part per million to about 10 parts per million are effective in conferring insecticidal activity and control. The most effective insecticidal is activity is conferred when the proteins are each present in a composition from about one part per million to about 20 parts per million.

Another aspect of the present invention provides the structural genes which encode the enzymes which are the active components in the insecticidal compositions. Briefly, the genes can be isolated from genomic DNA and from cDNA molecules which are obtained by isolating MRNA from species which are shown to produce these enzymes. The structural genes encoding these enzymes, which may also be isolated as proenzymes or precursor proteins, preferably are identified by first isolating the active components or enzymes from extracts of organisms which produce these enzymes. Isolated enzymes can be digested with proteolytic enzymes, and amino acid sequences of proteolytic peptide fragments can be characterized. Redundant nucleotide probes corresponding to the characterized peptide fragments can be produced based on the deduced amino acid sequences, and used as probes or primers for identifying or amplifying particular segments of mRNA, cDNA, or genomic polynucleotides. Full length MRNA, full length CDNA, and uninterrupted full length genes can be further identified and isolated.

In accordance with other aspects of the present invention, there are provided methods and compositions for producing genetically transformed plants which express an amount of a lysine or other amino acid oxidase along with a second enzyme or tedanalactam synthase effective to control coleopteran insects. Recombinant plasmids have been produced which contain regulatory elements which function in plants for producing messenger RNA molecules, from which the proteins of the present invention are translated. Expression cassettes are disclosed which contain various elements alone or in combination for enabling the production of the amino acid oxidase or the tedanalactam synthase. Specifically, the amino acid oxidase gene is provided in a cassette comprising a polynucleotide sequence flanked 5' by a promoter which functions in plants to cause the production of an RNA sequence is operably linked to an intron and a DNA sequence which functions in plants as a targeting signal or transit peptide and flanked 3' by a DNA sequence which functions in plants to cause the addition of a 3' non-translated polyadenylated nucleotide sequence to the 3' end of the RNA is fused 3' to the amino acid oxidase gene so that the expression of the cassette is under the control of the promoter. There are numerous alternatives to this construction, some of which are provided herein in specific examples. For example, the intron and targeting sequence can be replaced by a 5' non-translated leader sequence; or the non-translated leader can be removed; the intron can be inserted between the non-translated leader and the oxidase gene or between the leader and the targeting sequence. The tedanalactam synthase can be assembled in a similar fashion, and specific examples are provided herein. An expression cassette for producing an amino acid oxidase can be combined into a single vector along with a cassette for producing a tedanalactam synthase so that delivery of both cassettes for simultaneous expression either in a plant or other organism such as a bacterium or fungi is also contemplated. Also, in a plant it is possible to express one of the cassettes in one tissue type, for example in roots, and express the other cassette in another tissue type, for example in leaves. It may also be possible to produce the proteins separately temporally or spatially, but in the same tissue type. For example, expression of one cassette in young leaves and the other cassette later in the same leaves is contemplated, however co-expression is normally desirable. The expression cassette can be designed to function in plants by using plant specific regulatory elements such as promoters, introns, targeting sequences, non-translated leaders, and 3' polyadenylation sequences. The expression cassette can also be designed to function in prokaryotic systems as contemplated and described herein, also by using prokaryotic specific regulatory elements. The cassettes described herein can be inserted into plants by high velocity DNA coated particle projectile bombardment, by naked DNA protoplast transformation, or by bacterial mediated methods known in the art.

In describing this particular embodiment of the invention, it should be understood that expression of the amino acid oxidase, which can also be a precursor or proenzyme, and tedanalactam synthase can be controlled by two independent promoters from two separate and independent transcriptional units. It should also be understood that a single promoter could be used to drive expression of a single transcription unit containing an in frame translational fusion of both proteins. The hybrid polyprotein could then be post-translationally cleaved to yield both proteins by previously described schemes (Halpin and Ryan, WO 95/17514). Another advantage achieved by the present invention provides a peptide fusion to be produced from the genes encoding the two enzymes wherein the coding sequences of the two genes are fused in frame to allow for the expression of a recombinant gene encoding an in-frame translational peptide fusion of the amino acid oxidase and the tedanalactam synthase. The fusion can be one in which either enzyme is amino terminal with respect to the other. The fusion can be post-translationally cleaved by a plant endogenous endoprotease to produce an insecticidally active composition in the plant tissues so that lysine oxidase and tedanalactam synthase are present as separate and individual molecules. Alternatively, the fusion can be post-translationally cleaved by an endogenous insect endoprotease, generally found within the midgut of contemplated insect targets, so that the cleavage of the fusion protein produces an insecticidally active composition while within the midgut of the feeding insect.

In keeping with this aspect of the present invention, is the provision for a variety of promoters for transcriptional initiation and expression of the contemplated genes, in particular in plants. A number of promoters which are active in plant cells have been described in the literature. Such promoters may be obtained from plants or plant viruses and include, but are not limited to the nopaline synthase (NOS) and octopine synthase (OCS) promoters, which are carried on tumor-inducing plasmids generally found within virulent and non-virulent strains of *Agrobacterium tumefaciens,* the cauliflower mosaic virus (CaMV) 19S and 35S promoters, the light-inducible ribulose 1,5-bisphosphate carboxylase small subunit promoter(ssRUBISCO), and the Figwort Mosaic Virus 35S promoter (FMV). All of these promoters have been used to create various types of DNA constructs which have been expressed in plants (see for example Barry et al. U.S. Pat. No. 5,463,175, which is herein incorporated by reference). Particularly desirable promoters which are contemplated because of their constitutive nature are the Cauliflower Mosaic Virus 35S (CaMV35S) and the Figwort Mosaic Virus 35S (FMV35S) promoters which have previously been shown to produce high levels of expression in most plant organs. Other preferred promoters are root enhanced or root tissue specific promoters such as the Cauliflower Mosaic Virus derived AS4 promoter (also designated as the 4x as-1 or the 4as-1 promoter), the tobacco RB7 promoter, or the rice RC2 promoter (Lam et al., 1991; Yamamoto et al., 1991; Xu et al., 1995). The root enhanced or root tissue specific promoters would be particularly preferred for the control of corn rootworm (Diabrotica spp.) in transgenic corn plants. Other promoters are also contemplated which would direct tissue specific targeted expression are also contemplated, for example in tissue such as leaves, meristem, flower, fruit and organs of reproductive character. IN addition, chimeric promoters are also envisioned.

Other expression regulatory elements are considered to be of importance, especially in contemplation of transformed plant tissue or transformed plant cell expression. These elements comprise at least non-translated sequences and introns. For example, transcriptional events leading to RNA production from the contemplated DNA constructs as set forth herein could contain 5' non-translated leader sequences. These sequences can be derived from new or existing promoters which are selected for gene expression, and can be specifically modified so as to increase translational efficiency of the mRNA. A plant gene leader sequence which has been shown to be particularly useful in the present invention is the petunia heat shock protein 70 leader (hsp70) (Winter et al., 1988). It has also been shown that introns are preferred for optimum expression in monocotyledenous plants. Any number of introns could function for this purpose, and without intending any limitation these could be selected from the group consisting of the maize hsp70 intron and the rice actin intron. Another nontranslated regulatory element of particular importance in plant systems are DNA sequences which function in plants to cause the addition of a 3' non-translated polyadenylated nucleotide sequence to the 3' end of an RNA sequence produced as a result of transcription from an indicated promoter sequence. These particular non-translated sequences are also commonly known as polyadenylation sequences or signals.

A further embodiment provides for the targeted delivery of a gene product to a particular organellar compartment, such as a vacuole, a mitochondrion, a chloroplast, a plastid, an endoplasmic reticulum compartment, a Golgi compartment, or even the nuclear or nucleolar domains. Particular peptide sequences have been shown to be necessary in obtaining efficient delivery of protein products to these sites, in particular signal peptides, signal sequences, and targeting sequences. Targeting signals or transit peptides contemplated herein, without intending to be limited to these, can be selected from the group consisting of a rice malate dehydrogenase amino terminal peroxisomal targeting signal and a maize ATP synthase beta subunit mitochondrial transit peptide.

A further embodiment of the present invention provides for the insertion of one or more of the contemplated expression cassettes along with any expression regulatory elements into the genome of a plant cell to form a stable recombinant plant cell. In one embodiment the DNA inserted into the plant genome would be comprised of a single cassette encoding a fusion peptide formed from the gene fusions described above, along with regulatory elements necessary for expression of the gene fusion. In another embodiment, the DNA inserted into the genome would be comprised of a single cassette encoding only an amino acid oxidase or a tedanalactam synthase, along with any regulatory elements necessary for expression of the gene. In the preferred embodiment, the DNA inserted into the plant genome would be comprised of a first gene cassette encoding an amino acid oxidase in which expression was controlled by a first promoter, and a second gene cassette encoding a tedanalactam synthase in which expression was controlled by a second promoter, along with any other necessary regulatory elements for expression of either gene. This embodiment contemplates that the first and the second promoters can be identical in sequence and function, or they can be different from each other, so long as each gene is expressed in an amount which provides a composition for controlling insect infestation of plants comprising a mixture of the enzymes when the mixture is ingested by a susceptible insect.

A further embodiment of the present invention provides methods for generating plants which express an insecticidally effective amount of a lysine or amino acid oxidase or proenzyme along with a tedanalactam synthase. The methods utilize contemplated DAN expression cassettes designed for producing either or both enzymes separately or in combination inserted into plasmids. The plasmid DNAs can be directly inserted into the genome of a plant by mechanical approaches, such as biolistic methods or by protoplast fusion techniques. A preferred method utilizes Agrobacterium mediated double border plant transformation, preferably using a DNA vector containing the desired expression cassette or cassettes flanked by Ti plasmid border recombination sequences in order to introduce the desired genes into the plant genome. The transformation procedure generally produces events which provides transformed plant cells selected on solid or in liquid media using any number of selectable markers known in the art, preferably glyphosate selectable markers such as GOX or EPSPS, antibiotic selectable markers, or others. Transformed cells obtained using these methods can be further regenerated to produce stably transformed genetically engineered plants which express insecticidally effective amounts of the amino acid oxidase or the tedanalactam synthase.

There is also provided, in accordance with another aspect of the present invention, transformed bacterial and plant cells that contain DNA comprised of the expressible gene cassettes as described above, along with appropriate control sequences necessary to provide for desired and appropriate expression of the coding sequences, producing insecticidally effective amounts of the enzymes. The control sequences can be any known in the art to function in a particular cell or organelle type. It is contemplated that the genes herein can be expressed in bacterial systems, plant nucleolar compartments, plant nuclear compartments, and in plant mitochondrial and chloroplast compartments.

While particular examples of using the invention described herein to control corn rootworm in corn or Colorado potato beetle in potato are provided, it is understood that the methods of this invention could be applied to provide insect protection, and more preferably coleopteran insect protection, to plant species from the genera Fabaceae, Medicago, Trifolium, Vigna, Daucus, Arabidopsis, Brassica, Raphanus, Sinapis, Lycopersicon, Capsicum, Solanum, Nicotiana, Helianthus, Bromus, Asparagus, Panicum, Pennisetum, Cucumis, Lolium, Glycine, Triticum, Gossypium and Zea. In addition, forestry crop species from the genera Pinus, Populus, Eucalyptus, Acacia, Silex, and Larix are also prone to important coleopteran pest infestation which may be controlled by the methods and compositions described herein. Also, turf grass species such as St. Augustine (*Stenotaphrum secundatum*), Kentucky blue grass (*Poa pratensis*), and creeping bentgrass (*Agrostis stolonifera*) among others are susceptible to coleopteran pests such as white grub and the like which may also be controlled by the present invention. Insect pests which infest Roses (Rosa) and perennials such as Begonia, Pelagonium, Imaptiens, Tagetes, Viola, Petunia and Catharanthus and the like may also be subjects of the present invention.

FIGURE LEGENDS

FIG. 1 represents a plasmid map of pMON25061 which is a plant transformation vector containing a neomycin phosphotransferase selectable marker under the control of a cauliflower mosaic virus 35S promoter; and a tedanalactam synthase gene and lysine oxidase gene each under the control of separate root enhanced 4AS1 promoters.

FIG. 2 represents a plasmid map of pMON25049 which is an Agrobacterium mediated double border plant transformation vector containing a neomycin phosphotransferase selectable marker under the control of a cauliflower mosaic virus 35S promoter; a lysine oxidase gene fused to a petunia hsp70 leader sequence under the control of a figwort mosaic virus promoter; and a tedanalactam synthase gene fused to a petunia hsp70 leader sequence under the control of a figwort mosaic virus promoter.

Figure 28:
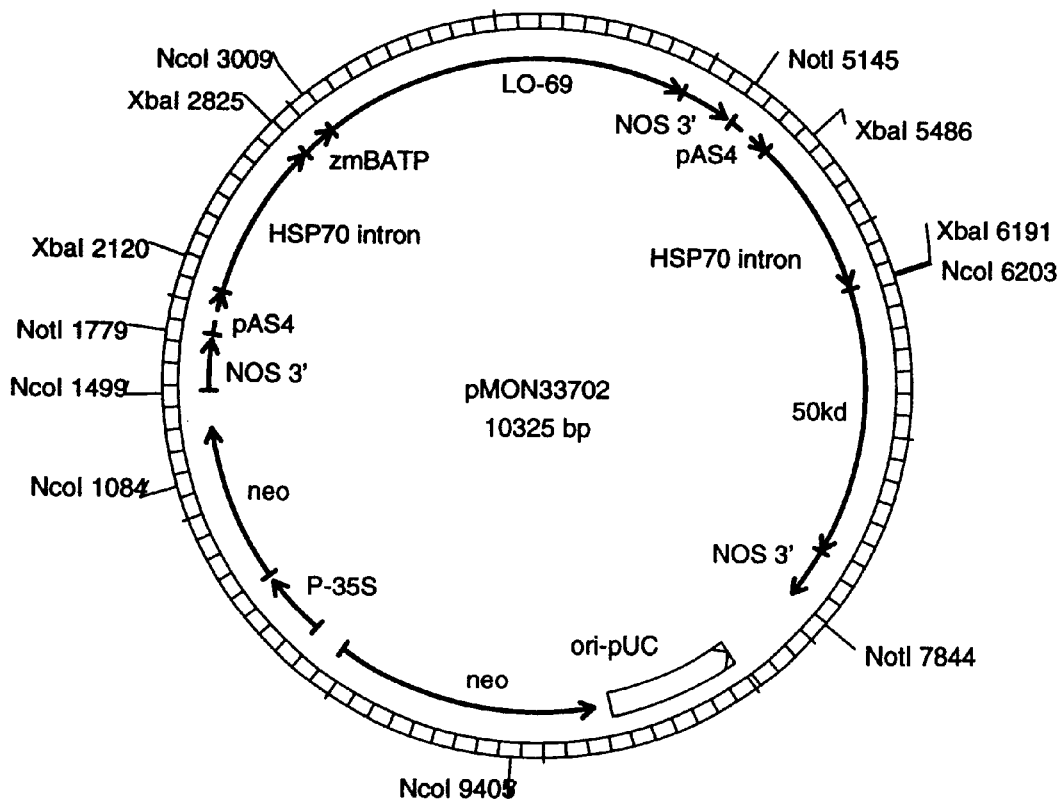

FIG. 28 represents a plasmid map of pMON33702 which is a plant transformation vector containing a neomycin phosphotransferase gene under the control of a cauliflower mosaic virus 35S promoter; a lysine oxidase gene fused to a sequence encoding a maize ATP synthase beta subunit mitochondrial transit peptide, which is fused to an hsp70 intron sequence under the control of a root tissue enhanced promoter; and a tedanalactam synthase gene fused to an hsp70 intron sequence under the control of a root tissue enhanced promoter.

Figure 29:
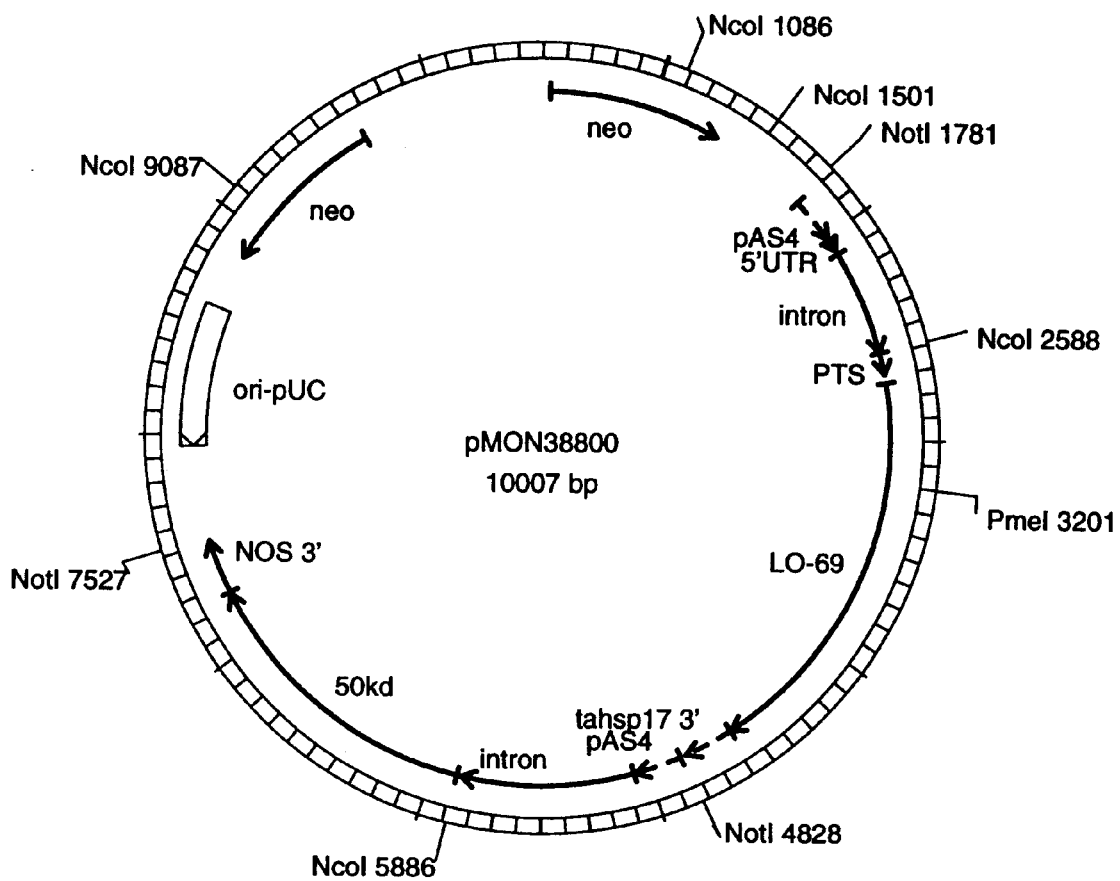

FIG. 29 represents a plasmid map of pMON38800, which is a plant transformation vector containing a neomycin phosphotransferase gene under the control of a cauliflower mosaic virus 35S promoter; a lysine oxidase gene fused to an amino terminal His6 coding region, a rice malate dehydrogenase amino terminal peroxisomal targeting signal, an intron and a 5' wheat chloroplast AB untranslated leader under the control of a 4AS1 promoter and a wheat 17 kd heat shock protein 3' untranslated sequence; and a tedanalactam synthase gene fused to an intron under the control of a 4AS 1 promoter and a nopaline synthase 3' untranslated sequence.

DETAILED DESCRIPTION OF THE INVENTION

The following detailed description of the invention is provided to aid those skilled in the art in practicing the present invention. Even so, the following detailed description should not be construed to unduly limit the present invention as modifications and variations in the embodiments discussed herein may be made by those of ordinary skill in the art without departing from the spirit or scope of the present inventive discovery.

The work described herein has identified compositions and methods of expressing an amino acid oxidase gene in combination with a second gene encoding a protein which, when provided in a composition with the amino acid oxidase, confers plant resistance to coleopteran insects. Agronomic, horticultural, ornamental, and other economically or commercially useful plants can be made in a functionally operable manner, described herein, to express effective levels of protein to confer resistance to coleopteran insects. Such plants may co-express the genes encoding the amino acid oxidase and the second gene along with other genes encoding antifungal, antibacterial, or antiviral pathogenesis-related peptides, polypeptides, or proteins; insecticidal proteins; proteins conferring herbicide resistance; and genes encoding proteins involved in improving the quality of plant products or agronomic performance of plants. Simultaneous co-expression of multiple proteins in plants is advantageous in that it exploits more than one mode of action to control plant pathogenic damage. This can minimize the possibility of developing resistant pathogen strains, broaden the scope of resistance, and potentially result in a synergistic effect, thereby enhancing the level of resistance. Note WO 92/17591, for example, in this regard. Examples are provided herein in which a lysine oxidase and a second gene which encodes a tedanalactam synthase are used in combination to control coleopteran insects through either direct feeding or by use of microbes expressing genes which encode these proteins.

As used herein, the term composition means a mixture of ingredients which, when combined, provides an insecticidally effective substance containing an amount of the active ingredients encoded by a first enzyme comprising an amino acid oxidase and a second enzyme that provides insecticidal activity when the second enzyme is present in the mixture with the first enzyme. The composition can be an artificial mixture comprising the two active ingredients along with aqueous or non-aqueous ingredients which may be combined to provide a substrate suitable for feeding to an insect. The feeding insect can be a larvae form or may be an adult form. The composition can also be a mixture which contains one or more bacteria expressing the genes encoding the first and the second enzymes, such that the mixture, when provided in a suitable form for feeding to insects, causes an insecticidally effective amount of the two gene products to be delivered to the feeding insects. The composition can also be a mixture within plant tissues or plant cells, produced as a result of expression of the genes encoding the first and the second enzymes by the plant nuclear or nucleolar genome, by the plant mitochondrial genome, or by the plant chloroplast genome, such that the mixture, when consumed by a feeding insect, causes an insecticidally effective amount of the two gene products to be delivered to the feeding insects.

By "controlling insect infestation" it is meant that the composition upon which susceptible insects feed, usually a crop expressing the contemplated genes, is capable of delivering an insecticidally effective amount of the amino acid oxidase and the second gene product to the feeding insect so that insect growth is stunted, or slowed, or that the insect dies without causing an unnecessary or unacceptable amount of crop damage.

"A plurality of cells" is intended to mean two or more cells, and the cells can be of any type which are capable of being transformed with the genetic constructs described herein, such as bacterial cells, plant cells, yeast cells, insect cells, and fungal cells.

"An insecticidally effective amount" is intended to mean any amount of any composition described herein capable of providing insecticidal activity upon ingestion of the composition by a susceptible insect, wherein the composition contains at least an amino acid oxidase and a second gene product that provides insecticidal activity when present in a mixture with the amino acid oxidase. The insecticidal activity is readily observed upon ingestion by a susceptible insect. A susceptible insect which consumes an insecticidally effective amount will not continue to grow at the same rate as a control susceptible insect.

Stringent conditions as related to polynucleotide hybridization is well known in the art, and so one skilled in the art would know that a number of factors are applicable, both in influencing the stability of hybrid polynucleotide molecules and in influencing the hybridization rate of polynucleotides. For example, factors which influence hybrid stability include ionic strength of any hybridization solution; the base composition of the probe and the target polynucleotides; destabilizing agents present in the hybridization solution such as formamide or urea; the presence or availability of mismatched base pairs; and the duplex length of the probe or target. All of these factors also influence the hybridization rate in addition to the temperature selected for hybridization; the viscosity of the solution; the complexity of the probe, meaning the presence of repetitive sequences which would tend to increase the hybridization rate; the pH of the hybridization solution; and the base composition of the probe and target. One skilled in the art would be able to determine the optimum conditions for establishing stringency as related to identifying a polynucleotide by using hybridization under stringent conditions to a probe of known base pair composition.

Trichoderma sp. genes that encode 1) lysine oxidase (E.C. 1.4.3.14) proenzyme and 2) a $M_r$ 50,000 tedanalactam synthase have been isolated and sequenced. These new genes or genes from other organisms known to produce or capable of producing lysine or other amino acid oxidases or proproteins and a tedanalactam synthase may be inserted into expressible cassettes which can then be placed into a transformation vector for use in transforming plant-colonizing microorganisms which, when applied to plants, express the genes producing these proteins, thereby providing control of insects. Alternatively, genes which are also part of expression cassettes, and which function in plants to encode the subject proteins may be inserted into plant transformation vectors for use in transforming the genome of a plant or plant subcellular organelle such as a mitochondria or chloroplast. Such transformed plants are thus provided with a capability to protect itself from attack by expressing the recombinant gene or genes and producing a lysine or amino acid oxidase along with a tedanalactam synthase. Additionally, the plant expressing this combination of insecticidal proteins may also be transformed or crossed with other recombinant plants to obtain plants expressing B.t. genes for the control of either the same or additional insects. Alternatively, the recombinant plants expressing this combination of insecticidal proteins may be crossed to other, more preferable germ plasm for purposes of providing commercial product lines. Examples of plants transformed to express B.t. genes are disclosed in European Patent Publication No. 0385 962 (Fischhoff and Perlak, 1990).

An expression cassette is intended to mean a DNA molecule comprising a promoter sequence which functions to cause the production of an RNA sequence from a DNA sequence containing an open reading frame encoding either an amino acid oxidase, a second enzyme which provides insecticidal activity when present in a mixture with an amino acid oxidase, or a chimeric gene open reading frame constructed from the in frame fusion of an amino acid oxidase and a second enzyme which provides insecticidal activity when present in a mixture with an amino acid oxidase. The promoter sequence is required to be operably or operatively linked to the DNA sequence containing one or more of the open reading frames. It is understood that the promoter chosen is functional in a particular cell type. The cell type in which a promoter is functional can be any known in the art, in particular a bacterial or bacterial virus promoter is known to be functional in various bacterial species; a plant or plant virus promoter is known to be functional in various plant species or in various plant cells, either tissue specific or non-tissue specific. A promoter which is root enhanced or root specific or root tissue specific is one which provides expression preferentially in cells derived from root tissues in a variety of plant types, and more particularly in corn, rice, wheat, soybean, canola, and cotton. By root enhanced it is meant that the promoter has been isolated or genetically engineered to preferentially express or be more active in root tissue when compared to other plant tissue types such as leaves, fruit, flowers, and such. In eukaryotic cell types, and preferably in plant cell types, a particular expressible cassette includes a 3' non-translated DNA sequence which functions in plants to cause the addition of a polyadenylated nucleotide sequence to the 3' end of an RNA sequence generated from the function of an upstream operable promoter and gene sequence.

Expressible cassettes can also contain other elements in addition to those described above. For example, a DNA sequence which specifies a 5' non-translated leader sequence can be present downstream of the promoter but upstream of the translatable gene sequence. DNA which specifies leader sequences are generally found in association with particular promoter sequences, yet have been successfully utilized when associated with heterologous promoters and gene sequences. Such leader sequence can increase expression levels of desired proteins when associated with particular genes. Another DNA sequence which can increase expression levels of desired proteins when associated with particular genes specifies a non-translated RNA sequence known as an intron. Introns are well known in the art. Intron sequences are excised post-transcriptionally from the initial RNA transcript while still within the boundaries of the nuclear envelope in a process known as splicing in which RNA 5' adjacent to the intron sequence and 3' adjacent to the intron sequence are fused to create the resulting MRNA sequence which is ultimately translated into a protein product. In this application, intron sequences are preferred in gene constructs which are prepared for insertion into monocotyledenous species of plants, however this is not meant to be limiting, because introns can function in dicotyledenous species for the same purposes. Introns preferably are provided downstream of a promoter but upstream of the gene coding sequence, however introns can also be placed within a gene coding sequence, or even downstream of a gene coding sequence but upstream of a 3' non-translated polyadenylation coding sequence. Other elements can be signal peptide encoding sequences or transit peptide encoding sequences. These are also well known in the art. Signal peptides are ubiquitous and are generally fifteen to thirty amino acids long and are directed to targeting a precursor peptide, often a nascent peptide, to a secretion or secretory apparatus within the cell. The secretory apparatus can be found on or within the cytoplasmic or intracytoplasmic membrane of a bacterium or the endoplasmic reticulum, Golgi, or other vacuolar or cytoplasmic membrane surface to which the signal peptide directs the precursor peptide. The signal peptide is generally cleaved by some faction of the secretory apparatus to release a proenzyme in which case the precursor would be a pre-proenzyme, or to release a mature peptide. A targeting or transit peptide encoding sequence similarly directs a protein to a particular membrane surface, which can be either a plastid, a chloroplast, or a mitochondria. The targeting or transit peptide leads the attached protein sequence into the particular organelle, and is generally cleaved to release the mature peptide into the particular organelle.

A DNA vector can be any of a number of constructions which are well known in the art. These can be selected from the group consisting of but not limited to plasmid, bacmid, phage, cosmid, yeast artificial chromosome (YAC), bacterial artificial chromosome (BAC), plant virus, or linear DNA or RNA, so long as the vector is capable of being delivered to a target cell for the express purpose of either transforming the cell by incorporation into the genome of the cell, by stable or temporary replication or otherwise existing for a period of time within the target cell so that the genes encoding proteins, which in combination provide or exhibit coleopteran insecticidal activity, are able to produce the contemplated composition either for purposes of enzymatic or immunological detection or for protection of a plant or plant cell from insect damage.

The present invention includes not only the Trichoderma lysine oxidase and tedanalactam synthase proteins, but also biologically equivalent peptides, polypeptides, and proteins. The phrase "biologically equivalent peptides, polypeptides, and proteins" denotes peptides, polypeptides, and proteins that exhibit the same or similar activities when assayed in comparison to the Trichoderma counterpart by in vitro or in vivo assays. The phrase "same or similar activities" denotes the ability to perform the same or similar function as the Trichoderma counterpart. These peptides, polypeptides, and proteins can contain a region or moiety exhibiting sequence similarity to a corresponding region or moiety of the Trichoderma proteins disclosed herein, but this is not required as long as they exhibit the same or similar activity as their Trichoderma counterpart. Biologically equivalent peptides, polypeptides, and proteins may include, but are not limited to truncated fragments deleted from the N-terminal end, C-terminal end, internal regions of the protein, or combinations thereof. Additionally, variants resulting from changes in one or more amino acid to a different natural or non-natural amino acid, deletions, or insertions of natural or non-natural amino acids may result in a biologically equivalent compound. Such variants may be naturally occurring materials, or may be produced by mutagenesis or random mutagenesis of the encoding nucleotide sequence.

The present invention encompasses not only the Trichoderma DNA sequences listed, but also biologically functional equivalent nucleotide sequences. The phrase "biologically functional equivalent nucleotide sequences" denotes DNAs and RNAs, including genomic DNA, cDNA, synthetic DNA, and mRNA nucleotide sequences, that encode peptides, polypeptides, and proteins exhibiting the same or similar activities as the Trichoderma lysine oxidase or tedanalactam synthase when assayed by in vitro or in vivo methods. Such biologically functional equivalent nucleotide sequences can encode peptides, polypeptides, or proteins that contain a region or moiety exhibiting sequence similarity to the corresponding region or moiety of the Trichoderma counterpart. Nucleotide sequences may contain conservative amino acid changes, altering the codon usage for a particular amino acid, but leaving the encoded peptide, polypeptide, or protein sequence unchanged. Alternatively, nucleotide sequences may contain non-conservative changes including, but not limited to substitutions, deletions, additions, or combinations thereof. These biologically functional equivalent nucleotide sequences may be naturally occurring or produced by in vitro methods. These biologically functional equivalent nucleotide sequences are preferably 80% identical to their Trichoderma counterparts. More preferably, biologically functional equivalent nucleotide sequences are 85%, 87.5%, 90%, 92.5%, 95%, 97.5%, and ideally 100% identical to their Trichoderma counterparts. Biologically functional equivalent nucleotide sequences may be identified by their capability of hybridizing under stringent conditions to the lysine oxidase or tedanalactam synthase encoding sequences, or the complements thereof.

Methods for identifying other genes which encode a first gene encoding an amino acid oxidases and a second gene which encodes a protein that provides insecticidal activity when present in a mixture with an amino acid oxidase are contemplated herein. Methods for identifying such sequences are well known in the art, however the novelty of the second gene provides a particular advantage to the invention. The second gene described herein as a tedanalactam synthase can be used to detect and identify the presence of other genes of substantial similarity, meaning genes which are capable of being detected by hybridization to the tedanalactam synthase gene. Any mixture or sample containing a polynucleotide sequence encoding a protein that provides insecticidal activity when present in a mixture with an amino acid oxidase can be probed with a labeled polynucleotide sequence which is or is complementary to all or a portion of the tedanalactam synthase gene. The act of probing a sample with the tedanalactam synthase gene will provide a probe/sample complex in mixtures which contain a homologous gene or a heterologous gene capable of binding to the probe. The probe/sample complex can be detected in any number of ways not limited to enhanced chemiluminescence, radioisotopic, fluorescent, or colorimetric methods well known in the art. The complex can be isolated, particularly if the method chosen has utilized a phage blot or a cell culture blot method. The polynucleotide or polynucleotides which bound to the probe can be isolated either from the probe/sample complex or derived from the particular sample which gave rise to the probe/sample complex to yield a gene which encodes a protein that provides insecticidal activity when present in a mixture with an amino acid oxidase. The gene isolated in this way may or may not have tedanalactam synthase activity.

Antibodies can be generated to detect either of the active peptides which comprise the compositions herein. An amino acid oxidase enzyme or a tedanalactam synthase enzyme can be purified by any number of means well known in the art. Purified enzymes can be provided in adjuvant form for injection into a variety of animals, also well known in the art. Preferably rabbits are used, however goats, guinea pigs, horses, turkeys, chickens, and even humans could be used for producing reagent grade antiserum directed to particular epitopes of these proteins for use in methods which utilize antibodies for detection and purification of such peptides. While serum from animals provides polyclonal antibodies which are directed to a large number or a variety of epitopes on each protein, monoclonal antibodies could easily be produced by methods well known in the art.

Kits could also be used, in particular when immunological reagents are available, such as antibodies directed to detection of amino acid oxidase or tedanalactam synthase enzyme, or by designing oligonucleotide sequences for use in detecting the presence of genes contemplated herein by thermal amplification methods or in combination with immunological methods.

The expression of a plant gene which exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region which adds polyadenylate nucleotides to the 3' end of the RNA. Transcription of DNA into mRNA is regulated by a region of DNA usually referred to as the "promoter". The promoter region contains a sequence of bases that signals RNA polymerase to associate with the DNA and to initiate the transcription of mRNA using one of the DNA strands as a template to make a corresponding strand of RNA.

One skilled in the art will recognize that many promoters, 5' non-translated leader sequences, introns and polyadenylation sequences may be used in accordance with the present invention. Suitable examples of promoter sequences include, but are not limited to nopaline synthase (NOS), octopine synthase (OCS), cauliflower mosaic virus 19S and 35S (CaMV19S, CaMV35S), ribulose 1,5-bisphosphate carboxylase (ssRUBISCO), figwort mosaic virus (FMV), asparagine synthase, glutathione-S-transferase, T-DNA, CPRFl, histone H3, wheat gliadin, nopaline synthase, Agrobacterium rhizogenes rolC, tobacco anionic peroxidase, napA storage protein, Cassava vein mosaic virus (CVMV), polyubiquitin, glycinin Gy2, mas, mustard CHS1, Chlorella virus adenine methyltransferase, Arabidopsis phenylalanine ammonia-lyase, potato ubi3, and the tomato hmg2 promoter. Suitable examples of root enhanced or root specific promoter sequences include, but are not limited to CaMV derived AS4, tobacco RB7, and the rice RC2 promoter. Suitable examples of intron sequences include, but are not limited to the maize heat shock protein 70 (hsp70), rice actin, cox11, histone H3, RNA polymerase II, chloroplast DNA trnl, maize ADH1 intron 1, maize actin intron 3, Arabidopsis thaliana polyubiquitin, and the plant hemoglobin exon 2 intron. Suitable examples of 5' leader sequences include, but are not limited to petunia heat shock protein 70 (hsp70), AMV RNA4, 16S ribosomal, Arabidopsis ACT2, Arabidopsis ACT8, TMV RNA, and soybean Gy2. Suitable examples of polyadenylation signals include, but are not limited to Agrobacterium nopaline synthase (NOS) and the *Pisum sativum* RUBISCO small subunit E9.

A number of promoters which are active in plant cells have been described in the literature. Such promoters may be obtained from plants or plant viruses and include, but are not limited to, the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose 1,5-bisphosphate carboxylase (ssRUBISCO, a very abundant plant polypeptide), and the Figwort Mosaic Virus (FMV) 35S promoter. All of these promoters have been used to create various types of DNA constructs which have been expressed in plants (see e.g., Barry and Kishore, U.S. Pat. No. 5,463,175).

The particular promoter selected should be capable of causing sufficient expression of the enzyme coding sequence to result in the production of an insecticidal effective amount of lysine oxidase and tedanalactam synthase. One set of preferred promoters are constitutive promoters such as the CaMV35S or FMV35S promoters that yield high levels of expression in most plant organs. Another set of preferred promoters are root enhanced or specific promoters such as the CaMV derived AS4 promoter, the tobacco RB7 promoter, or the rice RC2 promoter (Lam et al., 1991; Yamamoto et al., 1991; Hertig et al., 1991; Xu et al., 1995). The root enhanced or specific promoters would be particularly preferred for the control of corn rootworm (Diabrotica spp.) in transgenic corn plants.

The promoters used in the DNA constructs (i.e. chimeric plant genes) of the present invention may be modified, if desired, to affect their control characteristics. For example, the CaMV35S promoter may be ligated to the portion of the ssRUBISCO gene that represses the expression of ssRUBISCO in the absence of light, to create a promoter which is active in leaves but not in roots. The resulting chimeric promoter may be used as described herein. For purposes of this description, the phrase "CaMV35S" promoter thus includes variations of CaMV35S promoter, e.g., promoters derived by means of ligation with operator regions, random or controlled mutagenesis, etcetera. Furthermore, the promoters may be altered to contain multiple "enhancer sequence" to assist in elevating gene expression. Examples of such enhancer sequences have been reported by Kay et al. (1987).

The RNA produced by a DNA construct of the present invention also contains a 5' non-translated leader sequence. This sequence can be derived from the promoter selected to express the gene, and can be specifically modified so as to increase translation of the MRNA. The 5' non-translated regions can also be obtained from viral RNAs, from suitable eucaryotic genes, or from a synthetic gene sequence. The present invention is not limited to constructs wherein the non-translated region is derived from the 5' non-translated sequence that accompanies the promoter sequence. As shown below, a plant gene leader sequence which is useful in the present invention is the petunia heat shock protein 70 (hsp70) leader (Winter et al., 1988).

For optimized expression in monocotyledenous plants, an intron should also be included in the DNA expression construct. This intron would typically be placed near the 5' end of the mRNA in untranslated sequence. This intron could be obtained from, but not limited to, a set of introns consisting of the maize hsp70 intron (Brown and Santino U.S. Pat. No. 5,424,412; 1995)or the rice Act1 intron (McElroy et al., 1990). As shown below, the maize hsp70 intron is useful in the present invention.

As noted above, the 3' non-translated region of the chimeric plant genes of the present invention contains a polyadenylation signal which functions in plants to cause the addition of adenylate nucleotides to the 3' end of the RNA. Examples of preferred 3' regions are (1) the 3' transcribed, non-translated regions containing the polyadenylate signal of Agrobacterium tumor-inducing (Ti) plasmid genes, such as the nopaline synthase (NOS) gene and (2) plant genes such as the pea ssRUBISCO E9 gene (Fischhoff et al., 1987).

A chimeric plant gene containing the structural coding sequences of the present invention can be inserted into the genome of a plant by any suitable method. Suitable plant transformation vectors include those derived from a Ti plasmid of *Agrobacterium tumefaciens,* as well as those disclosed, e.g., by Herrera-Estrella (1983), Bevan (1983), Klee (1985) and EPO publication 0 120 516 (Schilperoort et al.). In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen (Fromm et al., 1986; Armstrong et al., 1990; Fromm et al., 1990).

To identify a transgenic plant expressing lysine oxidase and/or tedanalactam synthase, it is necessary to screen the herbicide or antibiotic resistant transgenic, regenerated plants (R0 generation) for expression of these genes. This can be accomplished by various methods well known to those skilled in the art, including but not limited to: 1) obtaining small tissue samples from the transgenic R0 plant and directly assaying the tissue for activity against susceptible insects in parallel with tissue derived from a non-expressing, negative control plant. For example, R0 transgenic potato plants expressing lysine oxidase and tedanalactan synthase can be identified by assaying leaf tissue derived from such plants for activity against CPB; 2) analysis of protein extracts by enzyme linked immunoassays (ELISAs) or immunoblot assays specific for lysine oxidase and/or tedanalactam synthase (antibodies useful for such detection schemes are described in the examples) or 3) reverse transcriptase PCR (RT PCR) to identify events expressing the gene of interest.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

EXAMPLES

The present invention can be better understood from the following illustrative, non-limiting Examples. Effective control of coleopteran insect pests is demonstrated when these proteins are obtained or expressed within their natural source organism, in heterologous microorganisms, or in transgenic plants.

Example 1

This example illustrates the discovery and characterization of insecticidal activity from a Trichoderma species.

The culture filtrate from a Trichoderma species, Monsanto fungal isolate # F22844, was found to exhibit insecticidal activity in a southern corn rootworm bioassay. The proteinaceous nature of the active component was suggested by characterization experiments which showed that first, the corn rootworm activity was completely lost after heating and second, only components within the filtrate which were larger than 10 kDa in size maintained insecticidal bioactivity (Table 1). A qualitative visual assessment of the assay revealed that the >10 kDa sample severely stunted the surviving larvae and also had ovicidal effects in addition to the mortality noted in Table 1.

A sample of a >10 kDa preparation of F22844 was utilized in diet-preincubation studies to determine if the corn rootworm activity was due to a modification of the artificial diet. It was demonstrated that diet pre-incubated with F22844 retained full insecticidal activity, while similar samples subjected to heat treatment prior to larval addition exhibited reduced bioactivity (Table 1).

An important consideration in determining the utility of an insecticidal lead is bioactivity in bioassays using plant tissue in the assay media. F22844 retained its insecticidal activity in assays with plant tissue when a >10 kDa preparation of F22844 was added to BMS corn callus. Significant mortality of corn rootworm larvae feeding on this material was seen in this bioassay (Table 1).

TABLE 1

|  | % Mortality |
|---|---|
| Sizing and heat lability study | |
| [>10kDa] | 68 |
| [<10kDa] | 0 |
| [>10kDa] - Heated 100° C. | 0 |
| Diet pre-incubation study | |
| Un-incubated | 94 |
| Incubated | 94 |
| Incubated/Heated 80° C. | 19 |
| Callus diet assay | |
| [>10 kDa] | 94 |

Example 2

This example illustrated the identification and characterization of proteins with insecticidal activity isolated from Trichoderma fermentation extracts.

SDS-PAGE analysis of chromatography fractions generated during the purification of the southern corn rootworm-active protein(s) from F22844 showed that major proteins of $M_r$ 56,000 and $M_r$ 50,000 were present in the corn rootworm-active fractions. These proteins were then purified by sizing and ion exchange chromatography. This protocol consistently yielded significantly purified proteins. The bioassay results obtained with purified proteins from two separate fermentations of F22844 are shown in Tables 2a and 2b. In both cases, no bioactivity was detected when the proteins were assayed individually but significant stunting was seen when the proteins were combined in assay. These results demonstrate that it is a combination of the two proteins that is responsible for the corn rootworm activity in F22844.

TABLE 2a

| Sample | Conc. (µg/mL) | Mean larval weight (mg) ± (SEM) | % Stunting |
|---|---|---|---|
| Acetate buffer | 0 | 1.14 ± (0.17) | — |
| $M_r$ 56,000 | 10 | 0.91 ± (0.09) | NSS |
| $M_r$ 50,000 | 1.5 | 0.83 ± (0.05) | NSS |
| $M_r$ 56,000 + $M_r$ 50,000 | 10 + 1.5 | 0.37 ± (0.07) | 67 |

NSS = not statistically significant

TABLE 2b

| Sample | Conc. (µg/mL) | Mean larval weight (mg) ± (SEM) | % Stunting |
|---|---|---|---|
| Acetate buffer | — | 1.29 ± (0.16) | — |
| $M_r$ 56,000 | 2 | 1.63 ± (0.22) | — |
| $M_r$ 50,000 | 2 | 1.39 ± (0.22) | — |
| $M_r$ 56,000 + $M_r$ 50,000 | 2 + 2 | 0.56 ± (0.22) | 57 |

Native-PAGE studies were effective in confirming that the $M_r$ 56,000 and $M_r$ 50,000 proteins were responsible for the southern corn rootworm bioactivity of F22844. The chromatographically purified $M_r$ 56,000 and $M_r$ 50,000 proteins were further purified by native PAGE. SDS-PAGE analysis demonstrated that the proteins were purified to single bands. The individual purified proteins did not yield statistically significant stunting of corn rootworm (Table 3). A sample containing a combination of the two proteins at concentrations of 9.7 $\mu$g/mL of $M_r$ 56,000 and 2.5 $\mu$g/mL of $M_r$ 50,000 yielded 89% stunting of corn rootworm larvae (Table 3).

TABLE 3

| Sample | Conc. ($\mu$g/mL) | Mean larval weight (mg) ± (SEM) | % Stunting |
|---|---|---|---|
| Acetate buffer | 0 | 0.88 ± (0.11) | — |
| $M_r$ 56,000 | 9.7 | 0.84 ± (0.06) | NSS |
| $M_r$ 50,000 | 2.5 | 1.04 ± (0.11) | NSS |
| $M_r$ 56,000 + $M_r$ 50,000 | 9.7 + 2.5 | 0.10 ± (0.01) | 89 |

An SDS-PAGE gel of the proteins produced by Trichoderma F22844, isolated as above, were blotted onto a PVDF membrane (Immobilon, Millipore, Bedford, Mass.) using the protocol of Matsudaira (Matsudaira, 1987). The N-terminus was sequenced using automated Edman degradation chemistry. A gas phase sequencer (Applied Biosystems, Foster City, Calif.) was used for the degradation using the standard sequencer cycle. The respective PTH-aa derivatives were identified by reverse phase HPLC analysis in an on-line fashion employing a PTH analyzer (Applied Biosystems, Foster City, Calif.) fitted with a Brownlee 2.1 mm i.d. PTH-C18 column. For internal sequences, digestions were carried out on purified lysine oxidase and $M_r$ 50,000 proteins from F22844 using trypsin (TPCK-treated, from Worthington Biochemicals Corp., Freehold, N.J.). Fragments were then purified by reverse phase HPLC and sequenced in an N-terminal fashion.

F22844 was identified taxonomically as a Trichoderma species. A search in the CRC antibiotic database for proteins produced by Trichoderma yielded L-lysine oxidase (LO), an $M_r$ 56,000 protein identified as an antitumor agent (Kusakabe et al., 1979; 1980). The purified $M_r$ 56,000 protein from F22844 was identified as L-lysine oxidase by enzymatic assay (Gallo et al., 1981). We determined the lysine oxidase from F22844 to have a $K_m$ for lysine of 26 $\mu$M, a value very similar to the reported $K_m$ for lysine of 40 $\mu$M for the T. viride lysine oxidase (Kusakabe et al., 1980). The substrate specificity of F22844 lysine oxidase was also determined (Table 4). The relative reaction rates are very similar to the values in the literature for T viride lysine oxidase (Kusakabe et al., 1980).

TABLE 4

| | Relative activity (%) | |
|---|---|---|
| Substrate[a] | F22844[a] | *T. viride*[b] |
| Lysine | 100.0 | 100 |
| Ornithine | 10.8 | 18.2 |
| Phenylalanine | 6.6 | 8.3 |
| Histidine | 5.0 | 3.8 |
| Arginine | 2.6 | 6.1 |

[a]Relative activities of less than 1% were detected with L-isomers of leucine, proline, threonine, tryptophan, serine, alanine, asparagine, valine, methionine, tyrosine, glutamic acid, glutamine, isoleucine, glycine, aspartic acid and cysteine.
[b]*T. viride* data from Kusakabe et al., 1980. No activity against L-isomers of leucine, proline, threonine, tryptophan, serine, alanine, asparagine, valine, methionine, tyrosine, glutamic acid, glutamine, isoleucine, glycine, aspartic acid and cysteine was observed (Kusakabe, et al., 1980).

Data generated thus far indicate that the $M_r$ 50,000 protein catalyses the conversion of $\Delta^1$-piperideine-2-carboxylate (P2C) to product I. High resolution mass spectral data suggest that I is the 3,4-epoxide of 2-piperidone, which has previously been identified as tedanalactam (Cronan and Cardellina, 1994). Hydrogen peroxide appears to be the byproduct of the $M_r$ 50,000 protein reaction. The formation of hydrogen peroxide was monitored by a colorimetric assay (Gallo, 1981). P2C was prepared by two separate methods for the initial $M_r$ 50,000 protein assay. The two methods used for preparing P2C were 1) L-lysine with lysine oxidase and catalase; and
2) DL-pipecolic acid with D-amino acid oxidase and catalase.

P2C was isolated from the protein mixture by filtration using an Amicon filter (10 kDa cutoff) before using in the $M_r$ 50,000 protein assay. Pipecolic acid and lysine are not substrates of $M_r$ 50,000 protein.

Note that in proposing an enzymatic activity for the $M_r$ 50,000 protein, we do not limit our claims. More specifically, we propose that both the $M_r$ 50,000 protein and any substantially homologous proteins will yield coleopteran insect control when combined with lysine oxidase and other amino acid oxidases. Moreover, it is conceived that any enzyme capable of converting $\Delta^1$-piperideine-2-carboxylate to tedanalactam would be considered by one skilled in the art to have tedanalactam synthetic activity, and would be characterized as a tedanalactam synthase enzyme. Any tedanalactam synthase enzyme capable of converting $\Delta^1$-piperideine-2-carboxylate to tedanalactam could be used in compositions with lysine oxidase or other amino acid oxidases as described herein for controlling insect infestation of plants, and may also be effective in controlling insect infestation in general when supplied in any form capable of being ingested by an insect. Genes encoding tedanalactam synthases may not necessarily be homologous to genes encoding such enzymes isolated from fuigal species such as Trichoderma. Other tedanalactam synthase genes may encode enzymes which would be substantially smaller than such enzymes observed from Trichoderma. Conversely, it is entirely possible that still other tedanalactam synthase genes may encode enzymes which are substantially larger than such Trichoderma enzymes. Therefore, it is not desired that this invention be limited to enzymes approximately $M_r$ 50,000 having tedanalactam synthase activity.

Example 3

This example illustrates the bioactivity of lysine oxidase and the tedanalactam synthase derived from naturally occurring source organisms.

Lysine oxidase and tedanalactam synthase were purified from culture filtrates of the native F22844 fungus. Both proteins were greater than 90% pure by SDS-PAGE. Concentration response curves were run to determine the efficacy of these purified proteins on neonate western corn rootworm, *Diabrotica virgifera virgifera* LeConte larvae. An $LC_{50}$ below 2 ppm of each protein was demonstrated (Table 5).

TABLE 5

| Sample | Conc. (ppm) | % Mortality | % Stunting |
|---|---|---|---|
| LO + $M_r$ 50,000 | 20 + 20 | 100 | — |
|  | 10 + 10 | 100 | — |
|  | 2 + 2 | 63 | 80 |
| Control | — | 0 | 0 |

Western corn rootworm, *Diabrotica virgifera virgifera* LeConte, bioassays were also conducted using second instar larvae with lysine oxidase present at 30 ppm and tedanalactam synthase present at 4 ppm. By day 10, the western corn rootworm larvae exposed to the active proteins had a corrected mortality of 81% and the surviving larvae actually lost weight over the course of the assay (Table 6).

TABLE 6

| Sample | # Larv. Initial Day 1 | Larval Wt. (mg)- Day 1 ± (SEM) | # Larv. Surv. Day 4 | # Larv. Surv. Day 7 | # Larv. Surv. Day 9 | #Surv. Day 10 | Larval Wts. (mg)- Day 10 ± (SEM) |
|---|---|---|---|---|---|---|---|
| Buffer control | 48 | 2.63 ± (0.18) | 46 | 44 | 43 | 43 | 8.48 ± (0.57) |
| Lysine oxidase + $M_r$ 50,000 | 48 | 2.63 ± (0.18) | 38 | 21 | 10 | 8 | 1.44 ± (0.10) |

Concentration response studies using chromatographically purified proteins were conducted. A concentration of 10 ppm of each protein (lysine oxidase+tedanalactam synthase) yielded 80% stunting of southern corn rootworm while 2 ppm of each yielded 60% stunting (Table 7).

TABLE 7

| Sample | Conc. (μg/mL) | Mean larval weight (SEM) | % Stunting |
|---|---|---|---|
| Acetate buffer | 0 | 1.00 (0.11) | — |
| Lysine oxidase + $M_r$ 50,000 | 2 + 2 | 0.40 (0.05) | 60 |
| Lysine oxidase + $M_r$ 50,000 | 10 + 10 | 0.20 (0.05) | 80 |

The purified proteins were also bioassayed in a BMS callus diet and bioactivity was retained in this assay (Table 8). These data demonstrated that the proteins were bioactive against southern corn rootworm in plant based bioassays in addition to artificial diet bioassays.

TABLE 8

| Sample | Conc. (μg/mL) | Mean larval weight (mg) ± (SEM) | % Stunting |
|---|---|---|---|
| Artificial Diet |  |  |  |
| Acetate buffer | 0 | 1.15 ± (0.28) | — |
| Lysine oxidase + $M_r$ 50,000 | 17 + 2 | 0.35 ± (0.06) | 70 |
| BMS Callus |  |  |  |
| Acetate buffer | 0 | 0.27 ± (0.04) | — |
| Lysine oxidase + $M_r$ 50,000 | 17 + 2 | 0.13 ± (0.01) | 53 |

Bioassays were done with purified $M_r$ 56,000+$M_r$ 50,000 proteins from F22844 against two other coleopteran insects. Bioactivity was detected against Colorado potato beetle, *Leptinotarsa decemlineata* (Say), and boll weevil, *Anthonomus grandis grandis* Boheman.

TABLE 9

| Sample | Surv/Init | % Mortality | Mean larval wt (mg) ± (SEM) | % Stunting |
|---|---|---|---|---|
| Boll weevil |  |  |  |  |
| Buffer control | 30/32 | — | 11.05 ± (1.49) | — |
| LO + 50 (2 ppm each) | 13/16 | 13 | 12.07 ± (2.05) | — |
| LO + 50 (6 ppm each) | 11/16 | 27 | 5.67 ± (2.10) | 49 |
| LO + 50 (18 ppm each) | 6/16 | 60 | 1.42 ± (0.48) | 87 |
| CO. potato beetle |  |  |  |  |
| Buffer control | 31/32 | — | 3.31 ± (0.33) | — |
| LO + 50 (2 ppm each) | 15/16 | 3 | 2.83 ± (0.24) | 15 |
| LO + 50 (6 ppm each) | 12/16 | 22 | 2.57 ± (0.48) | 23 |
| LO + 50 (18 ppm each) | 8/16 | 48 | 2.08 ± (0.32) | 37 |

Culture supernatants from four other Monsanto fungal isolates that had corn rootworm insecticidal activity were strongly positive for lysine oxidase enzymatic activity-F25528, F25634, F26040 and F25508. These leads were not characterized further. Culture supernatants from ATCC *T.viride* isolates #20536 and #20538 expressed lysine oxidase and an $M_r$ 50,000 protein and were insecticidally active against southern corn rootworm. Lysine oxidase from *Trichoderma viride* is available commercially from Sigma (St. Louis, Mo.). The enzyme was purified to a single band from this preparation and bioassayed against southern corn rootworm. Bioassays were conducted to compare the concentration responses of the *T. viride* lysine oxidase (±$M_r$ 50,000 protein from F22844) with the lysine oxidase purified from F22844. The bioactivity of the *T viride* lysine oxidase agrees very well with the bioactivity of lysine oxidase from F22844 when bioassayed in the presence of tedanalactam synthase from F22844 (Table 10). Very similar stunting levels are seen at equivalent doses (compare Table 10 to Table 7). In addition, no bioactivity is seen with either lysine oxidase in the absence of tedanalactam synthase from F22844.

TABLE 10

| Sample | Conc. (ppm) | Mean larval weight (mg) ± (SEM) | % Stunting |
|---|---|---|---|
| Buffer control | 0 | 0.77 ± (0.09) | — |
| T. viride LO | 10 | 0.74 ± (0.07) | 4* |
| T. viride LO | 2 | 0.73 ± (0.09) | 5* |
| T. viride LO + F22844 $M_r$ 50,000 | 10 + 10 | 0.21 ± (0.04) | 73 |
| T. viride LO + F22844 $M_r$ 50,000 | 2 + 2 | 0.39 ± (0.05) | 49 |

*not statistically significant

Example 4

This example illustrates mode of action studies of the lysine oxidase and tedanalactam synthase and effects which were observed on the corn root worm midgut.

The effects of lysine oxidase and tedanalactam synthase proteins on the morphology and ultrastructure of the southern corn rootworm midgut were investigated by light and electron microscopy. Light microscopy showed that the midguts were intact with microvilli but there was marked apical folding of epithelium and basal infolding in treated individuals and an apparent loss of the basal regenerative cells. Several ultrastructural changes were evident by electron microscopy. The rough endoplasmic reticulum of the epithelial cells was dramatically reduced in treated individuals indicating a reduced potential for protein synthesis. There was an increased electron density (osmiophilia) of lateral plasma membranes suggesting an abnormality in lipid metabolism. In the fat body, lipid vesicles were significantly reduced in treated individuals. These micrographs showed that there are some definite cellular changes associated with the treatment of corn rootworm with the purified proteins.

Example 5

This example describes the isolation and characterization of the genes encoding a lysine oxidase and a tedanalactam synthase.

The lysine oxidase and tedanalactam synthase genes were isolated from one of the Trichoderma sp. microorganisms isolated in Ecuador and the sequences determined.

Peptide sequences from purified tryptic peptides from F22844 lysine oxidase were obtained and used to design degenerate oligonucleotides to clone the lysine oxidase gene. From peptide P1 (SEQ ID NO:1) was deduced the antisense strand oligonucleotide N1 (SEQ ID NO:2), from peptide P2 (SEQ ID NO:3) was deduced the antisense strand oligonucleotide N2 (SEQ ID NO:4) and sense strand oligonucleotides N3, N4, and N5 (SEQ ID NOS:5,6,7). From peptide P3 (SEQ ID NO:8) was derived the sense strand oligonucleotides N6 (SEQ ID NO:9) and N7 (SEQ ID NO:10).

P1 (SEQ ID NO:1): Asp Ala Pro Pro Gln Pro Pro Lys Glu Asp Glu Leu Val Glu Leu Ile Leu Gln Asn Leu Ala Arg
N1 (SEQ ID NO:2): TC(AG) TC(CT) TC(CT) TTI GGI GG(CT) TG
P2 (SEQ ID NO:3): Gly Leu Asn Leu His Pro Thr Gln Ala Asp Ala Ile Arg
N2 (SEQ ID NO:4): ATIGC(AG)TCIGC(CT)TGIGTIGG(AG)TG
N3 (SEQ ID NO:5): CA(CT)CCIACICA(AG)GCIGA(CT)GCIAT
N4 (SEQ ID NO:6): AA(CT)CTICA(CT)CCIACICA(AG)GC
N5 (SEQ ID NO:7): AA(CT) TT(AG) CA(CT) CCI ACI CA(AG) GC
P3 (SEQ ID NO:8): Lys Gln Gln Ala Phe Gly Tyr Tyr Lys
N6 (SEQ ID NO:9): AA(AG)CA(AG)CA(AG)GCITT(CT)GGITA
N7 (SEQ ID NO:10): CA(AG)GCITT(CT)GGITA(CT)TA(CT)AA

To obtain a partial cDNA clone, nested sense and antisense degenerate oligonucleotides to three internal tryptic peptide sequences from the purified lysine oxidase were randomly combined in separate pair-wise PCR reactions with total cDNA from Trichoderma F22844 (Lee at al, 1988). The combination of sense strand oligonucleotides from peptide P3 (SEQ ID NO:8) and an antisense strand oligonucleotide from peptide P1 (SEQ ID NO:1) yield a PCR product of approximately 800 bp representing an internal portion of the lysine oxidase cDNA. More specifically, sense strand oligonucleotides N6 (SEQ ID NO:9) or N7 (SEQ ID NO:10) were combined with the antisense strand oligonucleotide N1 (SEQ ID NO:2) in a 50 μL PCR reaction containing 50 picomoles of each oligonucleotide, 1X TAQ buffer (Perkin-Elmer, Norwalk, Conn.), 1.5 mM $MgCl_2$, 660 μM dNTPs, and 0.5 units of Taq polymerase. The thermocycling profile was 1 cycle at 94° C. 5 minutes, 80° C. for 5 minutes in the absence of Taq polymerase followed by addition of Taq. After Taq addition, there were 3 cycles of 94° C. for 1 minute, 30 second ramp to 37° C. for 30 seconds, a 2.5 minute ramp to 72° C. for 2 minutes. This was followed by a PCR profile of 37 cycles of 94° C. for 1 minute, 48° C. for 1 minute, 72° C. for 2 minutes and terminated with a final incubation at 74° C. for 4 minutes.

Figure 1:
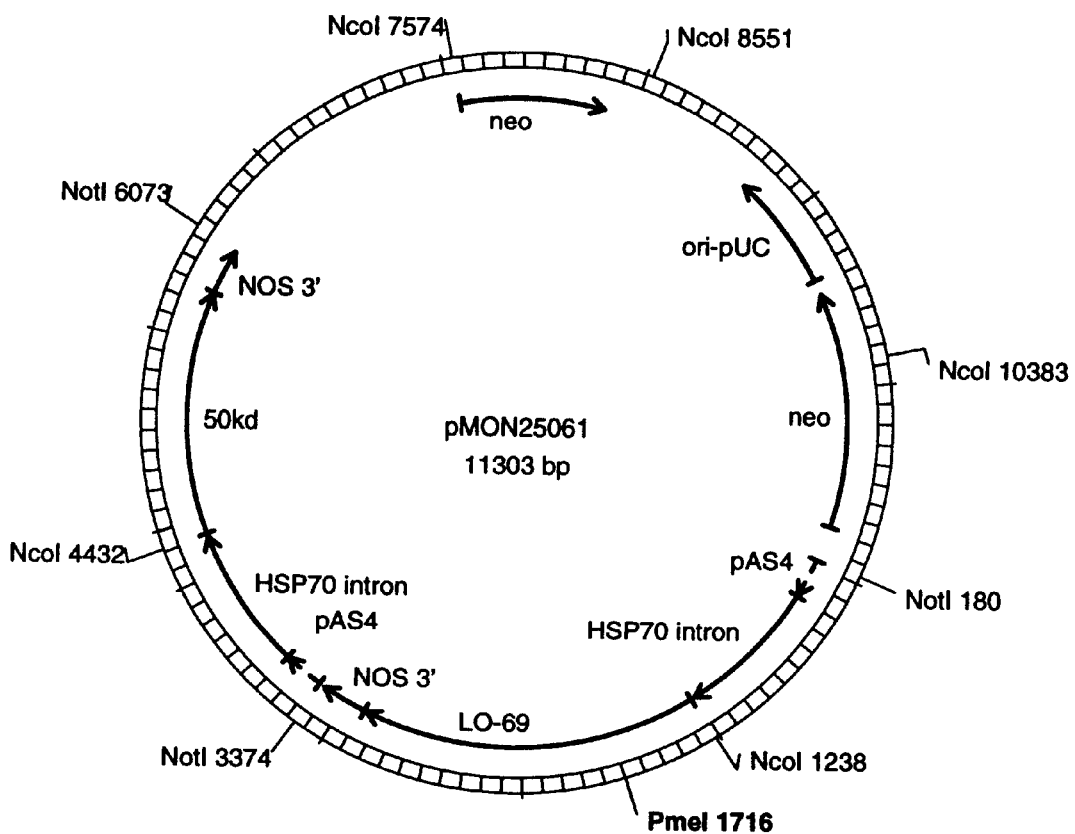
Figure 2:
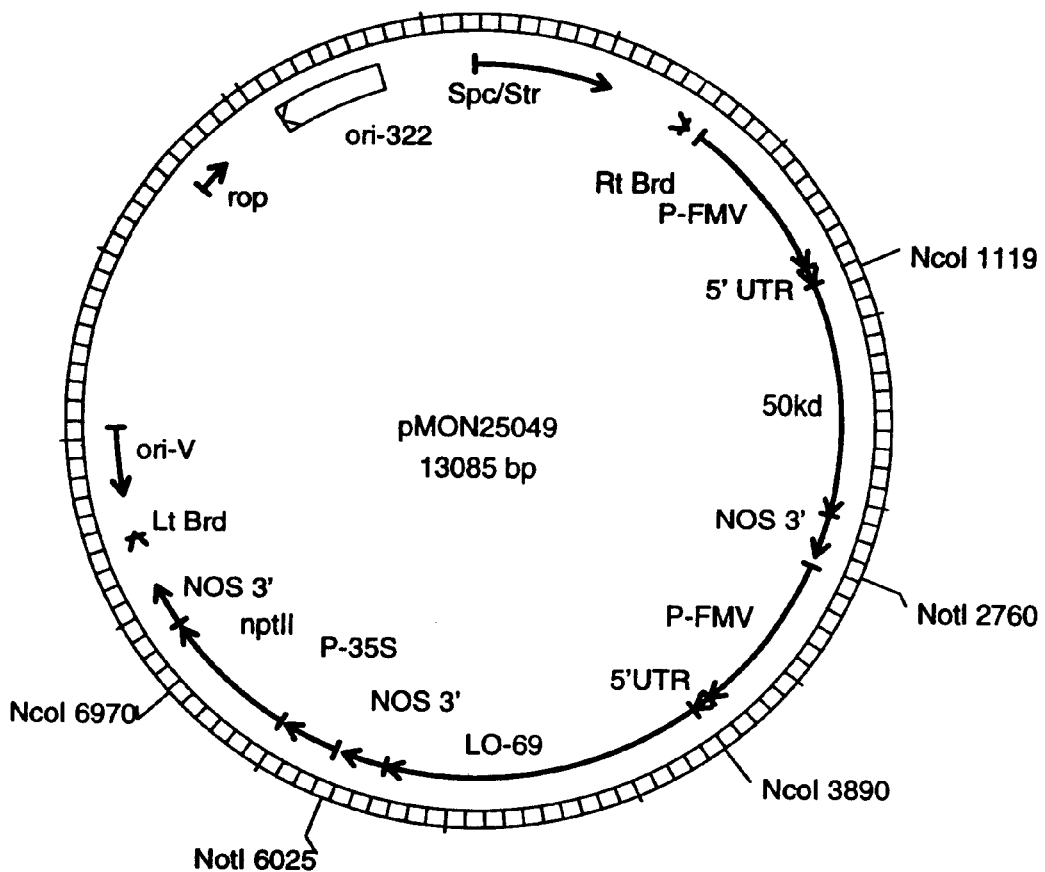
Figure 3:
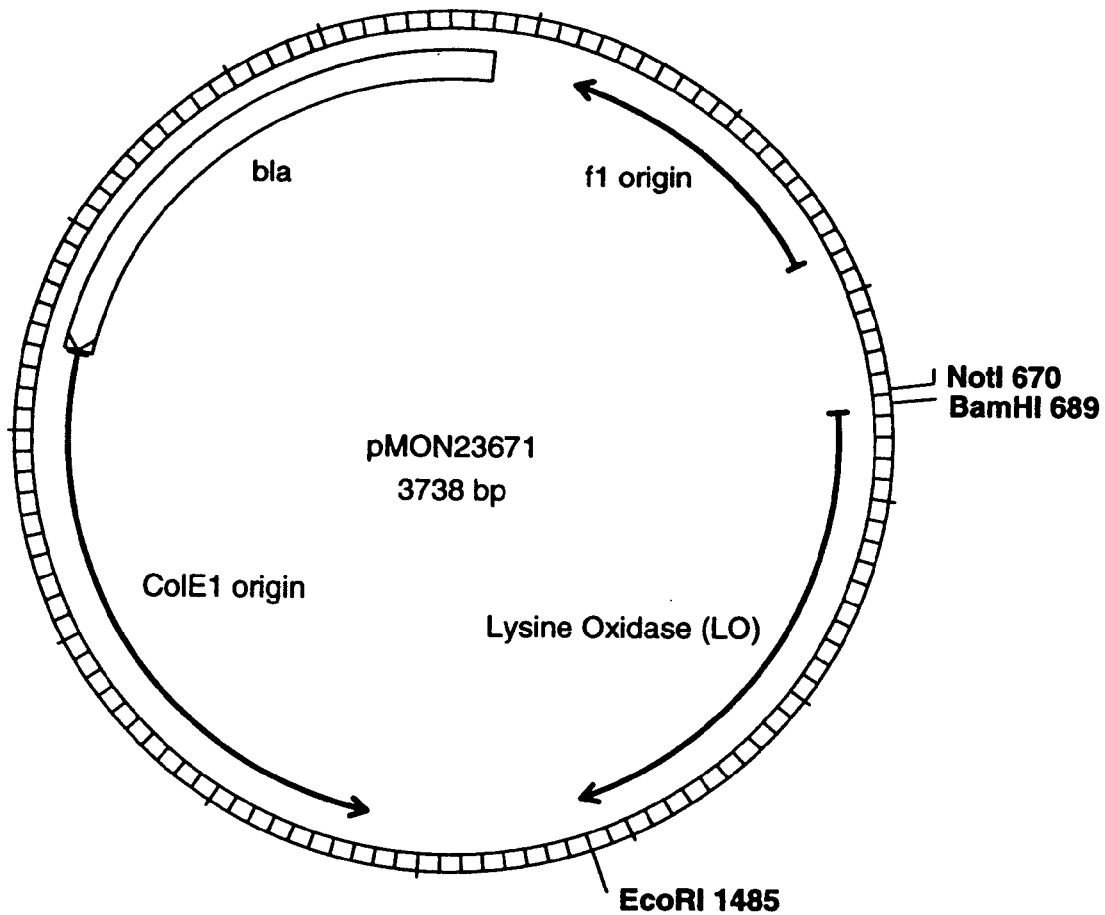
FIG. 3 represents a plasmid map of pMON23671 which contains an 800 base pair CDNA fragment representing a portion of a lysine oxidase gene.

To clone the internal lysine oxidase cDNA fragment, the 800 bp PCR fragment can then be ligated as a blunt ended fragment into a cloning vector such as pBSIIKS+ (Stratagene, La Jolla, Calif.) digested with SmaI to produce plasmid pMON23671 (FIG. 3). DNA sequencing of this fragment reveals DNA sequences coding for peptide fragments P2 (SEQ ID NO:3) and P4 (SEQ ID NO:11) as well as portions of peptide fragments P1 (SEQ ID NO:1) and P3 (SEQ ID NO:8), confirming the identity of the clone as a lysine oxidase cDNA fragment (SEQ ID NO:12). Note that the first residue of the P3 (SEQ ID NO:8) was later found to be a leucine rather than a lysine upon review of both the DNA and protein sequencing data. The oligonucleotide N7 (SEQ ID NO:10) apparently still hybridized and functioned under the conditions described since only the first two nucleotides at its 5 prime end are mismatched.

It is useful to identify a complete cDNA sequence to determine if the genomic DNA contains introns that disrupt the coding sequence. Such introns could inhibit expression of the cloned gene in heterologous systems such as plants. To obtain the complete sequence of the lysine oxidase cDNA, the standard RACE (Rapid Amplification of cDNA Ends) procedure (Frohman et al., 1988) was used to extend the cDNA sequence from the internal core cDNA sequence present in pMON23671.

Figure 4:
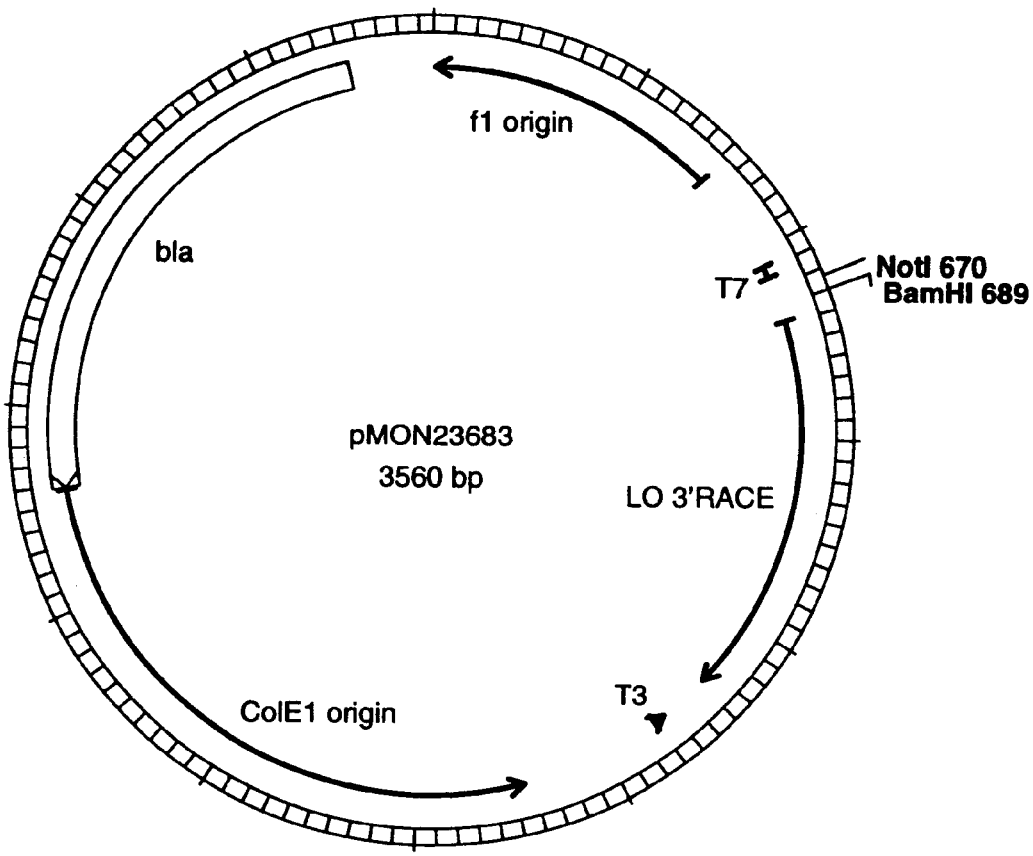
FIG. 4 represents a plasmid map of pMON23683 which contains a 650 base pair cDNA fragment representing a portion of the 3' end of a lysine oxidase gene.

To recover the 3' end, cDNA synthesized from poly A enriched F22844 with the 3' Race Adapter primer (Gibco-BRL, Gaithersburg, Md.) was PCR amplified with the Universal Amplification Primer (Gibco-BRL, Gaithersburg, Md.) and the lysine oxidase sense strand oligonucleotide N8 (SEQ ID NO:13). This PCR reaction yields a product of approximately 700 bp that can be re-amplified with the internally nested oligonucleotide is N9 (SEQ ID NO:14) to yield a PCR product of approximately 650 bp. The 650 bp product was subsequently subcloned as a blunt ended fragment into EcoRV digested pBSIIKS+ to yield pMON23683 (FIG. 4). Subsequent sequencing of this cDNA clone displayed uninterrupted homology to the genomic lysine oxidase genomic DNA sequence (SEQ ID NO: 15).

N8 (SEQ ID NO:13): ACCTCTACGAACTTGCGTTTACC
N9 (SEQ ID NO:14): CAACTCGCATTGGATCGTTGGTG

Figure 5:
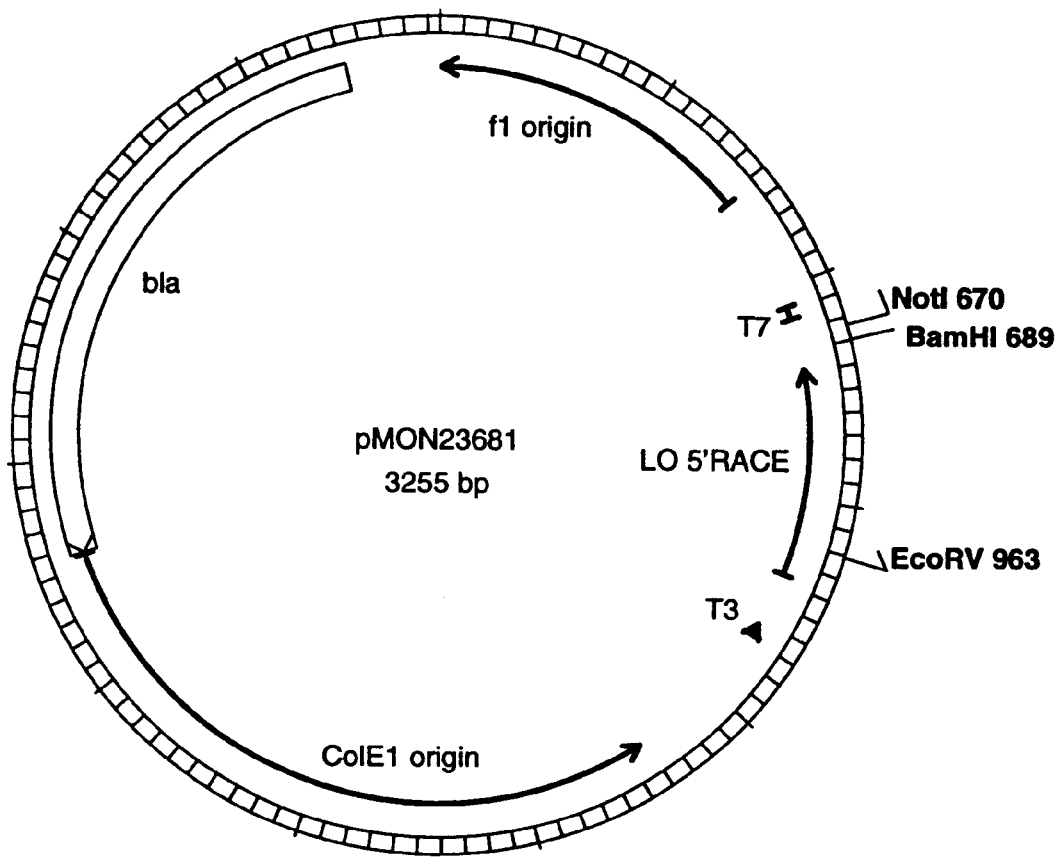
FIG. 5 represents a plasmid map of pMON23681which contains a 300 base pair cDNA fragment representing a portion of the 5' end of a lysine oxidase gene.

To recover the 5' end, two sets of 5' RACE reactions were performed. In the first set, poly A enriched RNA from F22844 was reverse transcribed into cDNA with oligonucleotide N 10 (SEQ ID NO:16) and dC tailed with Terminal Transferase (Gibco-BRL, Gaithersburg, Md.). This cDNA was then amplified first with oligonucleotide N11 (SEQ ID NO:17) and the Anchor Primer or AP (Gibco-BRL, Gaithersburg, Md.). This PCR reaction was subsequently re-amplified with oligonucleotide N12 (SEQ ID NO:18) and the Universal Amplification Primer or UAP (Gibco-BRL, Gaithersburg, Md.) to yield a 300 bp product which was blunt end cloned into EcoRV digested pBSIIKS+ to yield pMON23681 (FIG. 5). Sequence analysis of this cDNA clone (SEQ ID NO:19) revealed uninterrupted homology to the genomic lysine oxidase genomic DNA sequence. However, a second set of 5' RACE reactions was then needed to recover the remaining 5' portion of the lysine oxidase cDNA sequence. This was accomplished by use of oligo dT primed first strand cDNA as template, followed by one round of PCR amplification with the AP and N13 (SEQ ID NO:20), and completed with a final round of PCR amplification using the preceding PCR reaction product as template with the UAP and N14 (SEQ ID NO:21) oligonucleotides as primers. The final 520 bp, 5 prime RACE product was subcloned into the PCR II vector (Invitrogen, San Diego, Calif.) to yield pMON25433 and sequenced to obtain the remaining cDNA sequence (SEQ ID NO:22). This sequence also displayed uninterrupted homology to the lysine oxidase genomic sequence.

N10 (SEQ ID NO:16) CAT GTC GTC GAC GAG CAT GAG C
N11 (SEQ ID NO:17) CAT CGA ACC CTT TGT CGA AGT CC
N12 (SEQ ID NO:18) CAG CAA GCT TCT CTT TGT AAT ACC C
N13 (SEQ ID NO:20) GTC GAA GTC CTC AGC CAG CTT CTC TTT GTA A
N14 (SEQ ID NO:21) CAT GCT GGG GAT GTC AGG

To obtain a complete clone of the genomic DNA encoding the lysine oxidase, a lambda phage genomic DNA library (Frischauf et al., 1987) derived from F22844 was screened by hybridization with the lysine oxidase partial cDNA fragment. In brief, approximately 20,000 plaque forming units from the library were plated, transferred to filters, and probed with radiolabelled lysine oxidase cDNA fragment (SEQ ID NO:12) which had been isolated from pMON23671. Briefly, filters were hybridized with a $^{32}$P labeled probe (Feinberg and Vogelstein, 1983) with a specific activity of approximately $2 \times 10^8$ DPM/μg in 5×SSC, 5×Denhardts, 0.1% SDS, 50% formamide, and 500 μg/mL DNA at 42° C. for 18 hours, washed twice in 2×SSC, 0.1% SDS for 15 minutes at 25° C. or room temperature, washed twice in 0.1×SSC, 0.1% SDS for 20 minutes at 60° C. and autoradiographed. Positive or hybridizing plaques were then picked, re-plated, and re-probed until a purified isolate consisting of only of hybridizing plaques is obtained. Five independent, hybridizing lambda phage clones were obtained.

Figure 6:
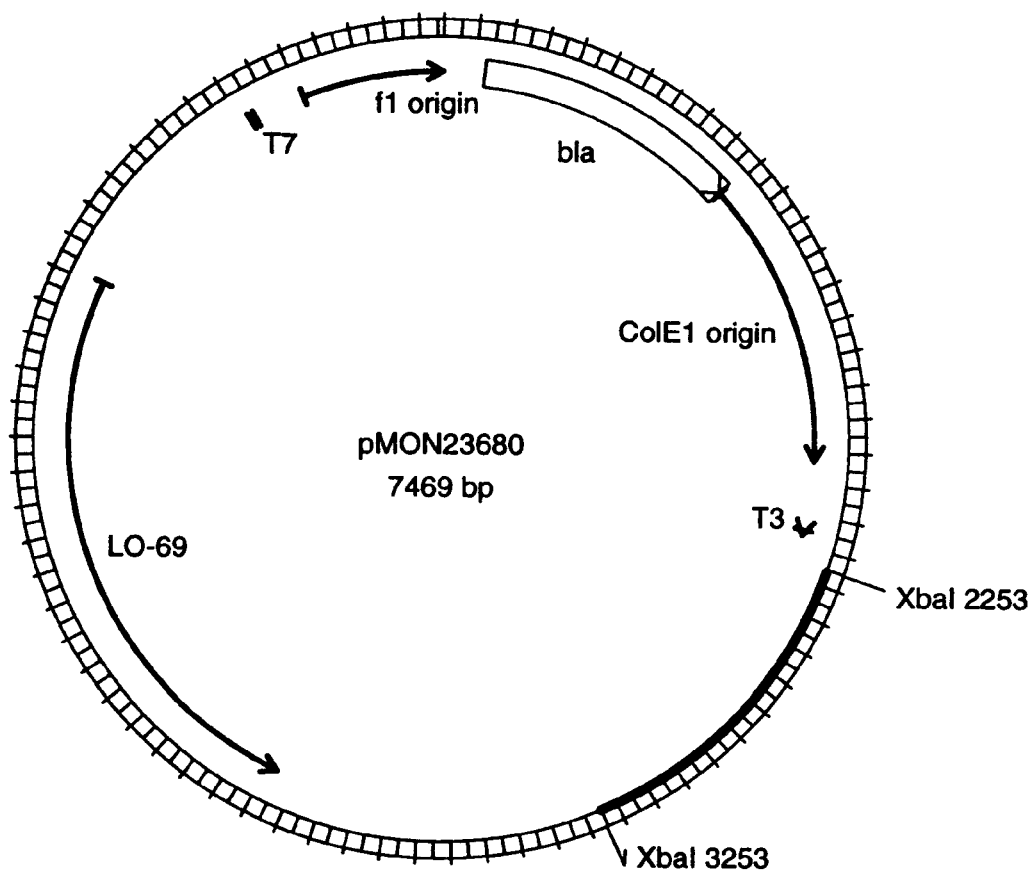
FIG. 6 represents a plasmid map of pMON23680 which contains a genomic DNA fragment encoding a lysine oxidase gene.
Figure 7:
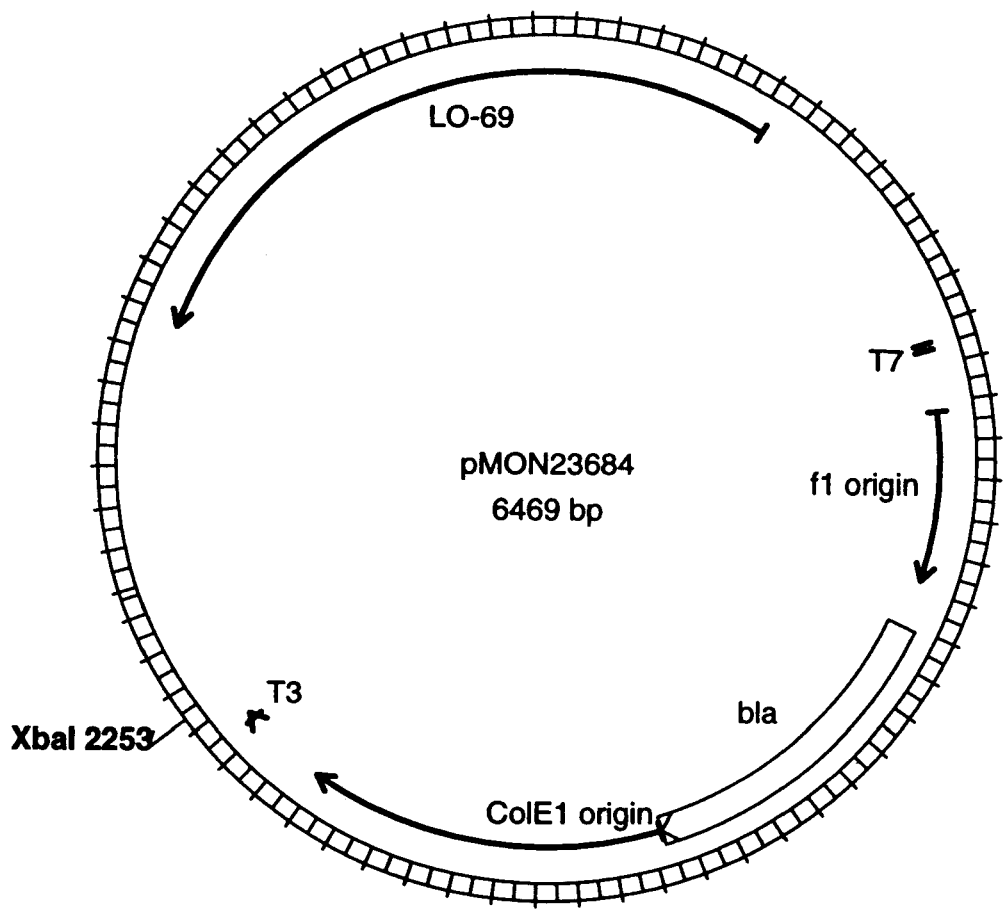
FIG. 7 represents a plasmid map of pMON23684 which contains a genomic DNA fragment encoding a lysine oxidase gene.

The DNA from the purified lambda phage was then prepared by standard procedures and analyzed by both direct DNA sequencing and southern blot techniques. Sequencing of the lambda genomic clones reveals essentially complete sequence homology to the partial lysine oxidase cDNA clone in pMON23671 and to one another, indicating that the clones are independent isolates of the same gene. Southern blot analysis of lambda phage genomic DNA digested with BamHI indicated that all of the clones carried a common cross hybridizing BglII fragment of approximately 5 kb and that genomic DNA of the F22844 has a similar band. The 5 kb BglII fragment from the lambda phage digest was subsequently isolated and cloned into the BamHI site of pBSIIKS+(Stratagene, La Jolla, Calif.) to yield pMON23680 (FIG. 6). An internal 1.0 kb XbaI fragment restriction mapped to the 3' end of the genomic DNA was deleted from pMON23680 to yield pMON23684 (FIG. 7). The complete sequence of the genomic DNA encoding the lysine oxidase gene is given (SEQ ID NO:15).

The complete sequence of the genomic clone of the F22844 lysine oxidase gene was determined and compared to the sequence of the lysine oxidase cDNA. Comparison of the genomic and cDNA sequence indicates that the lysine oxidase gene has no introns within its coding region. More specifically, the DNA sequences of the genomic DNA (in lambda clone 56-3 and derived pMONs 23680 and 23684) were determined by automated sequencing of both strands (Prism DyeDeoxy Cycle Sequencing—Applied Biosystems, Foster City, Calif.) and confirmed with manual sequencing (Sanger dideoxy chain termination). Sequences of the cDNA fragments in pMONs 23671, 23681, 23683 and pMON25433 were obtained by automated sequencing as well as by manual sequencing for pMON25433.

Analysis of the lysine oxidase genomic sequence shows a single open reading frame encoding a 617 amino acid residue ORF of approximate predicted $M_r$ 69,400. Since the native protein has an apparent $M_r$ 56,000 this ORF encodes a pre-protein that is post-translationally modified to yield the mature protein. N-terminal sequence data and mass spectroscopy data indicate that approximately 77 amino acid residues are cleaved from the N-terminus to yield the mature lysine oxidase protein of approximate $M_r$ 60,000.

A search of the SWISS PROT database with the entire 617 amino acid residue lysine oxidase ORF (SEQ ID NO:46; predicted $M_r$=69,400) encoded by the genomic sequence revealed homology of the Trichoderma lysine oxidase to the Neurospora L-amino acid oxidase (LAO) precursor protein (Niedermann and Lerch, 1990). The overall homology score was 24% identity, 50% similarity over 606 residues with the highest conservation in a region identified as a FAD binding site (8 of 9 contiguous residues). Both lysine oxidase and LAO are apparently synthesized as proproteins since the first 129 amino acids of the non-secreted (intracellular) LAO proprotein are removed to yield the mature LAO (Niedermann and Lerch, 1990). This result suggests that the LAO of Neurospora or other L-amino acid oxidases may be combined with the F22844 $M_r$ 50,000 protein or other proteins to yield control of other insects.

Figure 8:
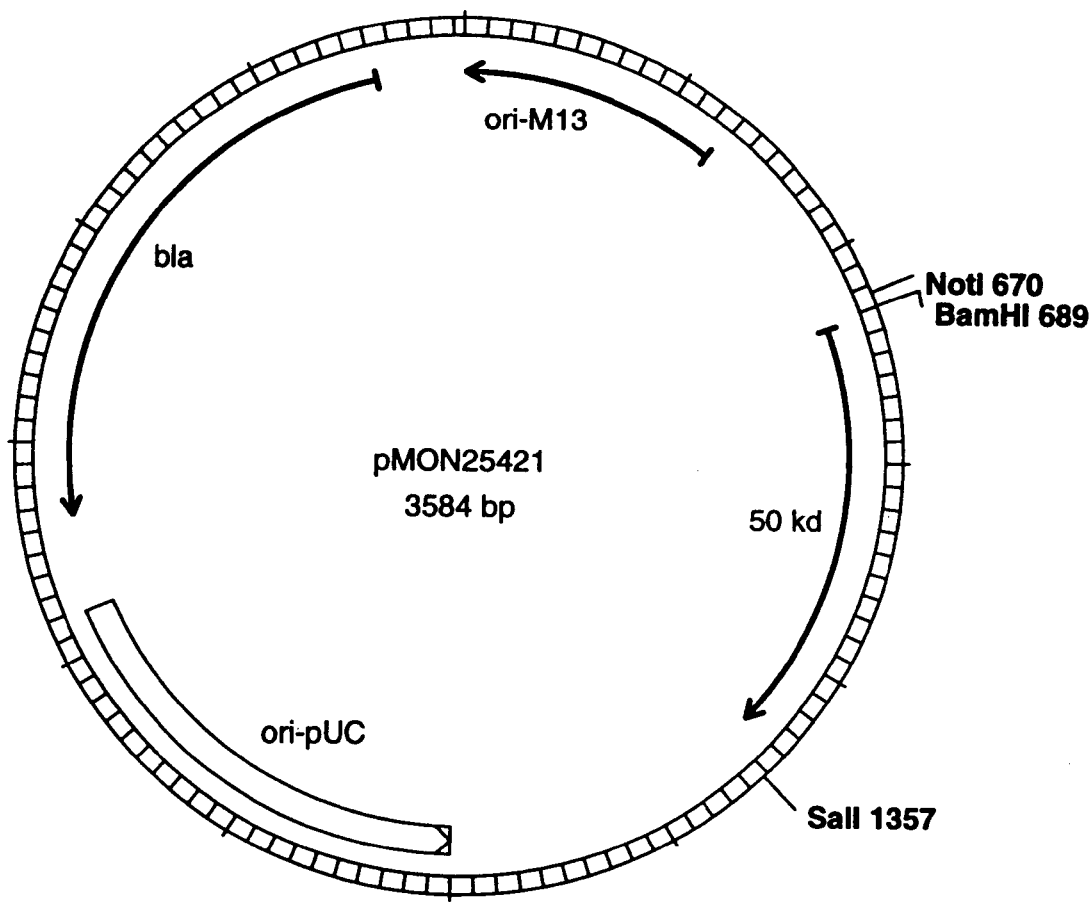
FIG. 8 represents a plasmid map of pMON25421 which contains a cDNA fragment representing a partial coding sequence of a tedanalactam synthase gene.

The full length tedanalactam synthase cDNA was isolated in stages using PCR based protocols of mixed oligonucleotide primed amplification of cDNA (MOPAC) (Lee et al., 1988) and rapid amplification of cDNA ends (R.A.C.E.) (Frohman et al., 1988). First strand cDNA was generated from poly A+ RNA isolated from 4 day old culture of F22844 and served as templates for the MOPAC and RACE reactions. The first 5 prime (sense) gene specific amplification primer (GSP), primer N15 (SEQ ID NO:23), was designed from the protein sequence P5 (SEQ ID NO:24) obtained from tryptic peptide fragment 11. A second nested 5 prime GSP, primer N16 (SEQ ID NO:25), was designed from protein sequence P6 (SEQ ID NO:26) derived from tryptic fragment 9. The 3 prime (antisense) GSP, primer N17 (SEQ ID NO:27), was designed from the protein sequence P7 (SEQ ID NO:28) obtained from tryptic peptide fragment 16. A 623 bp partial cDNA fragment (SEQ ID NO:29) was obtained from an RT-PCR reaction with primers N16 (SEQ ID NO:25) and N17 (SEQ ID NO:27), and subcloned into pBluescript II KS+ (Stratagene, La Jolla, Calif.) at the SmaI site (blunt ligation) resulting in pMON25421 (FIG. 8). The partial cDNA was sequenced and the deduced protein sequence matched the protein sequence obtained from tryptic fragments 9, 7, and 16 (SEQ ID NO:26, SEQ ID NO:30,SEQ ID NO:28).

N15 (SEQ ID NO:23): GAR CAR AAY AAY TTY TTY AAY CAY GC

P5 (SEQ ID NO:24): Val Val Val Leu Glu Gln Asn Asn Phe Phe Asn His Ala Gly Ser Ser Asn Asp Leu Ala

N16 (SEQ ID NO:25): ATG TAY ACI GAR CAY TAY ATG

P6 (SEQ ID NO:26): Thr Met Tyr Thr Glu Asp Tyr Met Ala Asp Leu Ala Lys

N17 (SEQ ID NO:27): GG IGC RAA YTG RAA CCA CAT

P7 (SEQ ID NO:28): Gly Thr Ile Phe Pro Ser Met Trp Phe Gln Phe Ala Pro Asp Lys

P8 (SEQ ID NO:30): Leu Gly Met Thr Tyr Gln Glu Met Ser Ala Lys

Figure 9:
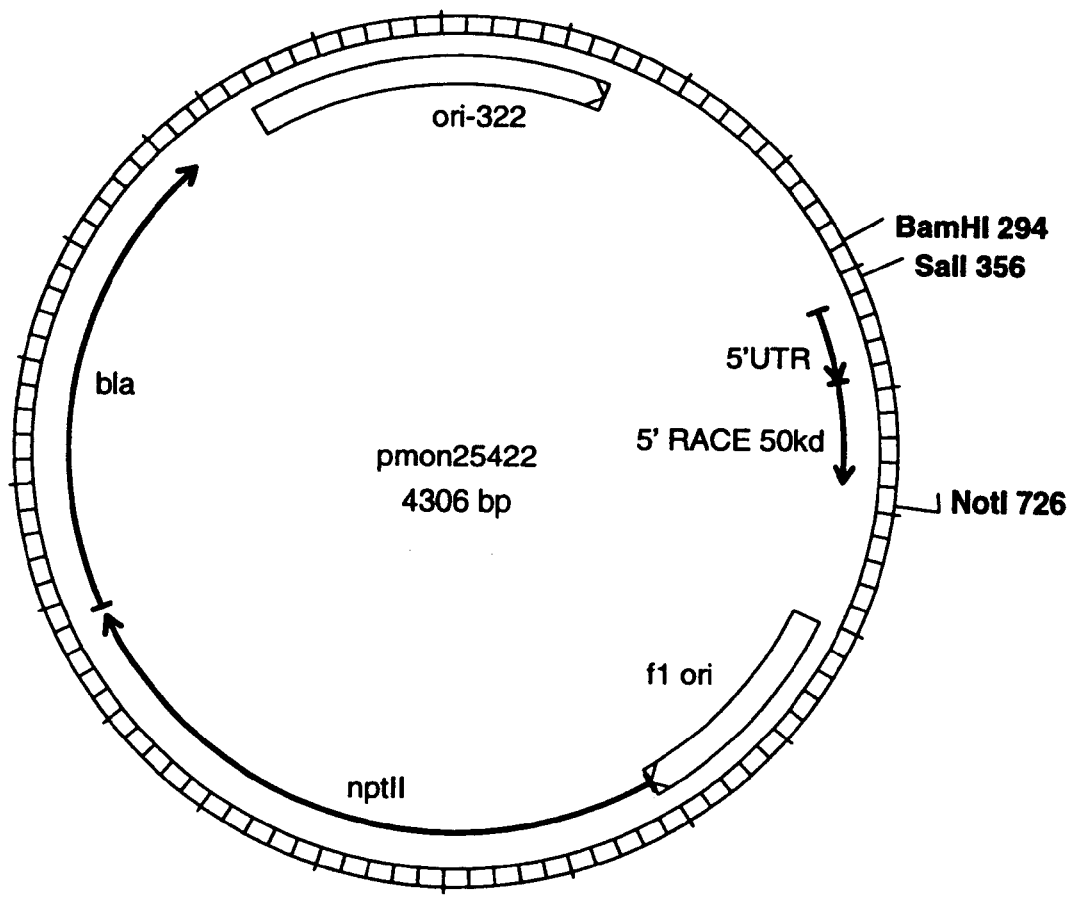
FIG. 9 represents a plasmid map of pMON25422 which contains a cDNA fragment representing a partial coding sequence of a tedanalactam synthase gene.

RACE was used to identify the remaining 5 prime and 3 prime cDNA sequence of the tedanalactam synthase gene. 5 prime RACE was performed according the Gibco-BRL kit using P6 (SEQ ID NO:26) derived gene specific antisense primers N18 (SEQ ID NO:31) and N19 (SEQ ID NO:32). The 380 bp, 5 prime RACE product (SEQ ID NO:33) was subcloned into the PCR II vector (Invitrogen, San Diego, Calif.) resulting in pMON25422 (FIG. 9). To recover the 3 prime portion of the cDNA, 3 prime RACE was performed using a P6 (SEQ ID NO:26) derived gene specific sense primer N20 (SEQ ID NO:34) and the Universal Amplification Primer (Gibco-BRL, Gaithersburg, Md.) which generated a 1423 base pair fragment. The 1423 bp fragment 3 prime race product (SEQ ID NO:35) was subcloned into PCR II vector (Invitrogen, San Diego, Calif.) to yield pMON25423.

The full length 50 kb cDNA was generated by overlap PCR (Horton et al., 1989) using F22844 first strand cDNA as template and primers:

1) N21 (SEQ ID NO:36), a 5 prime sense primer that introduces BglII and NcoI restriction sites at the start codon (ATG) (primer mr50000-1)
2) N22 (SEQ ID NO:37) sense and N23 (SEQ ID NO:38) antisense 31-mers (primer mr50000-2 and mr50000-3) to remove the internal NcoI site.
3) N24 (SEQ ID NO:39) an oligonucleotide that introduces a EcoRI and HindIII restriction sites 3 prime to the stop codon that is located 1363 bp downstream of the start codon (ATG).

Figure 10:
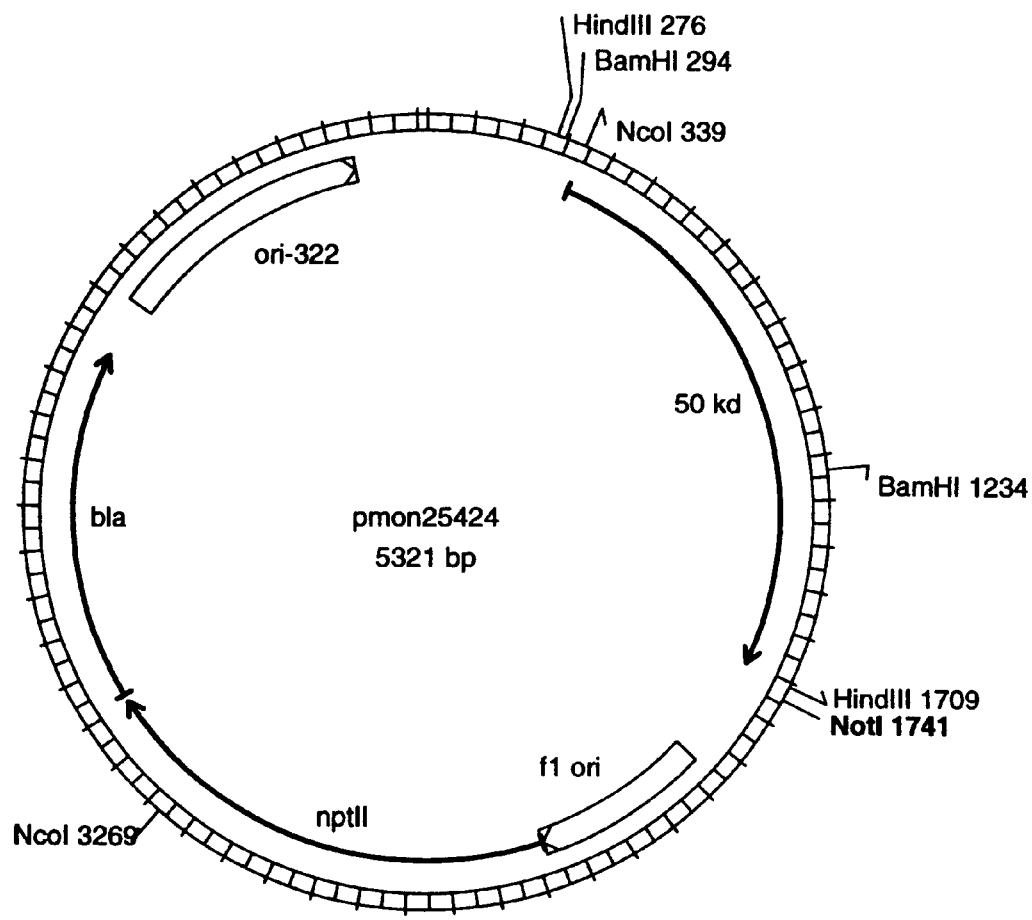
FIG. 10 represents a plasmid map of pMON25424 which contains a full length cDNA representing the coding sequence of a tedanalactam synthase gene.

The engineered full length cDNA, 1385 bp PCR product (SEQ ID NO: 40), was subcloned into PCR II vector (Invitrogen, San Diego, Calif.) resulting in pMON25424 (FIG. 10). The deduced translated protein sequence is shown (SEQ ID:41).

N21 (SEQ ID NO:36): GGG AGA TCT CCA TGG CAG ACG AAA TCT

N22 (SEQ ID NO:37): GGC TTT CCA GCA CTT CCT TGG GGC CCT CCA A

N23 (SEQ ID NO:38): TTG GAG GGC CCC AAG GAA GTG CTG GAA AGC C

N24 (SEQ ID NO:39): CCC AAG CTT GAA TTC ACT TTC TTC TAT TGC C

Genomic DNA was isolated from the fungal pellet of a 5 day old liquid culture of F22844 (Fedoroff et al. 1983). Southern blot analysis indicated that the gene encoding tedanalactam synthase was a single copy gene and mapped to an 8.0 kb BglII fragment. A F22844 genomic library was constructed from genomic DNA partially digested with MboI ligated into the BamHI site of the lambda EMBL3 vector (Frischauf et al., 1987). pMON 25421 cDNA insert was used to screen 48,000 plaque forming units from the primary library and nine positive overlapping clones were identified. The tedanalactam synthase gene was localized to a 9.0 kb SalI fragment. In three of the lambda clones, the gene mapped to one of the vector arms indicating that partial MboI digestions of F22844 genomic DNA used in the construction of the library had created truncation of the 9.0 kb SalI fragment to a 6.0 kb, 4.4 kb and 2.5 kb. The 4.4 kb SalI fragment was subcloned into pBluescript II KS+ (Stratagene, La Jolla, Calif.) resulting in pMON25425. The insert was sequenced and contained the complete 50 kb genomic clone with 5 introns (SEQ ID NO:42).

Example 6

This example illustrates bioactivity of lysine oxidase and tedanalactam synthase derived from cloned genes against western corn rootworm.

The lysine oxidase and tedanalactam synthase genes can be isolated from novel sources or known sources. These genes may than be used to transform bacterial, yeast or plant cells, resulting in the production of lysine oxidase (or lysine oxidase proprotein) and tedanalactam synthase and permitting use of the methods of this invention. Examples of how this could be done for the lysine oxidase and tedanalactam synthase genes from fungal isolate F22844 are given below.

To introduce restriction endonuclease sites permitting expression of the lysine oxidase structural gene in transformed microorganisms and plants, the cloned genomic DNA sequence of the F22844 lysine oxidase gene (SEQ ID NO:15 in pMON23680 or 23684) was subjected to PCR mediated site-directed mutagenesis. Briefly, about 100 picograms of pMON23680 in a 100 $\mu$L reaction containing 1×Pfu buffer (Stratagene, La Jolla, calif.), 100 $\mu$M dNTPs, 0.5 $\mu$M oligonucleotide primer N25 (SEQ ID NO:43), 0.5 $\mu$M oligonucleotide primer N26 (SEQ ID NO:44), 2.5 units of Pfu polymerase (Stratagene, La Jolla, Calif.) was overlaid with mineral oil and subjected to thermal cycling in a Perkin Elmer Model 480 DNA Thermo Cycler. The thermal cycling profile was 1 cycle at 94° C. for 1.5 minutes, 50° C. for 1 minute, 74° C. for 3 minutes followed by 25 cycles of 94° C. for 1 minute, 50° C. for 1 minute, 74° C. for 2 minutes and terminated with final cycle of 94° C. for 1 minute, 50° C. for 1 minute, 74° C. for 15 minutes. The PCR reaction product of approximately 1,900 bp was electrophoresed on an agarose gel, purified (Qiagen, Chatsworth, Calif.), and digested with restriction endonucleases NcoI and EcoRI. The sequence of the resultant PCR product is given (SEQ ID NO:45). Note that the amino acid sequence of the lysine oxidase $M_r$ 69,400 proprotein (SEQ ID NO:46) encoded by the mutagenized DNA sequence is identical to the deduced translation product of unmutagenized lysine oxidase genomic sequence (SEQ ID NO:15; translation start at base number 663, translational stop at base number 2513).

N25 (SEQ ID NO:43): TTGCAAACCATGGACAATGT-TGACTTTGCTGAATC

N25 (SEQ ID NO:44): GCCGTAGTACCGAATTCTTAT-TAAATCTTCACC

Convenient restriction sites for placing the tedanalactam synthase gene into plant expression vectors were also introduced by PCR site-directed mutagenesis as described previously.

Figure 11:
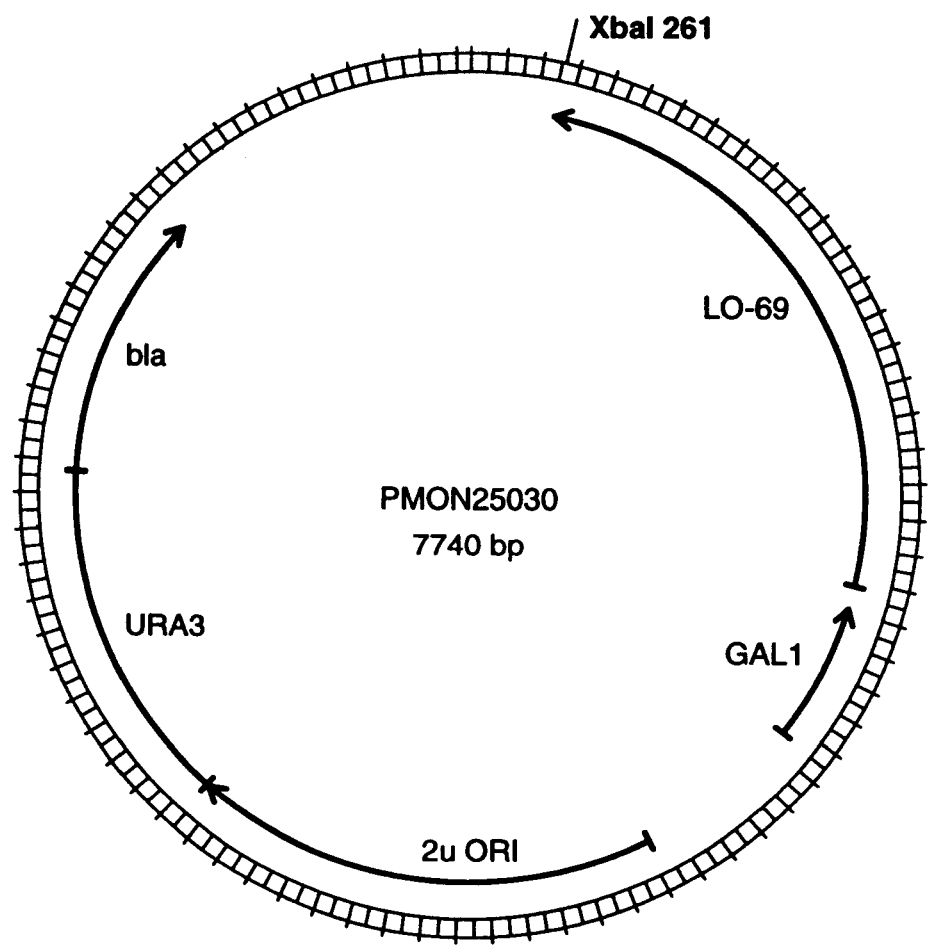
FIG. 11 represents a plasmid map of pMON25030 which represents a yeast expression vector containing a DNA fragment encoding a lysine oxidase.
Figure 12:
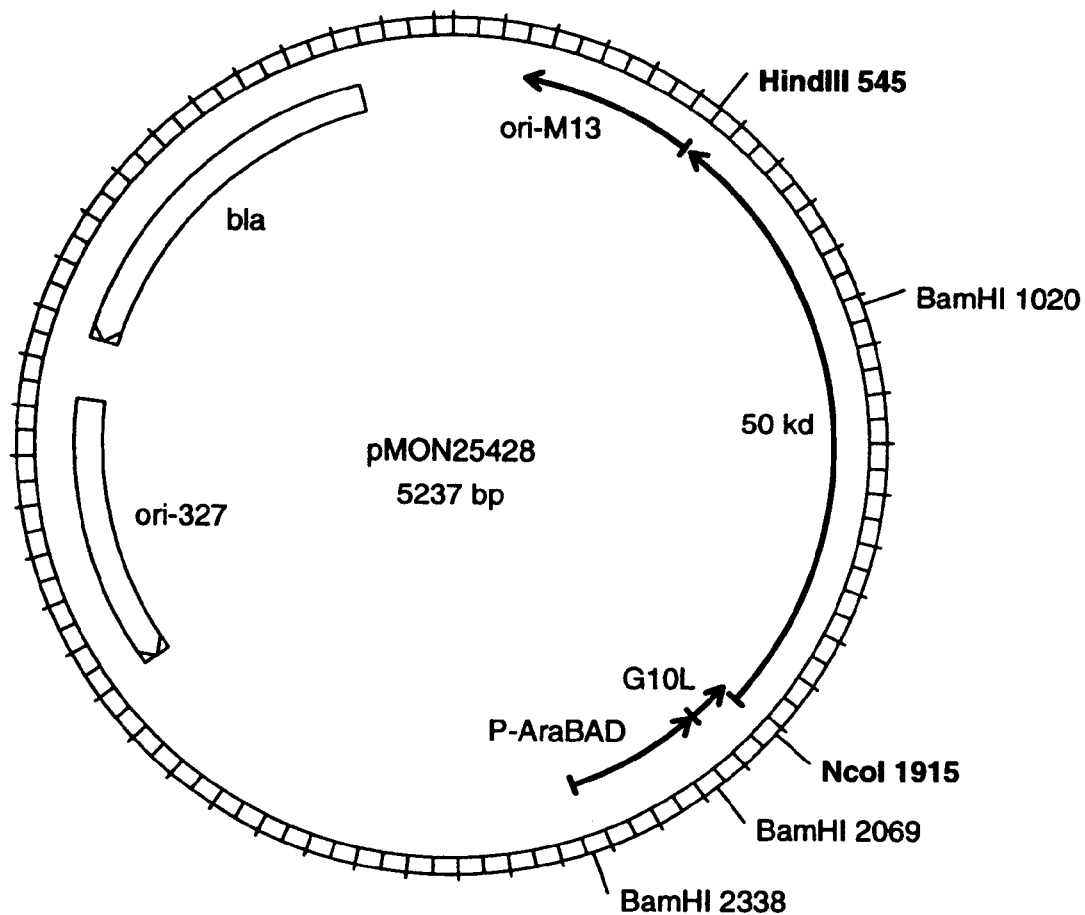
FIG. 12 represents a plasmid map of pMON25428 which contains a cDNA fragment encoding a tedanalactam synthase under the control of an arabinose inducible promoter.
Figure 13:
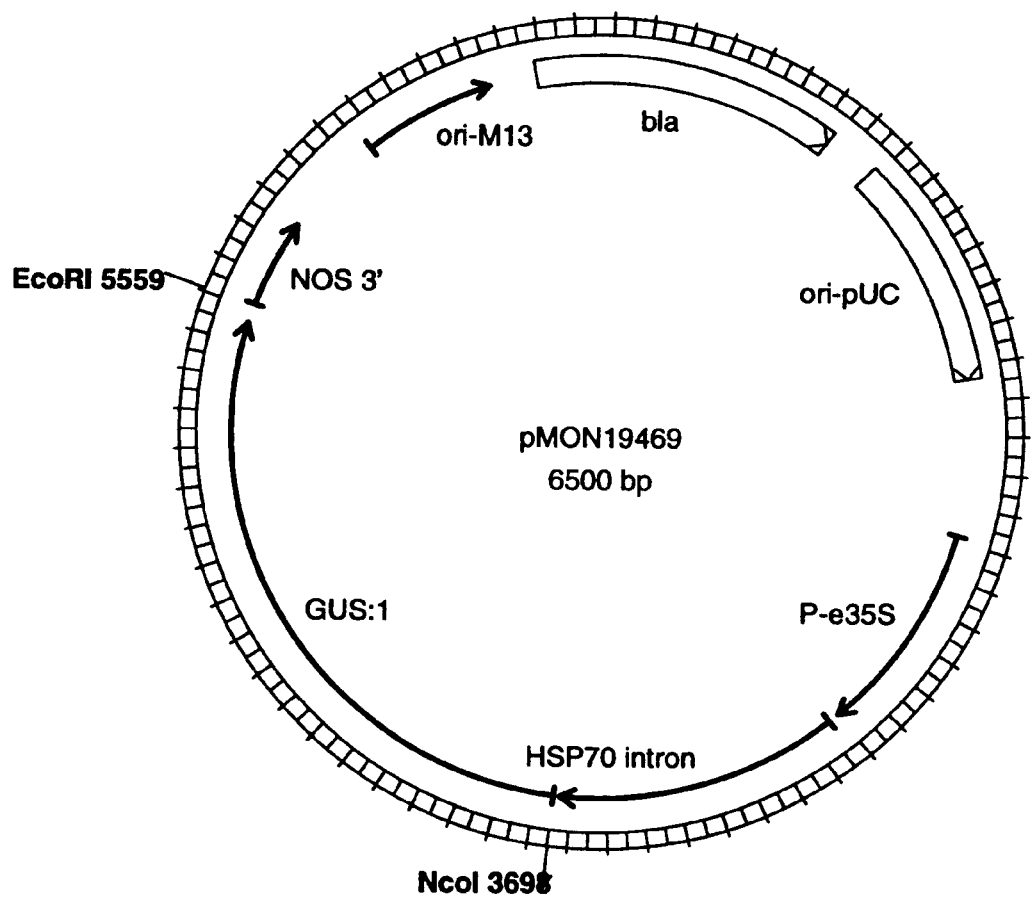
FIG. 13 represents a plasmid map of pMON19469 which is a monocot expression vector containing a cauliflower mosaic virus 35S promoter, an hsp70 intron, and a nopaline synthase polyadenylation sequence.
Figure 14:
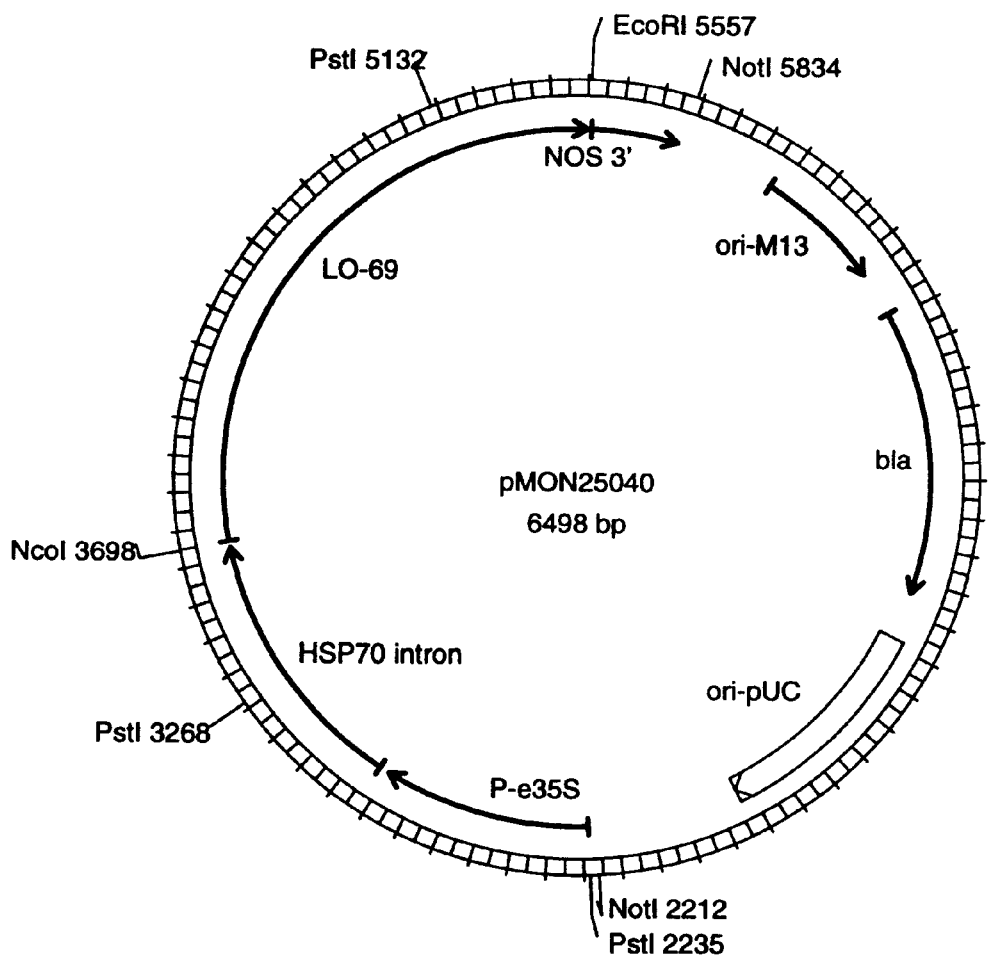
FIG. 14 represents a plasmid map of pMON25040 which contains a DNA sequence encoding a lysine oxidase variant under the control of a cauliflower mosaic virus 35S promoter.
Figure 15:
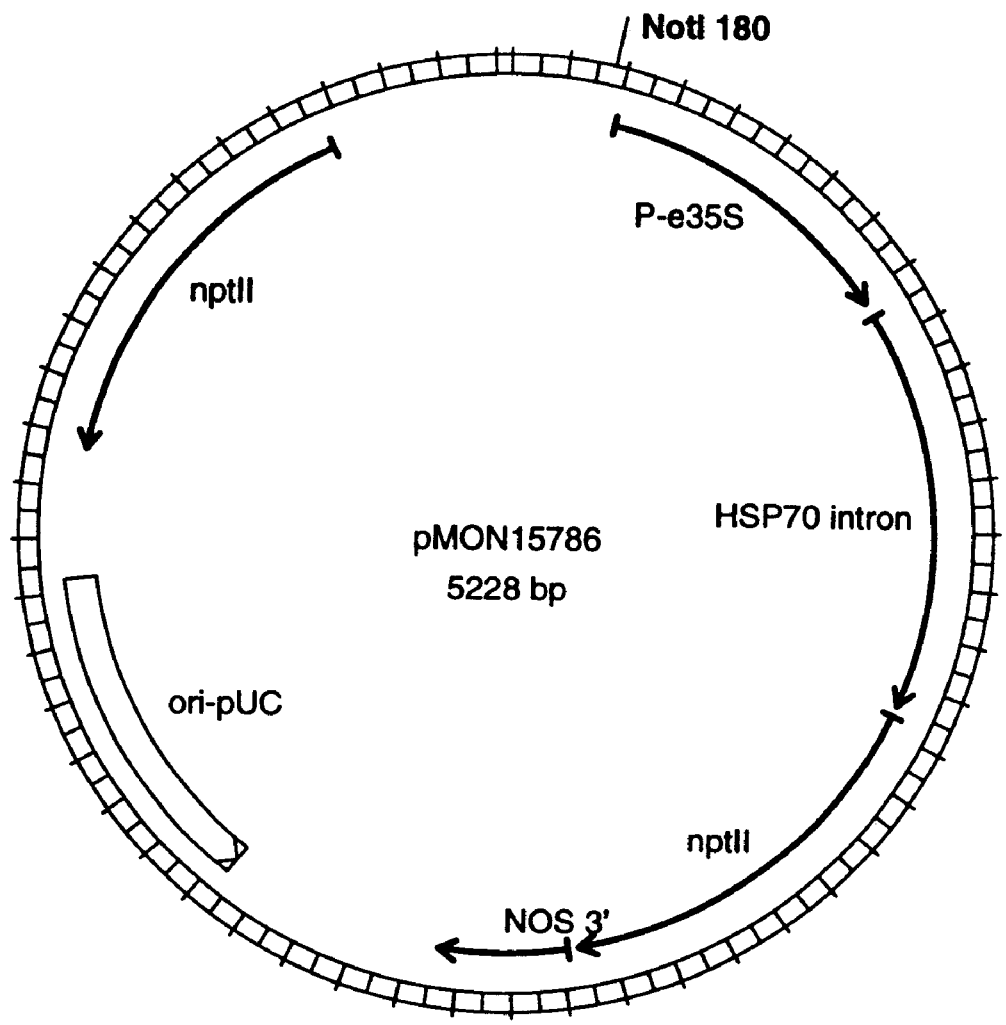
FIG. 15 represents a plasmid map of pMON15786 which is a plant transient expression vector containing a neomycin phosphotransferase coding sequence fused to an hsp70 intron, under the control of a cauliflower mosaic virus 35S promoter.
Figure 16:
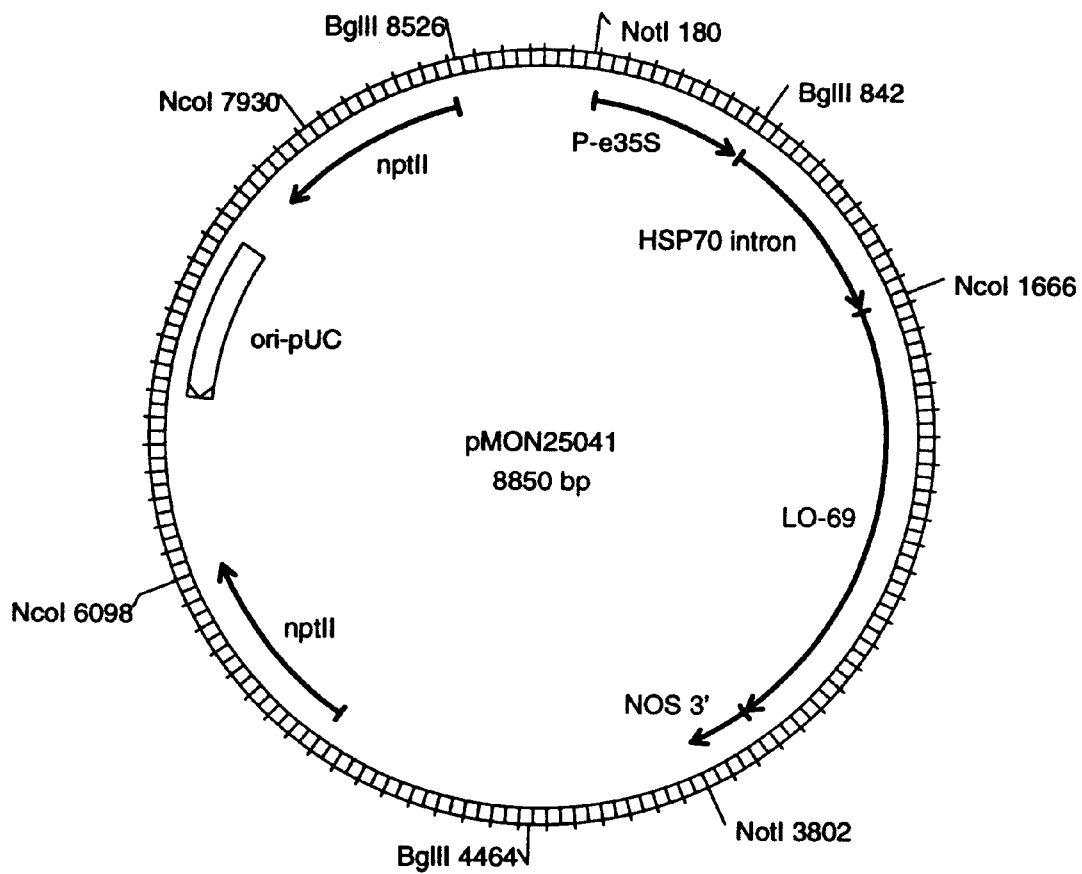
FIG. 16 represents a plasmid map of pMON25041 which contains a DNA fragment encoding a lysine oxidase variant under the control of a cauliflower mosaic virus 35S promoter.

To obtain functional lysine oxidase protein from the cloned gene, the lysine oxidase gene was engineered for expression in a heterologous yeast system. The yeast expression construct, pMON25030 (FIG. 11), was made by cloning a PCR generated fragment encoding the lysine oxidase $M_r$ 69,400 proprotein (SEQ ID NO:46) into a pYES2 yeast expression plasmid (Invitrogen, San Diego, Calif.). The PCR fragment (approximately 1.9 kb) was generated by using two primers, N26 (SEQ ID NO:47) and N27 (SEQ ID NO:48) and PCR amplifying a segment of DNA from pMON23680 (SEQ ID NO:15). Each primer carried a unique restriction site which provided directional cloning of the fragment into the pYES2 vector under GAL1 promoter control. Primer N26 (SEQ ID NO:47) carried a BglII site while N27 (SEQ ID NO:48) had an XbaI site. The resulting PCR fragment was digested with BglII and XbaI and cloned into BamHI and XbaI sites of the pYES2 vector. Note that the amino acid sequence of the lysine oxidase $M_r$ 69,400 proprotein (SEQ ID NO:46) encoded by this DNA fragment is not affected by introduction of these restriction sites.

N26 (SEQ ID NO:47): CCCAGATCTATATTTGCAAA-CATGGACAATG

N27 (SEQ ID NO:48): GGGTCTAGACTAACAAACAT-CACACTTTCTATG

Yeast (*Saccharomyces cerevisiae*) transformed with pMON25030 were grown in the presence of galactose and shown to produce enzymatically active lysine oxidase. Yeast transformed with pMON25030 had soluble lysine oxidase activity in both disrupted cell pellets and cell free culture media. Culture media incubated for five days of galactose induction was found to hold the majority of lysine oxidase activity at approximately 1 ng equivalent of lysine oxidase activity per 1 $\mu$l of media (activity units are standardized to the activity of known amounts of F22844 lysine oxidase). Lysine oxidase from the yeast culture media was subsequently purified and shown to have bioactivity against corn rootworm when combined with tedanalactam synthase. Surviving larvae exhibit 51% stunting with the combination sample of recombinant lysine oxidase purified from yeast and the F22844 culture filtrate purified tedanalactam synthase (Table 11). No significant stunting was seen with either protein individually. The yeast purified lysine oxidase had a specific activity of 25 U/mg protein versus a specific activity of 37 U/mg protein when the enzyme is purified from F22844.

TABLE 11

| Treatment (16 wells/sample) | Concentration (ppm) | # of survivors | Mean larval wt. (mg) (±SEM) |
|---|---|---|---|
| Acetate buffer | — | 61 | 0.94 ± 0.08 |
| Acetate buffer | — | 45 | 0.84 ± 0.07 |
| Lysine oxidase | 14 | 38 | 0.76 ± 0.06 |
| $M_r$ 50,000 | 10 | 43 | 0.80 ± 0.07 |
| Lysine oxidase + $M_r$ 50,000 | 14 + 10 | 36 | 0.44 ± 0.05 |

An NcoI-HindIII fragment containing the full length tedanalactam synthase cDNA gene (SEQ ID NO:40) from pMON25424 was interested into pMON6235, an *E. coli* expression vector containing an arabinose inducible promoter and G10 leader sequence to produce pMON25428 (FIG. 12). Weatern blot analysis showed that the *E. coli* expressed protein was cross reactive to polyclonal antibodies raised against the F22844 purified tedanalactam synthase. The relative migration of the expressed protein on SDS-PAGE was identical to the F22844 purified tedanalactam synthase. The recombinant tedanalactam synthase was purified in a 5 step procedure from *E. coli* expressing the tedanalactam synthase gene. Lysine oxidase was purified from a commercial preparation of *T. viride* lysine oxidase. Both the lysine oxidase and tedanalactam synthase were >95% pure by SDS-PAGE. In bioassays against SCRW neonate larvae, >80% stunting of survivors was seen with the combination sample of *T. viride* lysine oxidase and the *E. coli* produced F22844 tedanalactam synthase (Table 12). The number of survivors was also dramatically reduced. No significant mortality or stunting was seen with either protein individually. This demonstrates that the heterologously expressed or recombinant tedanalactam synthase is insecticidally active against corn rootworm when assayed in the presence of lysine oxidase.

TABLE 12

| Treatment (16 wells/sample) | Concentration (ppm) | # of survivors | Mean larval wt. (mg) (+SEM) |
|---|---|---|---|
| Tris/acetate buffer | — | 51 | 0.68 ± 0.04 |
| Tris/acetate buffer | — | 52 | 0.57 ± 0.04 |
| Lysine oxidase | 10 | 46 | 0.48 ± 0.04 |
| $M_r$ 50,000 | 18 | 80 | 0.52 ± 0.03 |
| Lysine oxidase + $M_r$ 50,000 | 10 + 18 | 23 | 0.11 ± 0.01 |

Lysine oxidase isolated from yeast transformed with pMON25030 and tedanalactam synthase isolated from *E. coli* transformed with pMON25428 were tested in bioassays for activity against western corn rootworm (Diabrotica) when combined respectively with tedanalactam synthase or lysine oxidase from F22844. Concentration response curves were run to determine the efficacy of these purified proteins on neonate WCRW larvae (Table 13). Excellent bioactivity was observed with $LC_{50}$'s below 2 ppm for each protein.

TABLE 13

| Sample | Conc. (ppm) | % Mortality | % Stunting |
|---|---|---|---|
| F50/FLO[1] | 20 + 20 | 100 | — |
| | 10 + 10 | 100 | — |
| | 2 + 2 | 63 | 80 |
| F50/YLO[2] | 20 + 20 | 100 | — |
| | 10 + 10 | 100 | — |
| | 2 + 2 | 90 | 87 |
| E50/FLO[3] | 10 + 10 | 84 | 80 |

[1]F22844 tedanalactam synthase and F22844 lysine oxidase
[2]F22844 tedanalactam synthase and yeast lysine oxidase (recombinant)
[3]*E. coli* tedanalactam synthase (recombinant) and F22844 lysine oxidase

Example 7

This example illustrates the production of antibodies useful for detection and quantitation of lysine oxidase and tedanalactam synthase.

To detect and quantitate tedanalactam synthase, polyclonal antibody #208 was developed by immunizing a rabbit with partially purified 50K protein derived from the *E. coli* expression vector pMON25428. A quantitative Enzyme Linked Immunoassay (ELISA) where polyclonal antibody #208 is both the coating and a Horse Radish Peroxidase (HRP) conjugated antibody was devised. The linear range of the tedanalactam synthase ELISA is between approximately 2.5 to 40 ng . Antibody #208 is also used for 50K Western blot analysis using the Enhanced Chemi-Luminescence (ECL) method of Amersham (cat #RPN 2106). The Western blot procedure utilizes antibody #208 as the primary antibody and an Amersham goat anti-rabbit HRP conjugated secondary antibody (cat #NA 934). Incubation in the ECL reagents allows visualization of the antigens by autoradiography.

To detect and quantitate lysine oxidase, polyclonal antibody #450 was developed by immunizing a rabbit with partially purified lysine oxidase protein derived from the *S. cerevisiae* expression vector pMON25030. A quantitative Enzyme Linked Immunoassay (ELISA) for lysine oxidase where polyclonal antibody #450 is both the coating and HRP-conjugated antibody was devised. The linear range of the lysine oxidase ELISA is between approximately 0.25 to 4.0 ng.

For analysis of the lysine oxidase by Western blot analysis, polyclonal antibody #2262 sera #3 was developed by immunizing a rabbit with a KLH conjugated 25-mer peptide CSVGEKLQQAFGYYKEKLAEDFDKG where all but the N-terminal cysteine residue is derived from the lysine oxidase peptide sequence. This antibody will detect both the lysine oxidase proenzyme of approximate $M_r$ 69,000 as well as the enzymatically active and mature form of approximate $M_r$ 69,000. Antibody #2262 sera #3 is used for LO Western blot analysis using the Enhanced Chemi-Luminescence (ECL) method of Amersham (cat #RPN 2106). The Western blot procedure utilizes antibody #2262 sera #3 as the primary antibody and an Amersham goat anti-rabbit HRP conjugate as the secondary antibody (cat #NA 934). Incubation in the ECL reagents allows visualization of the antigens by autoradiography.

Example 8

This example illustrates control of insects by expression of lysine and $M_r$ 50,000 proteins in plant colonizing bacteria.

To control insects, it may be desirable to express lysine oxidase and tedanalactam synthase in plant colonizing bacteria, and then apply this bacteria to the plant. As the insect feeds on the plant, it ingests a toxic dose of lysine oxidase and tedanalactam synthase produced by the plant colonizers. Plant colonizers can be either those that inhabit the plant surface, such as Pseudomonas or Agrobacterium species, or endophytes that inhabit the plant vasculature such as Clavibacter species. For surface colonizers, the lysine oxidase and tedanalactam synthase genes may be inserted into a broad host range vector capable of replicating in these Gram-negative hosts. Examples of these such vectors are pKT231 of the IncQ incompatibility group (Bagdasarian et al., 1981) or pVK100 of the IncP group (Knauf and Nester, 1982). For endophytes the tedanalactam synthase and lysine oxidase genes can be inserted into the chromosome by homologous recombination or by incorporation of the gene onto an appropriate transposon capable of chromosomal insertion in these endophytic bacteria.

Example 9

This example illustrates control of coleopteran insects by expression of lysine oxidase and tedanalactam synthase in transgenic monocotlyedenous plants.

To place the lysine oxidase gene in a vector suitable for expression in monocotyledonous plants (i.e. under control of the enhanced Cauliflower Mosaic Virus 35S promoter and linker to the hsp70 intron followed by a nopaline synthase polyadenylation site as in Brown and Santino, U.S. Pat. No. 5,424,412; 1995), the vector pMON19469 (FIG. 13) was digested with NcoI and EcoRI. The larger vector band of approximately 4.6 kb was electrophoresed, purified, and ligated with T4 DNA ligase to the NcoI-EcoRI fragment of approximately 1.9 kb containing the lysine oxidase gene (SEQ ID NO:45). The ligation mix was transformed into *E. coli* strain XL-1 Blue (Stratagene, La Jolla, Calif.). Carbenicillin resistant colonies were recovered and plasmid DNA recovered by DNA miniprep procedures. This DNA was subjected to restriction endonuclease analysis with enzymes such as NcoI and EcoRI (together), NotI, and PstI to identify plasmid pMON25040, which contains the lysine oxidase coding sequence fused to the hsp70 intron under control of the enhanced CaMV35S promoter (FIG. 14). Expression of functional lysine oxidase by pMON25040 in corn protoplasts was confirmed by electroporation of pMON25040 DNA into protoplasts followed by enzymatic assays of the plant protoplasts for lysine oxidase activity.

To place the lysine oxidase gene in a vector suitable for recovery of stably transformed and insect resistant plants, the 3.6 kb NotI restriction fragment from pMON25040 containing the lysine oxidase coding sequence fused to the hsp70 intron under control of the enhanced CaMV35S promoter was isolated by gel electrophoresis and purification. This fragment was ligated into NotI digested, alkaline phosphatase treated pMON15786, a plant transient expression vector containing the neomycin phosphotransferase coding sequence fused to the hsp70 intron under control of the enhanced CaMV35S promoter (FIG. 15). Kanamycin resistant colonies were obtained by transformation of this ligation mix into *E. coli* XL-1 Blue (Stratagene, La Jolla, Calif.) and colonies containing pMON25041 (FIG. 16) identified by restriction endonuclease digestion of plasmid miniprep DNAs. Restriction enzymes such as NotI, EcoRV, HindIII, NcoI, EcoRI, and BglII can be used to identify the appropriate clones containing the NotI fragment of pMON25040 in the NotI site of pMON15786 (i.e. pMON25041) in the orientation such that both genes are in tandem (i.e. the 3' end of the lysine oxidase expression cassette is linked to the 5' end of the nptII expression cassette). This vector can be introduced into the genomic DNA of corn embryos by particle gun bombardment followed by paromomycin selection to obtain corn plants expressing the lysine oxidase gene essentially as described in Brown and Santino U.S. Pat. No. 5,424,412. These plants can then be "crossed" by pollen transfer to plants containing the tedanalactam synthase gene (construction described below, from pMON30411) to obtain plants that are resistant to insect infestation, particularly corn rootworm (Diabrotica spp.). Alternatively, pMON30411 and 25040 could be co-bombarded to obtain plants that are resistant to insect infestation, particularly corn rootworm (Diabrotica spp.).

To place the tedanalactam synthase gene in a vector suitable for expression in monocotyledonous plants (i.e. under control of the enhanced Cauliflower Mosaic Virus 35S promoter and linked to the hsp70 intron followed by a nopaline synthase polyadenylation site), the vector pMON19469 was digested with NcoI and EcoRI. The larger vector band of approximately 4.6 kb was electrophoresed, purified, and ligated with T4 DNA ligase to the NcoI-EcoRI fragment of approximately 1.4 kb containing the tedanalactam synthase gene (SEQ ID NO: 40) obtained from the *E. coli* expression vector pMON25428. The ligation mix was transformed into *E. coli* strain XL-1 Blue (Stratagene, La Jolla, Calif.), carbenicillin resistant colonies recovered and plasmid DNA recovered by DNA miniprep procedures. This DNA was subjected to restriction endonuclease analysis with NcoI and EcoRI, NotI, and SacI to identify clones containing pMON30410, containing the tedanalactam synthase coding sequence fused to the hsp70 intron under control of the enhanced CaMV35S promoter (FIG. 18). Expression of the tedanalactam synthase gene by pMON30410 in corn protoplasts was confirmed by electroporation of pMON30410 DNA into protoplasts followed by Western blot analysis of the plant protoplast extracts for tedanalactam synthase cross reacting species of the same $M_r$ as native tedanalactam synthase.

Figure 17:
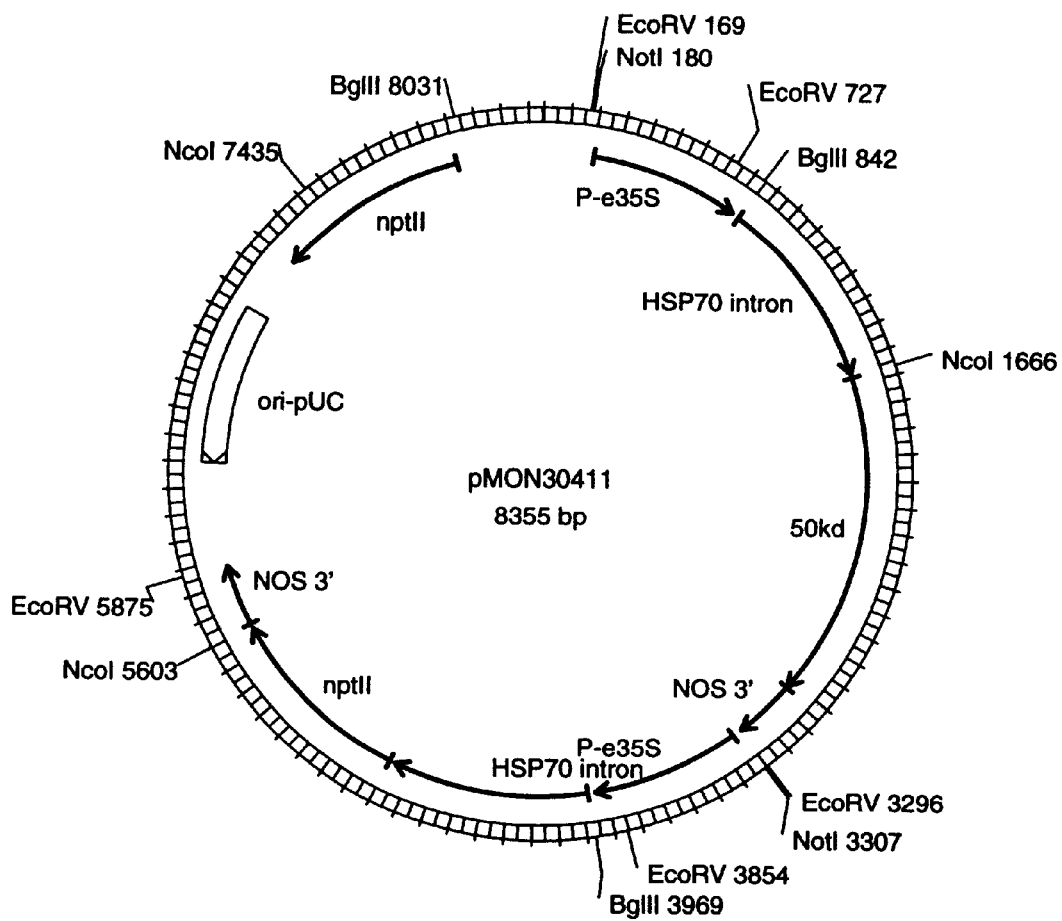
FIG. 17 represents a plasmid map of pMON30411 which is a plant transformation vector containing a tedanalactam synthase variant gene under the control of a cauliflower mosaic virus 35S promoter.
Figure 18:
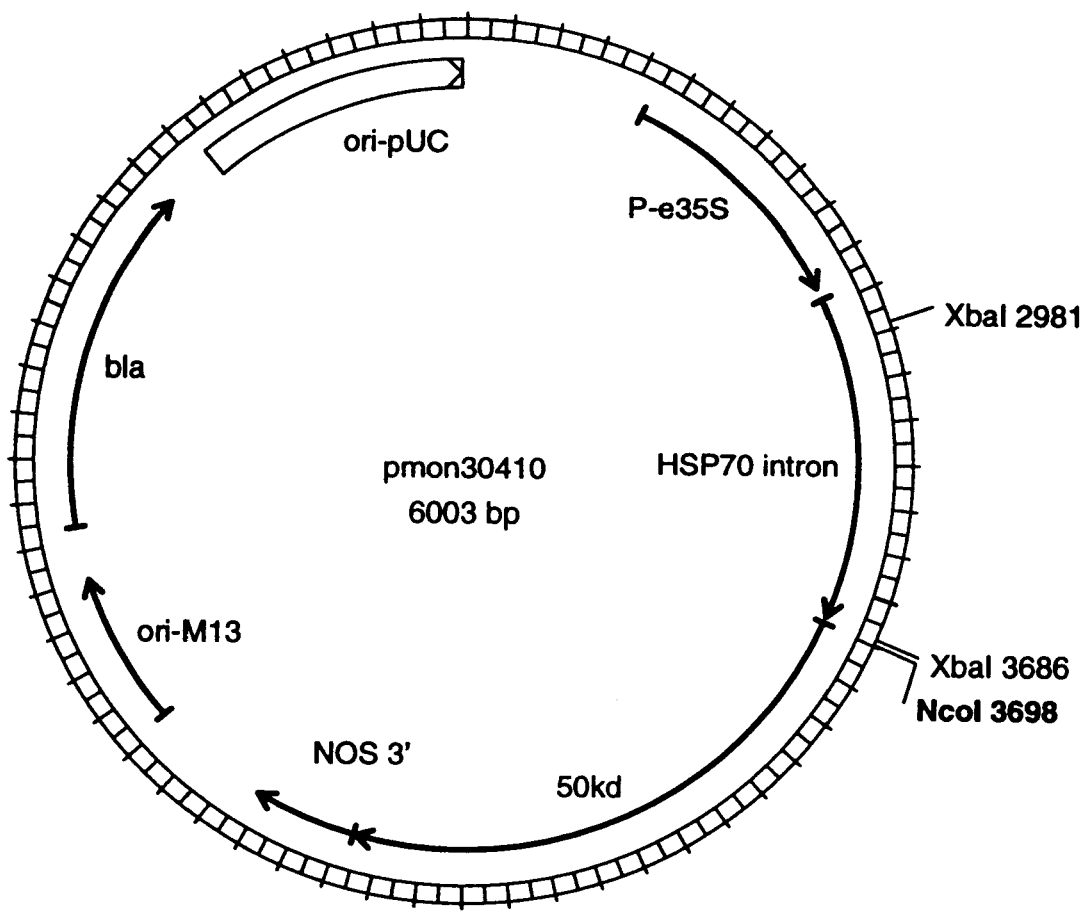
FIG. 18 represents a plasmid map of pMON30410 which is a plant transformation vector containing a tedanalactam synthase gene under the control of a cauliflower mosaic virus 35S promoter.

To place the tedanalactam synthase gene in a vector suitable for recovery of stably transformed and insect resistant monocot plants, the 3.1 kb NotI restriction fragment from pMON30410 containing the tedanalactam synthase coding sequence fused to the hsp70 intron under control of the enhanced CaMV35S promoter was isolated by gel electrophoresis and purification. This fragment was ligated with pMON15786 treated with NotI and calf intestinal alkaline phosphatase (pMON15786 contains the neomycin phosphotransferase coding sequence fused to the hsp70 intron under control of the enhanced CaMV35S promoter). Kanamycin resistant colonies were obtained by transformation of this ligation mix into *E. coli* XL-1 Blue (Stratagene, La Jolla, Calif.) and colonies containing pMON30411 (FIG. 17) identified by restriction endonuclease digestion of plasmid miniprep DNAs. Restriction enzymes such as NotI, EcoRV, HindIII, NcoI, EcoRI, and BglII may be used to identify the appropriate clones containing the NotI fragment of pMON30411 in the NotI site of pMON15786 (i.e. pMON30411) in the orientation such that both genes are in tandem (i.e. the 3' end of the tedanalactam synthase expression cassette is linked to the 5' end of the nptII expression cassette). This vector can be introduced into the genomic DNA of corn embryos by particle gun bombardment followed by paromomycin selection to obtain corn plants expressing the tedanalactam synthase gene. These plants can then be "crossed" by pollen transfer to plants containing the lysine oxidase gene (pMON25041; see description below) to obtain plants that are resistant to insect infestation, particularly corn rootworm (Diabrotica spp.). Alternatively, pMON30411 and 25040 could be co-bombarded to obtain corn plants that are resistant to insect infestation, particularly corn rootworm (Diabrotica spp.).

To place both the tedanalactam synthase and lysine oxidase genes in a vector suitable for recovery of stably transformed and insect resistant plants, the 3.6 kb NotI restriction fragment from pMON25040 containing the lysine oxidase coding sequence fused to the hsp70 intron under control of the enhanced CaMV35S promoter was isolated by gel electrophoresis and purification. This fragment was ligated with pMON30411 that was partially digested with NotI to obtain pMON30411 plasmid DNA cut only once with NotI and treated with calf intestinal alkaline phosphatase (pMON30411 contains the neomycin phosphotransferase coding sequence fused to the hsp70 intron under control of the enhanced CaMV35S promoter and the tedanalactam synthase coding sequence fused to the hsp70 intron under control of the enhanced CaMV35S promoter). Partial digestion and isolation of pMON30411 plasmid with only one NotI site cut was accomplished by digesting 5 µg of DNA in 1×HSB buffer (Boehringer-Mannheim, Indianapolis, Ind.), 10 µg/mL bovine serum albumin, 10 µg/mL ethidium bromide and 0.4 units of NotI restriction endonuclease followed by gel electrophoresis and purification of the linearized plasmid DNA. Kanamycin resistant colonies were obtained by transformation of this ligation mix into *E. coli* XL-1 Blue (Stratagene, La Jolla, Calif.).

Figure 19:
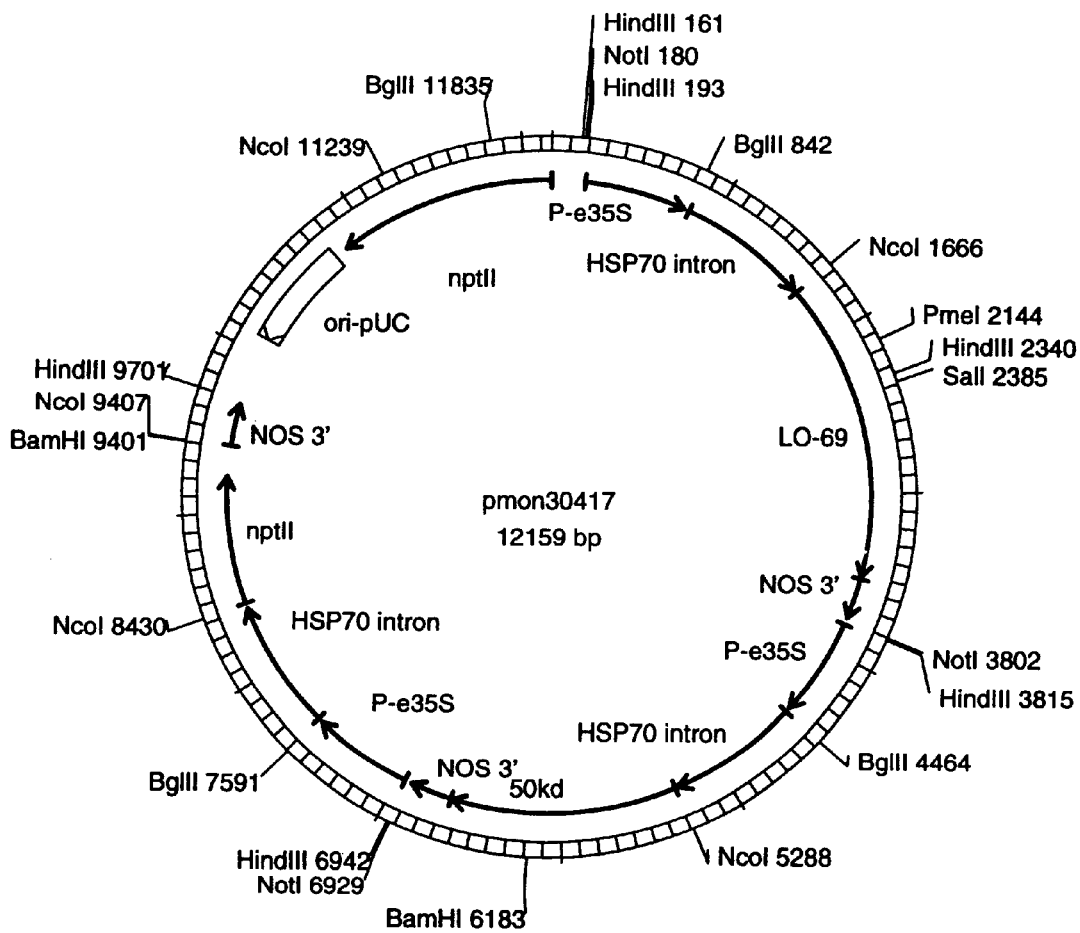
FIG. 19 represents a plasmid map of pMON30417 which is a plant transformation vector containing a neomycin phosphotransferase selectable marker, a tedanalactam synthase gene, and a lysine oxidase gene each under the control of a separate cauliflower mosaic virus 35S promoter.

Colonies containing pMON30417 (FIG. 19) were identified by restriction endonuclease digestion of plasmid miniprep DNAs. Restriction enzymes such as NotI, SacI, HindIII BamHI, NcoI/EcoRI, EcoRV and BglII may be used to identify the appropriate clones containing the NotI fragment of pMON25040 in the NotI site of pMON30411 upstream of the tedanalactam synthase gene (i.e. pMON30417) in the orientation such that all genes are in tandem (i.e. the 3' end of the lysine oxidase cassette is linked to the 5' end of the tedanalactam synthase expression cassette and the 3' end of the $M_r$ 50,000 expression cassette is linked to the 5' end of the nptII expression cassette). Expression of both the lysine oxidase and tedanalactam synthase in genes in corn leaf protoplasts electroporated with pMON30417 was observed. This vector can be introduced into the genomic DNA of corn embryos by particle gun bombardment followed by paromomycin selection to obtain corn plants expressing both the lysine oxidase and tedanalactam synthase genes essentially as described in Brown and Santino U.S. Pat. No. 5,424,412. Transgenic corn plants expressing the lysine oxidase and tedanalactam synthase genes can be identified by an ELISA assay specific for the two proteins or via an enzymatic assay for lysine oxidase activity. These plants may be resistant to insect infestation, particularly corn rootworm (Diabrotica spp.).

Both the lysine oxidase gene in pMON25040 and the tedanalactam synthase gene in pMON30410 were shown to express the respective F22844 genes in corn leaf protoplasts. Corn leaf protoplasts were electroporated with pMONs 25040 and 30410 as well as a pMON19649 control and incubated for about 24 hours. Total protein was extracted and assayed for the presence of enzymatic lysine oxidase activity (Table 14) or tedanalactam synthase cross reacting material by Western blot analysis. Both genes are expressed in corn cells.

TABLE 14

| | ng LO activity/mg total protein[1] | |
|---|---|---|
| Vector | cell pellet[2] | culture media (conc)[3] |
| pMON25040 | 148 ± 12 | 411 ± 3 |
| pMON19649 | 0 | 0 |

[1]Lysine oxidase activity equivalents in nanograms per mg of total extracted protein. Lysine activity equivalents were determined by assaying in parallel a dilution series of known amounts of purified F22844 lysine oxidase.
[2]cell pellet was extracted with glass beads and desalted prior to assay.
[3]culture media was concentrated over a Centricon 10 column (Amicon).

Corn plants transformed with the monocot transformation vector containing both the lysine oxidase and tedanalactam synthase expression cassettes (i.e. pMON30417) were obtained as described above. A transgenic event that expressed both lysine oxidase and tedanalactam synthase was identified and outcrossed to yield progeny that express both the lysine oxidase and tedanalactam synthase proteins at approximately 2.5 and 4.5 PPM, respectively (leaf expression levels as determined by an ELISA). Progeny plants of the pMON30417 event and genotypically identical controls that do not express the lysine oxidase or tedanalactam synthase proteins were infested with western corn rootworm eggs and scored for root damage by the Iowa Rating system (Hills and Peters, 1971) after 3 weeks of feeding. These results are summarized in Table 15.

TABLE 15 pMON30417 mediated control of western corn rootworm in transgenic corn

| Treatment | N[1] | Mean RDR[2] (SE)[3] | Range[4] |
|---|---|---|---|
| pMON30417 | 10 | 3.0 (0) | 3 |
| Control | 5 | 4.6 (0.24) | 4–5 |

[1]N is number of plants assayed.
[2]RDR is the Root Damage Rating; 1–5 scale, 5 most severe.
[3]X2 = 19.095, P < 0.002
[4]Range of values obtained.

In addition to the quantitative Root Damage Rating data demonstrating protection of corn plant roots expressing the lysine oxidase and tedanalactam synthase proteins (pMON30417), a number of qualitative observations also indicate that these genes confer corn rootworm control. First, the above ground nodal roots were intact in the pMON30417 plants but were destroyed in the control plants. Second, the control plants had copious numbers of larvae within the stalk at the time of examination while the pMON30417 plants had none.

A bare root assay was performed on segregating 'Laffite' plants to measure plant insecticidal activity and larval growth. Survival on the control was 39% as compared to 4% on F22844. Those surviving on F22844 were in very poor condition (Table 16). Because of the poor condition of the F22844 larvae, no larval weights were recovered.

TABLE 16

Percent survival and mean larval weight of WCR in a bare root assay.

| Treatment | N | Survival (%) | Larval weight (mg) |
|---|---|---|---|
| Control | 15 | 38.7 | 0.24 |
| F22844 | 9 | 4.4 | — |

The western corn rootworm whole plant bioassay was repeated with 'Laffite' in ten inch pots. The larger pot would allow for near normal plant development, thus allowing for both the opportunity to study insect control and the phytotoxic effects. Positive plants (2–4 ppm) were approximately 30–40 percent stunted at the end of the assay period for the H99 and B73 pedigrees, respectively. The root system on the positive plants appeared normal for that size of a plant. The insect control on the positive plants appeared normal for that size of a plant.

The average root damage ratings of the F22844 plants were significantly lower than the negative plants, 2.6 and 2.7 versus 5.2 and 5.9 for the H99 and B73 pedigrees, respectively. The negative segregants showed severe rootworm damage with 2–3 entire nodes of the roots pruned (Table 17). Note that constitutive expression of enzymatically active LO can result in plant height reductions (Table 17). Combinations of root specific promoters, LO69 proenzyme variants resistant to plant protease activation, and/or organellar or extracellular targeting of LO69 or LO69 proenzyme variants are anticipated to relieve this effect of LO expression in plants.

TABLE 17

Mean root ratings (RDR) for F22844, Event 'Laffite', for both a B73 and H99 S1 cross from the R0 in a ten inch pot WCR bioassay

| Treatment | Pedigree | N | RDR Mean | RDR Range | Plant Height Mean (inch) |
|---|---|---|---|---|---|
| F22844 | H99 | 16 | 2.6 | 1–3 | 28.0 |
|  | B73 | 10 | 2.7 | 1–3 | 30.6 |
| Control | H99 | 10 | 5.2 | 3–5 | 39.3 |
|  | B73 | 8 | 5.9 | 5–6 | 49.6 |

Figure 20:
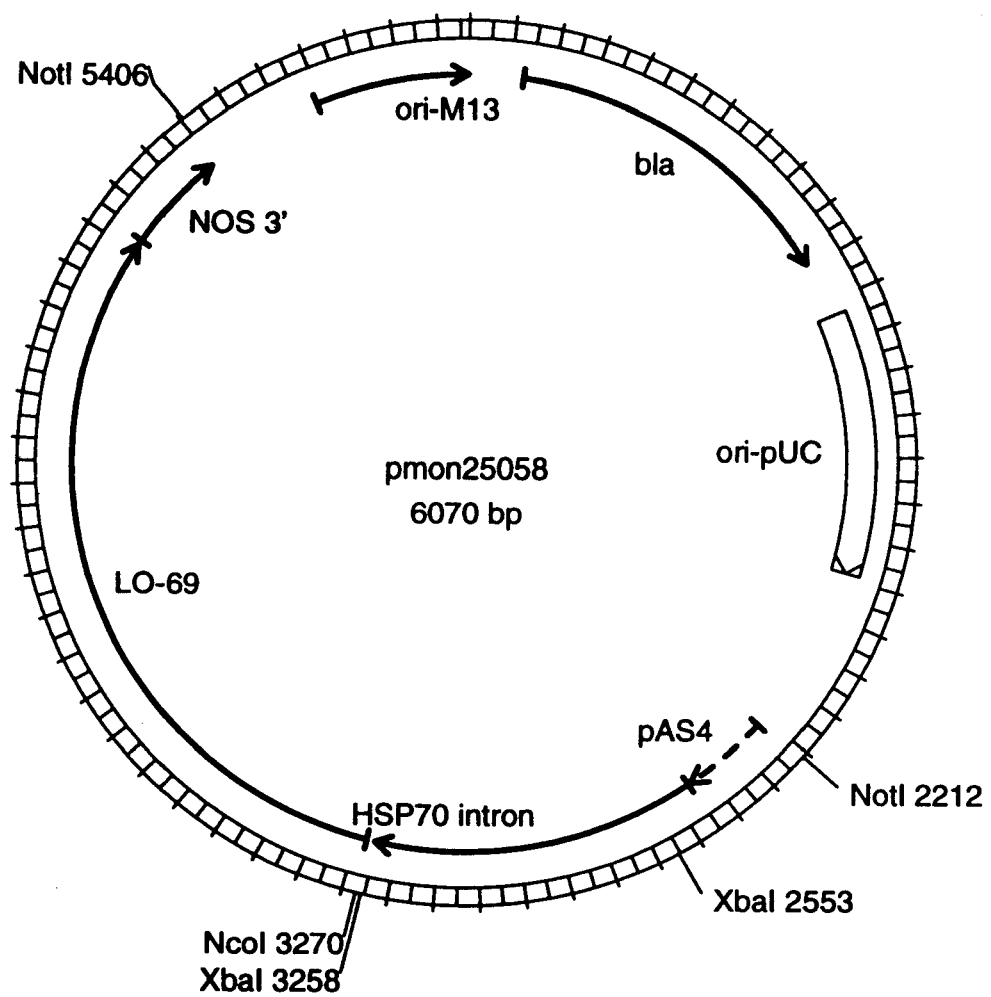
FIG. 20 represents a plasmid map of pMON25058 which is a plant transient is expression vector containing a lysine oxidase gene fused to an hsp70 intron under the control of a root tissue enhanced promoter.
Figure 21:
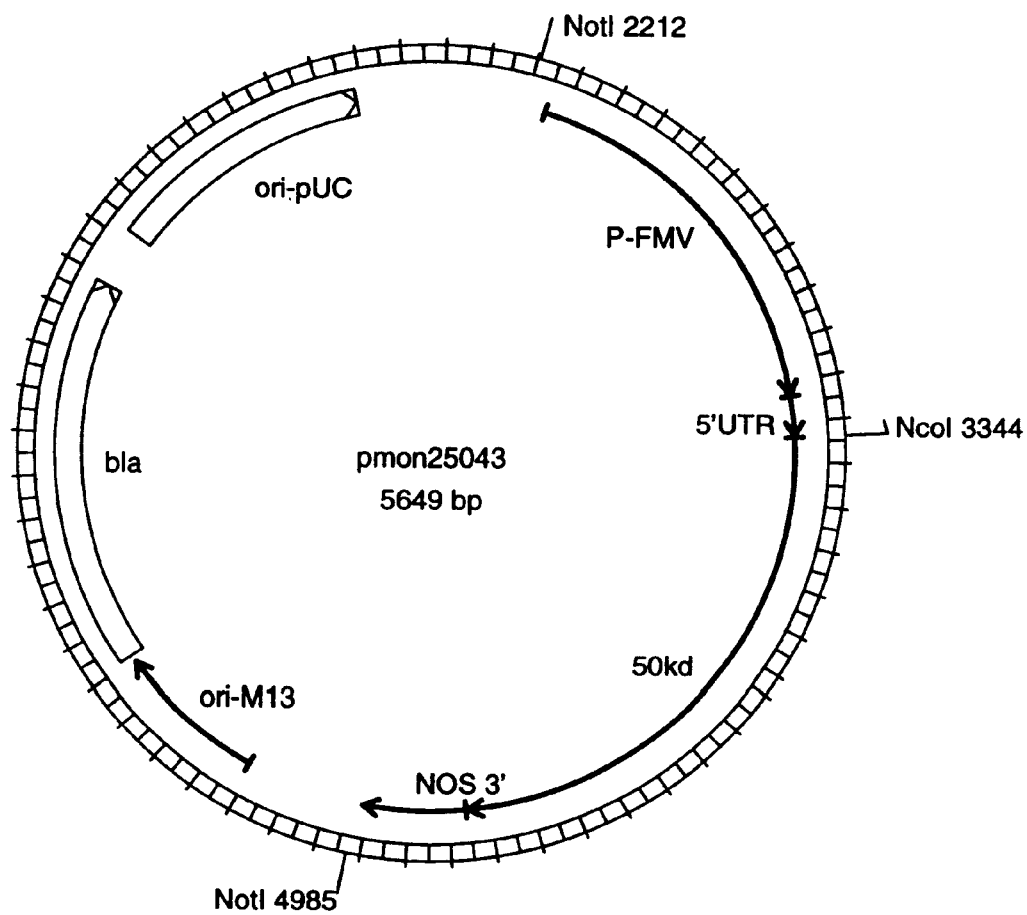
FIG. 21 represents a plasmid map of pMON25043 which is a plant transient expression vector containing a tedanalactam synthase gene fused to an hsp70 leader under the control of a figwort mosaic virus promoter.
Figure 22:
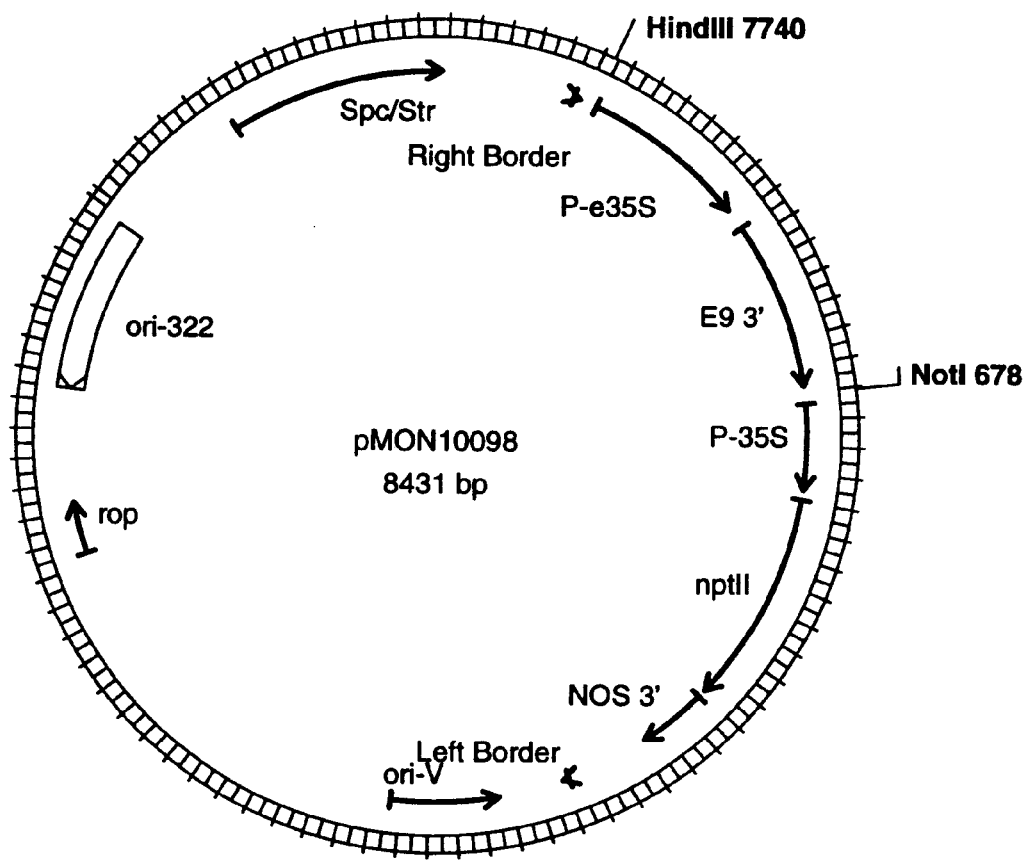
FIG. 22 represents a plasmid map of pMON10098 which is an Agrobacterium mediated double border plant transformation vector containing a neomycin phosphotransferase selectable marker under the control of a cauliflower mosaic virus 35S promoter.
Figure 23:
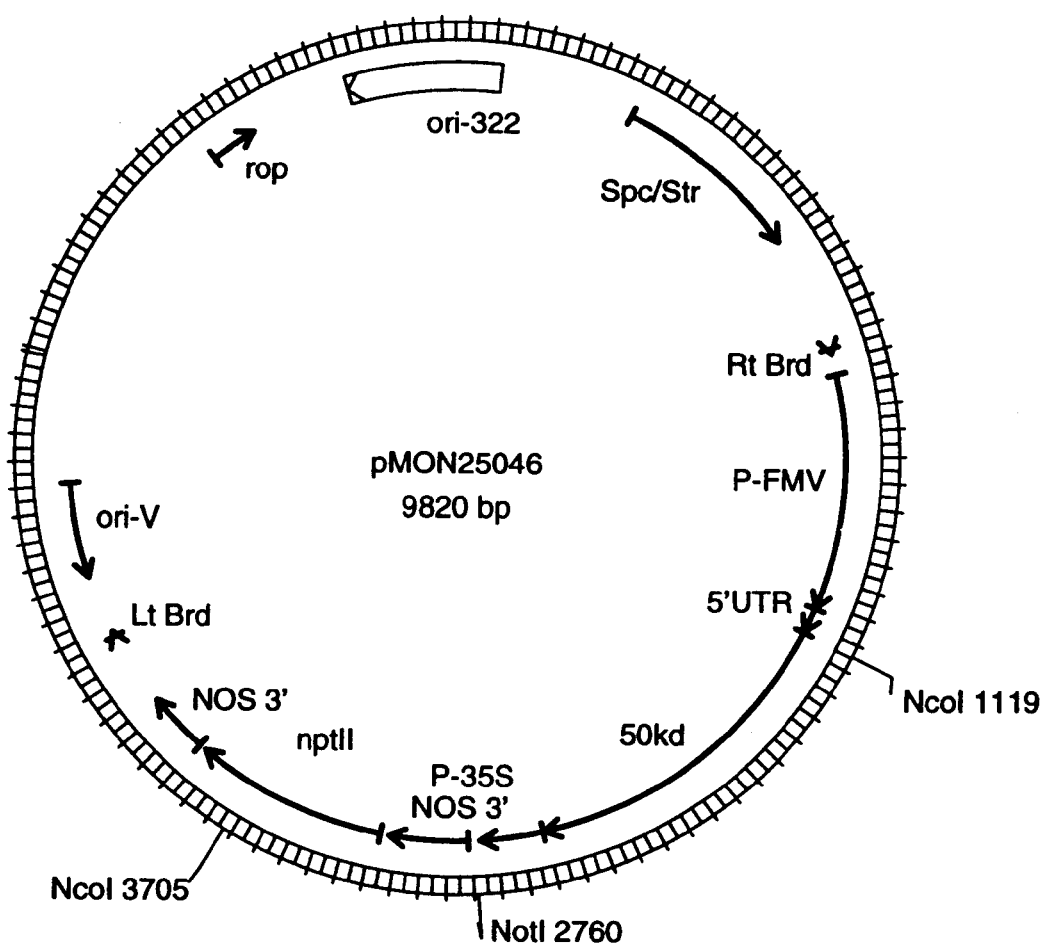
FIG. 23 represents a plasmid map of pMON25046 which is an Agrobacterium mediated double border plant transformation vector containing a neomycin phosphotransferase selectable marker under the control of a cauliflower mosaic virus 35S promoter, and a tedanalactam synthase gene fused to an hsp70 leader under the control of a figwort mosaic virus promoter.
Figure 24:
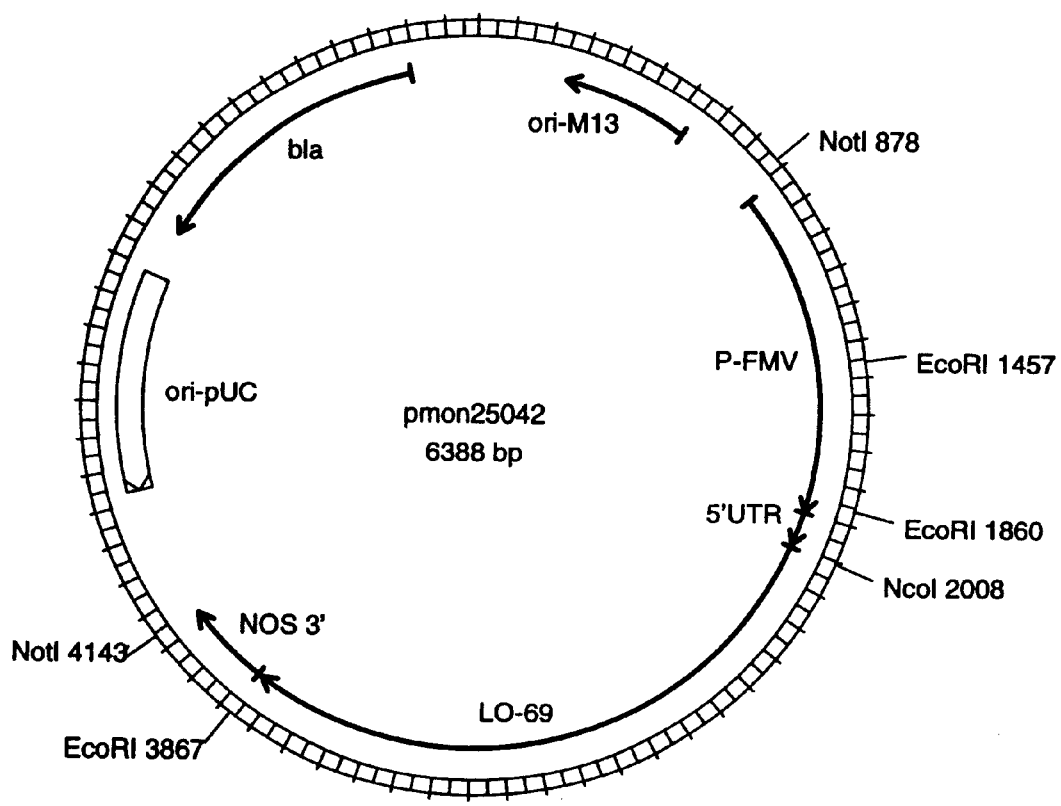
FIG. 24 represents a plasmid map of pMON25042 which contains a lysine oxidase gene fused to a petunia hsp70 leader sequence under the control of a figwort mosaic virus promoter.
Figure 25:
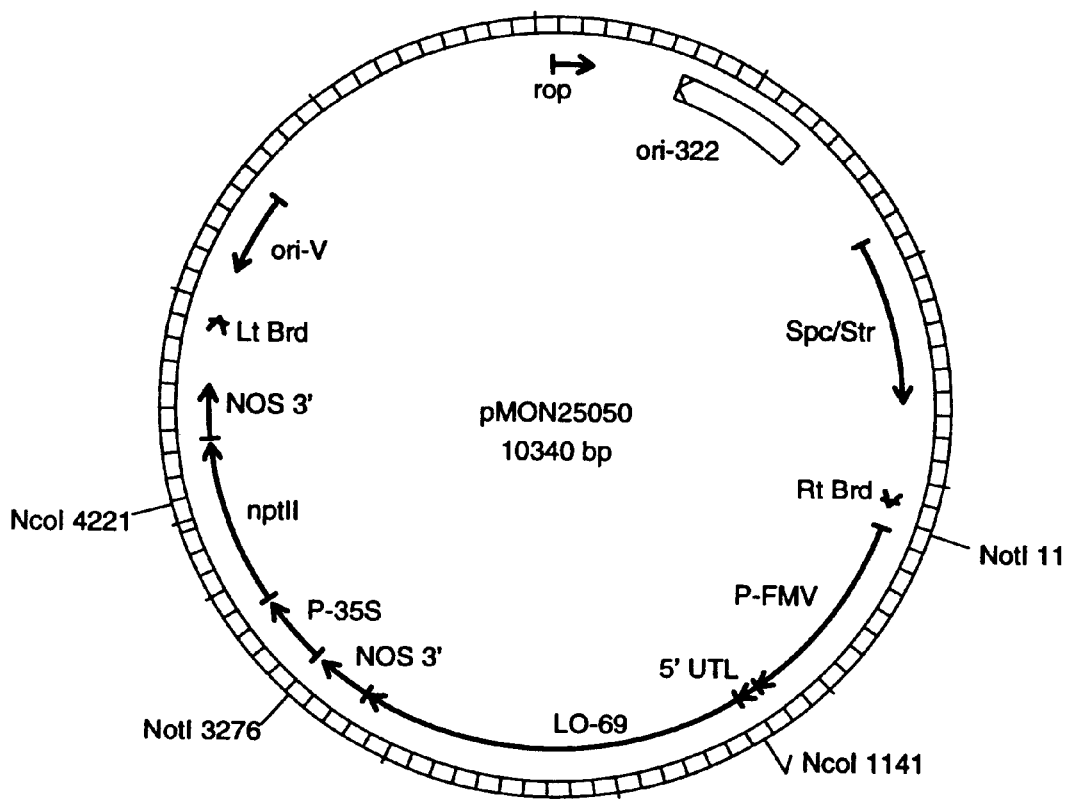
FIG. 25 represents a plasmid map of pMON25050 which is an Agrobacterium mediated double border plant transformation vector containing a neomycin phosphotransferase selectable marker under the control of a cauliflower mosaic virus 35S promoter, and a lysine oxidase gene fused to a petunia hsp70 leader sequence under the control of a figwort mosaic virus promoter.

To reduce plant height reductions caused by lysine oxidase expression and to target expression of the insecticidal proteins to the roots attacked by Diabrotica sp, promoters that limit expression of lysine oxidase to roots are valuable. In this example, the 4 as-1 root enhanced promoter (Lam et al., U.S. Pat. No. 5,023,179; designated pAS4 in plasmid maps) was fused to a transcription unit containing the maize hsp70 intron, the lysine oxidase gene, and the nos polyadenylation site in pMON25058 (FIG. 20). The 4 as-1 promoter was also fused to a transcription unit containing the maize hsp70 intron, the tedanalactam synthase gene, and the nos polyadenylation site in pMON25060. Both the lysine oxidase and tedanalactam synthase transcription units were subsequently combined in a vector containing a neomycin phosphotransferase coding sequence fused to the hsp70 intron under control of the enhanced CaMV35S promoter to yield pMON25061 (FIG. 21). Transgenic corn plants expressing both lysine oxidase and tedanalactam synthase genes were recovered as previously described.

One illustrative pMON25061 event, R44482, was further analyzed and shown to express lysine oxidase and tedanalactam synthase at relatively high levels in root tissue and at relatively low levels in leaf tissue (2.9 ppm lysine oxidase in root versus 0.9 ppm in leaf; 8.4 ppm tedanalactam synthase in root versus 1.9 ppm in leaf). Event 44482 was also displayed significant levels of CRW resistance in both growth chamber and field tests (Table 18). Although plant height reductions associated with the pMON25061 transgene in R44482 were not eliminated, the level of stunting is clearly less than that observed when Lysine oxidase is expressed from a constitutive CaMV e35S promoter (Tables 17 and 18).

TABLE 18

Corn Rootworm Damage Rating and Height of CRW infested and non-infested pMON25061 plants and wild type controls

| Plants | CRW RDR[1] (Height) [Growth Chamber] | CRW RDR[1] (Height) [Field Test Site #1] | CRW RDR[1] (Height) [Field Test Site #2] |
|---|---|---|---|
| 25061#44482 (infested) | 3.2 RDR (51.5 in) | 5.8 RDR (47 in) | 5.6 RDR (37 in) |
| wild type (infested) | 10.4 RDR (50.6 in) | 9.4 RDR (60 in) | 11.9 RDR (51 in) |
| 25061#44482 (uninfested) | ND | ND (79 in) | ND (84 in) |
| wild type (uninfested) | ND | ND (84 in) | ND (86 in) |

[1]RDR is the Root Damage Rating; 1–15 scale, 15 most severe.

Example 10

This example illustrates construction of lysine oxidase and tedanalactam synthase dicot plant expression vectors, production of dicot plants expressing these genes, and use of these plants to control insect pests.

To control coleopteran insect pests such as the Colorado potato beetle, *Leptinotarsa decemlineata* (Say), in dicotyledonous plants such as potato, *Solanum tuberosum,* or to control boll weevil, *Anthonomus grandis,* in cotton, *Gossypium hirsutum,* it would be useful to engineer the lysine oxidase and tedanalactam synthase genes for expression in dicotyledonous plants.

To express tedanalactam synthase in dicots, the HindIII/NcoI fragment containing a duplicated or enhanced version of the FMV promoter (Rogers, 1995) and petunia hsp70 5 prime untranslated leader (Winter et al., 1988) from pMON18411 was ligated into the NcoI/HindIII sites of pMON30410 located 5 prime to the tedanalactam synthase coding region (SEQ ID NO: 40) to yield pMON25043, containing a tedanalactam synthase variant under the control of an enhanced FMV promoter/petunia hsp70 untranslated leader with a NOS polyadenylation signal (FIG. 21). The composite eFMV/hsp70/tedanalactam synthase/nos gene cassette was isolated as a HindIII/NotI fragment from pMON25043 and ligated into the HindIII and NotI sites in pMON10098, a double border plant transformation vector (FIG. 22), to form pMON25046 (FIG. 23). The pMON25046 plasmid is an Agrobacterium-based plant transformation vector that places the composite eFMV/hsp70/tedanalactam synthase/nos gene and enhanced CaMV35S/neomycin phosphotransferase/nos kanamycin selectable marker gene between the right and left T-DNA border fragments. This vector can be mobilized into Agrobacterium (Ditta et al., 1980) and used to obtain transgenic dicotyledonous plants as described (Horsch et al., 1985).

To express lysine oxidase in dicots, the NcoI/SmaI fragment of the lysine oxidase gene from pMON25040 (SEQ ID NO: 45) was ligated into the NcoI and SmaI sites located between the enhanced FMV promoter/petunia hsp70 5 prime untranslated leader (utl or UTR) and the NOS polyadenylation signal to yield pMON25042, containing a lysine oxidase variant under the control of the enhanced FMV promoter/petunia hsp70 leader with a NOS polyadenylation signal (FIG. 24). The composite eFMV/hsp70 utl/lysine oxidase/nos gene from pMON25042 was isolated from pMON25042 on a single NotI fragment and subsequently ligated into the NotI site of pMON25048, a derivative of pMON10098, containing a single NotI site and kanamycin selectable marker gene located between the right and left T-DNA border sequences, to obtain pMON25050 (FIG. 25). pMON25050 can be mobilized into Agrobacterium (Ditta et al., 1980) and used to obtain transgenic dicotyledonous plants as described previously (Horsch et al., 1985).

To place both the tedanalactam synthase and lysine oxidase genes in a vector suitable for recovery of stably transformed and insect resistant dicotyledonous plants, the NotI fragment containing the lysine oxidase expression cassette from pMON25042 was ligated into a single NotI site in pMON25046 introduced by single hit partial NotI digestion to obtain pMON25049 (FIG. 2). The pMON25049 plasmid is an Agrobacterium mediated transformation vector containing a kanamycin selectable marker gene, the tedanalactam synthase expression cassette, and the lysine oxidase expression cassette between the right and left T-DNA border sequences. This vector can be used to obtain dicotyledonous plants expressing both the tedanalactam synthase and lysine oxidase genes via the previously described Agrobacterium-mediated plant transformation techniques.

Arabidopsis plants were transformed with pMON25046 and pMON25050 via the Agrobacterium mediated meristem infiltration technique (Bechtold et al., 1993) and screened for expression of the tedanalactam synthase and lysine oxidase genes, respectively. Identification of tedanalactam synthase expressors was via an ELISA assay specific for the tedanalactam synthase protein. Lysine oxidase expressors were identified via direct enzymatic assays. Pollen was transferred from lysine oxidase expressing pMON25050 lines to tedanalactam synthase expressing pMON25046 lines to obtain F1 progeny that express both the tedanalactam synthase and lysine oxidase genes. These F1 progeny plants that expressed both the lysine oxidase and tedanalactam synthase genes and appropriate controls were exposed to southern corn rootworm larvae to determine if these genes would cause larval stunting (as assayed by reductions in larval weight post-feeding) and reduced feeding (as assayed by a Leaf Damage Rating). The results displayed in Table 19 demonstrate that these genes cause significant larval stunting and yield reduced leaf damage when expressed in transgenic Arabidopsis plants.

TABLE 19

Activity of F22844 expressing Arabidopsis on SCRW as shown by mean larval weight (mg) and Leaf Damage Rating (LDR). N is the number of larvae weighed.

| Treatment | N | Mean Larval wt. (mg) (±SEM) | Mean LDR |
|---|---|---|---|
| LO + $M_r$ 50,000 | 25 | 0.23 (±0.02) | 0.84 |
| untransformed | 49 | 0.44 (±0.02) | 2.79 |
| LO only | 25 | 0.47 (±0.03) | 2.11 |
| $M_r$ 50,000 only | 37 | 0.39 (±0.02) | 2.00 |

It may also be advantageous to localize the lysine oxidase or tedanalactam synthase to the plastids. Proteins can be directed to the chloroplast by including at their N-termini a chloroplast transit peptide (CTP). One CTP that has worked to localize heterologous proteins to the chloroplast of dicotyledonous plants is from the RUBISCO small subunit gene of Arabidopsis, denoted ats1A. A variant of this transit peptide that encodes the transit peptide, 23 amino acids of mature RUBISCO sequence, plus a reiteration of the transit peptide cleavage site has been constructed for the successful chloroplast localization of the B.t.k. protein (Fischhoff and Perlak, 1990). It is anticipated that this same fragment of the atsla gene, when fused in frame to the amino-terminal coding region of the lysine oxidase or tedanalactam synthase genes, will similarly result in chloroplast localization of these proteins in dicotyledonous plants. Note that this chloroplast targeted expression cassette is subsequently cloned into a binary Agrobacterium transformation vector, mobilized into disarmed Agrobacterium hosts and used to transform dicots.

To localize lysine oxidase in corn plastids, A fragment of the maize RUBISCO small subunit gene denoted mSSU CTP or zmS1 containing a duplicated cleavage site (Russell et al., 1993) was used to localize either the lysine oxidase or tedanalactam synthase in chloroplasts of corn plants. For example, an XbaI/NcoI fragment (SEQ ID NO:49) encoding the mSSU CTP derived from pMON22089 was ligated into the XbaI and NcoI sites of pMON30405 (lysine oxidase; SEQ ID NO:50) or pMON30410 ($M_r$ 50,000 protein) that are located between the hsp70 intron and coding regions of these genes to obtain in-frame fusions of the mSSU CTP to the N-termini of these proteins. The pMON30405 lysine oxidase sequence (SEQ ID NO:50) was obtained by PCR mutagenesis using pMON23684 (SEQ ID NO:15) as template with oligonucleotides N28 (SEQ ID NO:51) and N29 (SEQ ID NO:52) as primers. The mSSU CTP fusions to lysine oxidase or $M_r$ 50,000 protein under control of the enhanced CaMV35S promoter and the hsp70 intron are cloned as NotI fragments into pMON15786, a monocot transformation vector described above. Transgenic corn plants expressing lysine oxidase were obtained at a lower frequency when the plastid targeting signal was employed, indicating that plastid targeting is not a preferred method of expressing lysine oxidase in transgenic corn.

Example 11

This example illustrates mitochondrial targeting of the tedanalactam synthase or lysine oxidase proteins in transgenic plants.

It may also be advantageous to target the tedanalactam synthase or lysine oxidase proteins to the mitochondria. This may be accomplished by fusing a suitable mitochondrial targeting peptide (MTP) to the amino-terminus of either the tedanalactam synthase or lysine oxidase proteins. One example of an MTP that has been demonstrated to target heterologous proteins to mitochondria of dicots is from the beta subunit of the mitochondrial ATP synthase (Boutry et al., 1987). We infer that this same sequence will direct mitochondrial import of either the tedanalactam synthase or lysine oxidase proteins in transgenic dicot plants when fused in frame to the amino-termini of these proteins. Appropriate promoter and termination sequences, Agrobacterium vectors, and transformation procedures needed to obtain transgenic dicotyledonous plants expressing the MTP fusion genes were described previously.

It may similarly be desirable to target the tedanalactam synthase or lysine oxidase proteins to the mitochondria of monocotyledonous plants by making fusions of monocotyledonous plant derived MTPs to these proteins. One example of a sequence that may direct mitochondrial import in monocots is one that is substantially homologous to the maize mitochondrial ATP synthase beta subunit (Winning et al., 1990). Another example would be the MTP from the maize superoxide dismutase isozyme 3 (Sod3) (White and Scandalios, 1989).

Figure 26:
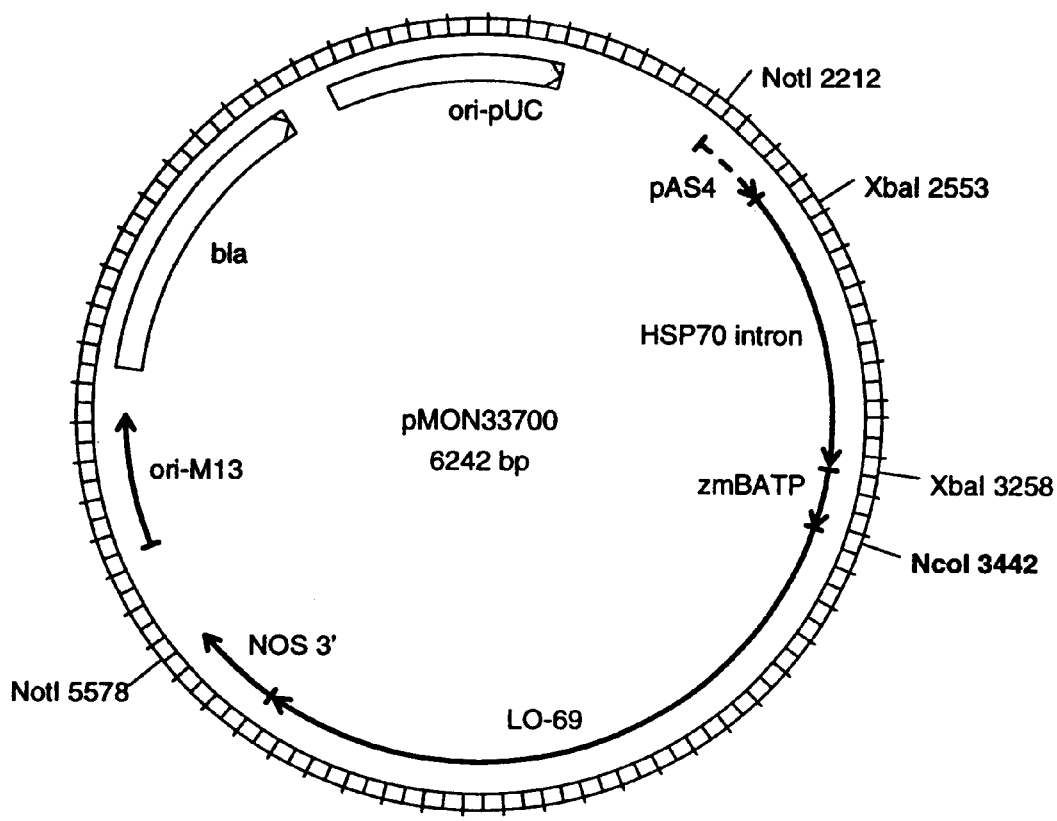
FIG. 26 represents a plasmid map of pMON33700 which is a plant transient expression vector containing a lysine oxidase gene fused to a sequence encoding a maize ATP synthase beta subunit mitochondrial transit peptide, which is fused to an hsp70 intron sequence under the control of a root tissue enhances promoter.
Figure 27:
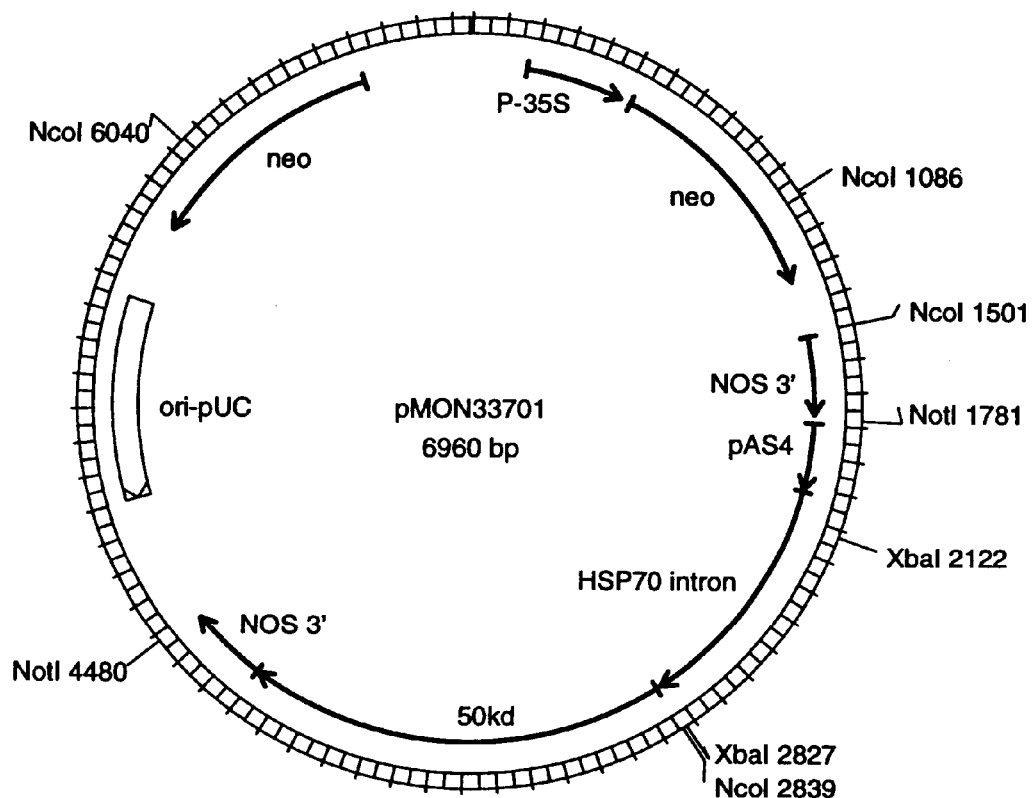
FIG. 27 represents a plasmid map of pMON33701 which is a plant transformation vector containing a neomycin phosphotransferase gene under the control of a cauliflower mosaic virus 35S promoter, and a tedanalactam synthase gene fused to an hsp70 intron sequence under the control of a root tissue enhanced promoter.

For example, the XbaI/NcoI fragment containing the portion of the maize ATP synthase beta subunit MTP sufficient to direct mitochondrial import (SEQ ID NO: 53) from pMON30447 was ligated into the XbaI and NcoI sites of pMON25058 (lysine oxidase) that are located between the hsp70 intron and lysine oxidase coding region to obtain in-frame fusions of the maize ATP synthase beta subunit MTP (zmBATP) to the N-termini of lysine oxidase, producing plasmid pMON33700 (FIG. 26). The pMON33700 NotI cassette containing the zmBATP-lysine oxidase expression cassette was engineered into pMON33701 (FIG. 27) to obtain pMON33702, a plant transformation vector containing the zmBATP-Lysine oxidase expression cassette as well as previously described neomycin phosphotransferase and tedanalactam synthase expression cassettes (FIG. 28).

Transgenic corn expressing both lysine oxidase and tedanalactam synthase in roots were obtained with pMON33702. Phenotypic analysis of these lines indicated that use of the zmBATP targeting signal did not alleviate stunting associated with high level lysine oxidase expression in leaves. However, root specific or enhanced expression of the mitochondrial targeted lysine oxidase expression may alleviate stunting. It is also possible that a strategy similar to that described above could be used in combination with plant protease insensitive variants of lysine oxidase proenzyme to obtain transgenic maize that are not stunted.

Example 12

This example illustrates apoplastic, vacuolar, endoplastic reticulum, and peroxisomal targeting of lysine oxidase proenzyme or enzyme.

To target the lysine oxidase proprotein to the extracellular or apoplastic space, a secretory signal peptide sequence derived from plants can be fused in frame to the amino terminus of the lysine oxidase proprotein gene. One example of such a sequence is the signal peptide derived from a barley cysteine endoproteinase gene (Koehler and Ho, 1990). Another example is the tobacco PR1b signal peptide (Cornelissen et al., 1986).

It is also recognized that both the lysine oxidase and tedanalactarn synthase proteins contain N-linked glycosylation sites that are not used in the native proteins derived from Trichoderma. To avoid inactivation caused by N-glycosylation of secreted lysine oxidase or tedanalactam synthase, the glycosylation sites of these proteins could be eliminated by site directed mutagenesis. More specifically, all or a subset of the amino acid sequences N(x)S/T could be converted to N(x)A by replacing the native Ser or Thr codon for an Ala codon. For the lysine oxidase proprotein (SEQ ID NO: 46), this would entail conversion of either all or a subset of T140, T325, S373, T391, and T423 to alanine or another result effective amino acid residue. Conversion of lysine oxidase residues N138, N323, N371, N389, and N421 to glutamine (Q) residues results in loss of enzymatic activity, indicating that this particular set of substitutions is not preferred. For the tedanalactam synthase protein (SEQ ID NO: 41), S188 and S424 could be converted to alanine residues.

Having constructed apoplastically targeted, glycosylation deficient lysine oxidase or tedanalactam synthase proteins, it is also possible to retain the proteins in the endoplasmic reticulum. This could be accomplished by an in frame fusion of DNA sequence encoding the peptide sequence KDEL to the C-termini of the apoplastically targeted lysine oxidase or tedanalactam synthase coding sequences (Munro and Pelham, 1987; Tillmann et al., 1989). It would also similarly be possible to achieve vacuolar localization via in frame fusions of vacuolar targeting signals (Bednarek et al., 1990; Neuhaus et al., 1991) to the C-termini of the apoplastically targeted, glycosylation deficient lysine oxidase or tedanalactam synthase proteins.

To target lysine oxidase enzyme or proenzyme to peroxisomes, the C-terminal peroxisomal targeting sequences could be fused in frame to the C-terminus of lysine oxidase (Gould et al., 1987; Volokita, 1991). In this example, an amino terminal peroxisomal targeting signal (nPTS) derived from a rice malate dehydrogenase gene (Seq ID NO: 54; SEQ ID NO: 55) was fused to the N-terminus of the lysine oxidase proenzyme with six N-terminal histidine residues. A plant expression cassette consisting of the 4as-1 promoter, the rice actin intron, the wheat CAB leader, the nPTS-lysine oxidase fusion gene, and a wheat tahsp 17 3' polyadenylation site was constructed in pMON25092. The pMON25092 NotI cassette containing the nPTS-lysine oxidase expression cassette was engineered into pMON33701 to obtain pMON38800, a plant transformation vector containing the nPTS-Lysine oxidase expression cassette as well as previously described neomycin phosphotransferase and tedanalactam synthase expression cassettes (FIG. 29).

Transgenic corn expressing both lysine oxidase and tedanalactam synthase in roots were obtained with pMON38800. Phenotypic analysis of this lines indicated that use of the nPTS targeting signal did not alleviate stunting associated with high level lysine oxidase expression in leaves. However, root specific or enhanced expression of the mitochondrial targeted lysine oxidase expression may alleviate stunting. It is also possible that a strategy similar to that described above could be used in combination with plant protease insensitive variants of lysine oxidase proenzyme to obtain transgenic maize that are not stunted.

Example 13

This example illustrates activation of lysine oxidase proprotein by corn rootworm midgut proteases and engineering of improved proenzyme variants.

The lysine oxidase gene encodes a 69 kDa proenzyme which is N-terminally cleaved when expressed in Trichoderma or Saccharomyces to yield a mature and enzymatically active protein of approximately 60 kDa. To determine if the lysine oxidase-69 (LO69) proenzyme (Seq ID NO: 46) expressed in corn protoplasts can be activated by the proteases present in the midgut of southern corn rootworm, midguts were dissected from late instar larvae and the proteases extracted. Protease activity assays confirmed the presence of proteases in this extract. This extract and appropriate controls were incubated for about 22 hours at 25° C. with extracts from protoplasts electroporated with pMON25040 (i.e. the CaMV35S promoter and hsp70 intron fused to the 1.9 kb lysine oxidase gene encoding the $M_r$ 69,000 proprotein, SEQ ID NO:45) and non-electroporated controls and assayed for lysine oxidase activity. These results are summarized in Table 20.

TABLE 20

Lysine oxidase activity in corn leaf protoplast extracts treated with southern corn rootworm midgut extracts.

| Sample | Treatment | Lysine oxidase Sp. Act. | Fold Difference[1] |
|---|---|---|---|
| LO69 | gut extract | 1292 U/μg protein | 130 |
| LO69 | gut extract, protease inhibitor | 997 | 97 |
| LO69 | BSA | 12 | 1.2 |
| LO69 | heated gut extract | 10 | 0 |
| control | all above treatments | 0 | NA |

[1]Fold difference is relative to the LO69 with heated gut extract
NA = not applicable To confirm that the observed increase in lysine oxidase activity was due to proteolysis of the proprotein, the LO69 and control extracts treated with both active and heated gut extract were analyzed by Western blot with antibodies directed against lysine oxidase. LO69 extract treated with the gut extract yielded a band that migrates with the "mature" lysine oxidase of approximately $M_r$ 60,000 while LO69 extracts treated with heated gut extract yield a much larger band of approximately $M_r$ 69,000. The Western data thus support our hypothesis that the CRW gut extracts activate the LO69 proenzyme by proteolysis.

These results indicate that expression of the LO69 zymogen in transgenic plants may prevent deleterious effects of lysine oxidase on plant growth and development. However, ingestion of LO69 expressing root tissue by CRW is likely to result in activation of lysine oxidase by proteolysis and subsequent insecticidal activity when the tedanalactam synthase protein is also present. To test the hypothesis that enzymatically inactive LO69 has insecticidal activity, LO69 proenzyme (LO69) was purified from a heterologous *Saccharomyces cerevisiae* system and tested for bioactivity in a diet overlay assay with SCRW (Table 21). The absence of LO activity in the proenzyme sample was confirmed by direct enzymatic assays just prior to exposure to insects. The results of this experiment indicate that SCRW growth is inhibited by ingestion of enzymatically inactive LO69 protoxin, supporting the concept that enzymatically inactive LO69 could be produced within transgenic plants to yield control of target insects upon ingestion.

TABLE 21

Bioactivity of the LO69 proenzyme when combined with Tedanalactam Synthase (50 kD) against Southern Corn Rootworm Larvae

| Sample (ppm)[1] | n | Surv | Av. Wght (mg) | SEM[2] | % inhibition[3] |
|---|---|---|---|---|---|
| Tris control | 18 | 18 | 2.6 | 0.48 | |
| 50 kD (2) | 18 | 18 | 3.5 | 0.46 | 0 |
| 50 kD (10)** | 18 | 18 | 1.5 | 0.39 | 39 |
| LO69 (2) | 18 | 17 | 2.1 | 0.56 | 20 |
| LO69 (10) | 17 | 17 | 3.3 | 0.52 | 0 |
| LO69 (20) | 18 | 18 | 2.8 | 0.51 | 0 |
| 50 kD (2)/LO (2) | 18 | 18 | 1.6 | 0.37 | 39 |
| 50 kD (2)/LO69 (2) | 18 | 18 | 1.5 | 0.4 | 41 |
| 50 kD (2)/LO69 (10) | 18 | 18 | 0.34 | 0.03 | 87 |
| 50 kD (2)/LO69 (20) | 18 | 15 | 0.59 | 0.26 | 77 |

[1]Sample Key: 50 kD = tedanalactam synthase; LO69 = LO proenzyme; LO = LO (active enzyme); (2) = concentration of 2 ppm
[2]SEM is standard error of measurement
[3]% inhibition is: Control Larval Weight − Test Larval Weight/Control Larval Weight × 100.
**Low level LO contamination in the Trichoderma derived 50 kD sample accounts for the bioactivity observed at this concentration of the 50 kD preparation.

Note that the stability of the native LO69 zymogen in planta may be improved by changing the amino acid sequences in the proprotein region that are recognized by plant proteases. These sequences can be identified by obtaining the N-terminal protein sequence of enzymatically active lysine oxidase (i.e. the approximately $M_r$ 60,000 protein produced by proteolysis of the $M_r$ 69,000 proprotein) isolated from transgenic plants. For example, mature and enzymatically active lysine oxidase from roots of corn transformed with pMON25040 or pMON30417 is apparently produced by cleavage at the C-terminus of the glu 80 residue. A mutagenized or improved LO69 proenzyme would display greater stability in transgenic plants, resulting in lower levels of enzymatically active lysine oxidase and decreased impact of plant growth and/or lysine content. The improved LO69 proenzyme would retain amino acid sequences recognized by coleopteran midgut proteases, resulting in full activation and biological activity upon ingestion (Table 22).

TABLE 22

Design of lysine oxidase proenzyme variants resistant to plant proteases yet susceptible to target insect midgut proteases

| Name | Sequence | Type | SEQ ID NO |
|---|---|---|---|
| WT1 | N-KPALLKEAPRAEEELPPRK-C | wild type | 46 |
| mut1 | N-KPALLGGGGXXXXXXGGGG-C | mutant | 56 |

TABLE 22-continued Design of lysine oxidase proenzyme variants
resistant to plant proteases yet susceptible to
target insect midgut proteases

| Name | Sequence | Type | SEQ ID NO |
|---|---|---|---|
| mut2 | N-GGGSGGXXXXXXGGGPPRK-C | mutant | 57 |
| mut3 | N-KPGGGGXXXXXXGGGPPRK-C | mutant | 58 |

(X is any of the 20 naturally occurring amino acid residues)

It is also recognized that amino acid residues lys 68 through lys 86 of the lysine oxidase proenzyme (SEQ ID NO: 46) represent a protease sensitive region in the lysine oxidase proprotein or zymogen. Variants in this region may yield the desired characteristic of being susceptible to CRW gut proteases, yet resistant to plant root proteases. One preferred embodiment of this invention would be the substitution of this entire region of nineteen (19) amino acids with a peptide sequence that represents an optimal corn rootworm gut protease cleavage site. Potential representation of this type of amino acid substitutions are shown in SEQ ID. NOS: 56–58. Methods for identifying optimal protease substrates in combinatorial peptide libraries have been identified and could be employed (Duan and Laursen, 1994). For example, a library of protease substrates consisting of a randomized target protease cleavage site separating a floresence donor and acceptor pair can be immobilized on a cellulose filter. This filter is then exposed to plant and insect gut proteases; peptides that floresce only in the presence of insect proteases would represent preferred substrates.

It is finally recognized that the entire lysine oxidase proenzyme sequence (SEQ ID NO: 46) extending from amino acid residues 1 (met) to 87 (val) may be modified to encode a variant with the desired property of being resistant to activation by corn root proteases yet sensitive to activation by corn rootworm gut proteases. This region could be mutagenized by either site-directed or random mutagenesis techniques familiar to those skilled in the art (Kunkel, 1985; Spee et al, 1993; Muhlrad et al, 1992). The population of mutagenized lysine oxidase proprotein expressing clones expressed in *Saccharomyces cerevisiae* could potentially be screened via exposure to plant and insect proteases followed by lysine oxidase enzymatic assays to identify the variant with the desired protease activation properties. Finally, the improved lysine oxidase zymogen could be targeted to plastids, mitochondria, the apoplastic space, or the vacuole as described above.

The lysine oxidase proenzyme sequence extending from amino acids 1 to 87 (SEQ ID NO: 46) may also be fused to proteins other than lysine oxidase to create other zymogens that would be activated upon insect ingestion. The resultant chimeric protein could then be activated by coleopteran or lepidopteran midgut proteases to yield enzymatically active, insecticidal proteins.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

REFERENCES

The following references, to the extent that they provide exemplary procedural or other details supplementary to those set forth herein, are specifically incorporated herein by reference.

The following references, to the extent that they provide exemplary procedural or other details supplementary to those set forth herein, are specifically incorporated herein by reference.

Armstrong, C. L. et al. *Plant Cell Rep.* 9: 335–339 (1990).
Bagdasarian, M. et al. *Gene* 16: 237–247 (1981).
Barry, G. F. and Kishore, G. M. "Glyphosate tolerant plants." U.S. Pat. No. 5,463,175 (1995).
Barton, K. et al. *Plant Physiol.* 85: 1103–1109 (1987).
Bechtold, N. et al. *C.R. Acad. Sci. Paris, Life Sciences* 316: 1194–1199 (1993).
Bednarek, S. Y. et al. *Plant Cell* 2: 1145–1155 (1990).
Bevan, M. et al. *Nature* 304: 184 (1983).
Boutry, M. et al. *Nature* 328: 340–342 (1987).
Bright, H. J. and Porter, D. J. T. in The Enzymes, Vol. 12B:421–505 (1975).
Brown, S. M. and Santino, C. G. "Enhanced expression in plants." U.S. Pat. No. 5,424,412 (1995).
Corbin, D. R. et al. *Appl. Environ. Microbiol.* 60 (12): 4239–4244 (1994).
Cornelissen, B. J. C. et al. *EMBO J.* 5: 37–40 (1986).
Cronan Jr., J. M. and Cardellina, J. H. *Natural Products Lett.* 5: 85–88 (1994).
Ditta, G. et al. *Proc. Natl. Acad. Sci.U.S.A.* 77: 7347–7351 (1980).
Duan, Y. and Laursen, R. A. *Anal. Biochem.* 216: 431–438 (1994).
Fedoroff, N. et al. *Cell* 35: 235–242 (1983).
Feinberg, A. P. and Vogelstein, B. *Anal. Biochem.* 132: 6–13 (1983).
Fischhoff, D. A. and Perlak, F. J. "Synthetic plant genes and method for preparation." European Patent Application, Publication Number 0 385 962 (1990).
Fischhoff, D. A. et al. *Bio/Technology* 5: 807–813 (1987).
Frischauf, A. M. et al. *Methods Enzymol.* 153: 103–115 (1987).
Frohman, M. A. et al. *Proc. Natl. Acad. Sci. U.S.A.* 85: 8998–9002 (1988).
Fromm, M. E. et al. *Bio/Technology* 8: 833–839 (1990).
Fromm, M. E. et al. *Nature* 319: 791–793 (1986).
Gallo *Methods Enzymol.* 71: 665–667 (1981).
Gould et al. *J.Cell Biol.* 105: 2923–2931 (1987).
Halpin, C. and Ryan, M. "Expression of self-processing polyproteins in transgenic plants". International Patent Application Number WO 95/17514 (1995).
Herrera-Estrella, L. et al. *Nature* 303: 209 (1983).
Hills, T. M. and Peters, D. C. *J. Econ. Entomol.* 64: 764–765 (1971).
Hope, et al. *Biochem. J.* 105: 663–667 (1967).

Horsch, R. B. et al. *Science* 227: 1229–1231 (1985).
Horton, R. M. et al. *Gene* 77: 61–68 (1989).
Klee, H. J. et al. *Bio/Technology* 3: 637–642 (1985).
Knauf, V. C. and Nester, E. *Plasmid* 8: 43–54 (1982).
Knight, S. G. *J.Bacteriol.* 55: 401–407 (1948).
Koehler, S. M. and Ho, T. H. *Plant Cell* 2(8): 769–783 (1990).
Kreig, A. et al. *Pathotyp. Z. Ang. Ent.* 96: 500–508 (1983).
Kunkel, T. A. *Proc. Natl. Acad. Sci. USA* 82:488–492 (1985)
Kusakabe, H. et al. *J. Biol. Chem.* 256: 976–981 (1980).
Kusakabe, H. et al. *Agric. Biol. Chem.* 43: 337–343 (1979).
Lam et al. "Promoter enhancer element for gene expression in plant roots". U.S. Pat. No. 5,023,179 (1991).
Lee, C. C. et al. *Science* 239: 1288–1291 (1988).
Matsudaira, P. *J. Biol. Chem.* 261: 10035–10038 (1987).
McElroy, D. et al. *Plant Cell* 2: 163–171 (1990).
Muhlrad et al. *Yeast* 8:79–82 (1992).
Munro, S. and Pelham, H. R. B. *Cell* 48: 899–907 (1987).
Neuhaus, J-M. et al. *Proc. Natl. Acad. Sci. USA* 88:10362–10366 (1991).
Niedermann, D. M. and Lerch, K. *J. Biol. Chem.* 265: 17246–17251 (1990).
Perlak, F. J. et al. *Bio/technology* 8: 939–943 (1990).
Rogers, S. G. "Promoter for transgenic plants". U.S. Pat. No. 5,378,619 (1995).
Russell, D. A. et al. *Plant Cell Reports* 13: 24–27 (1993).
Schilperoort et al. EPO publication 0 120 516.
Spree, J. H. et al. *Nuc. Acid. Res.* 21:77–778 (1993).
Stumpf, P. K. and Green, D. E. *J. Biol. Chem.* 153: 387 (1944).
Tillmann, U. et al. *EMBO J.* 8(9): 2463–2467 (1989).
Vaeck, M. et al. *Nature* 328: 33–37 (1987).
Volokita, M. *Plant J.* 1: 361–366 (1991)
White, J. A. and Scandalios *Proc. Nat. Acad. Sci. U.S.A.* 86:3534–3538 (1989).
Winter, J. et al. *Mol. Gen. Genet.* 221(2): 315–319 (1988).
Xu, Y. et al. *Plant Mol. Biol.* 27: 237–248 (1995).
Yamamoto, Y. et al. *Plant Cell* 3: 371–382 (1991).

---

What is claimed is:

1. A composition for controlling insect infestation of plants, said composition comprising:
a lysine oxidase enzyme; and a protein comprising an amino acid sequence as set forth in SEQ ID NO:41 wherein said composition is ingested by an insect.

2. The composition of claim 1, wherein said composition exhibits coleopteran insecticidal activity.

3. The composition of claim 2, wherein said coleopteran insecticidal activity is effective in controlling coleopteran species selected from the group consisting of Diabrotica, Melanotus, Leptinotarsa, and Anthonomus.

4. The composition of claim 3, wherein said coleopteran insecticidal activity is effective in controlling insects selected from the group consisting of boll weevil (BWV), corn rootworm (CRW), wireworm (WW), and Colorado potato beetle (CPB).

5. The composition of claim 1, wherein said lysine oxidase enzyme and said protein are present respectively in a molar ratio of about 100:1 to about 1:1.

6. The composition of claim 1, wherein said lysine oxidase enzyme and said protein are present respectively in a molar ratio of about 10:1 to about 1:1.

7. The composition of claim 1, wherein said protein and said lysine oxidase enzyme are present respectively in a molar ratio of about 100:1 to about 1:1.

8. The composition of claim 1, wherein said protein and said lysine oxidase enzyme are present respectively in a molar ratio of about 10:1 to about 1:1.

9. A method of controlling insect infestation of plants comprising providing a composition comprising:

a lysine oxidase enzyme; and a protein comprising an amino acid sequence as set forth in SEQ ID NO:41;

wherein said composition is ingested by an insect.

10. The method of claim 9, wherein said composition exhibits coleopteran insecticidal activity.

11. The method of claim 10, wherein said coleopteran insecticidal activity is effective in controlling coleopteran species selected from the group consisting of Diabrotica, Melanotus, Leptinotarsa, and Anthonomus.

12. The method of claim 11, wherein said coleopteran insecticidal activity is effective in controlling insects selected from the group consisting of boll weevil (BWV), corn rootworm (CRW), wireworm (WW), and Colorado potato beetle (CPB).

13. The method of claim 9, wherein said lysine oxidase enzyme and said protein are present respectively in said mixture in a molar ratio of about 100:1 to about 1:1.

14. The method of claim 9, wherein said lysine oxidase enzyme and said protein are present respectively in said composition in a molar ratio of about 10:1 to about 1:1.

15. The method of claim 9, wherein said protein and said lysine oxidase enzyme are present respectively in said composition in a molar ratio of about 100:1 to about 1:1.

16. The method of claim 9, wherein said protein and said lysine oxidase enzyme are present respectively in said composition in a molar ratio of about 10:1 to about 1:1.

* * * * *

UNITED STATES PATENT AND TRADEMARK OFFICE
CERTIFICATE OF CORRECTION

PATENT NO.   : 6,372,211 B1
DATED        : April 16, 2002
INVENTOR(S)  : Barbara G. Isaac, John T. Greenplate, John P. Purcell and Charles P. Romano It is certified that error appears in the above-identified patent and that said Letters Patent is hereby corrected as shown below:

<u>Title page,</u>
Item [73], Assignee, please correct the Assignee name by deleting "Monsanto Technolgy LLC" and inserting -- Monsanto Technology LLC -- therefor.

Signed and Sealed this

First Day of October, 2002

Attest:

Attesting Officer

JAMES E. ROGAN
*Director of the United States Patent and Trademark Office*